United States Patent
Li et al.

(12)

(10) Patent No.: US 6,630,176 B2
(45) Date of Patent: Oct. 7, 2003

(54) HERBAL REMEDIES FOR TREATING ALLERGIES AND ASTHMA

(75) Inventors: Xiu-Min Li, Mamaroneck, NY (US); Hugh A. Sampson, Larchmont, NY (US)

(73) Assignee: Mount Sinai School of Medicine of New York University, New York, NY (US)

( * ) Notice: Subject to any disclaimer, the term of this patent is extended or adjusted under 35 U.S.C. 154(b) by 0 days.

(21) Appl. No.: 09/800,815

(22) Filed: Mar. 7, 2001

(65) Prior Publication Data

US 2003/0157126 A1 Aug. 21, 2003

Related U.S. Application Data

(60) Provisional application No. 60/187,614, filed on Mar. 7, 2000.

(51) Int. Cl.[7] .................... A61K 35/78; A61K 35/84
(52) U.S. Cl. .................. 424/728; 424/725; 424/739; 424/756; 424/195.16; 514/826
(58) Field of Search .................. 424/725, 728, 424/739, 756, 195.16; 514/826

(56) References Cited

U.S. PATENT DOCUMENTS

| 5,411,733 | A | * | 5/1995 | Hozumi et al. |
| 6,027,728 | A | | 2/2000 | Yuen |
| 6,180,106 | B1 | * | 1/2001 | Keller et al. |

FOREIGN PATENT DOCUMENTS

| CN | 1104506 | * | 7/1995 |
| JP | 60105623 | * | 6/1985 |
| JP | 60222423 | * | 11/1985 |
| JP | 62234014 | * | 10/1987 |
| JP | 01128933 | * | 5/1989 |
| JP | 10036276 | * | 2/1998 |
| JP | 1101222178 | * | 1/1999 |
| WO | WO 00/02521 | | 1/2000 |

OTHER PUBLICATIONS

Johnson, T. CRC Ethnobotany Desk Reference. 1999. CRC Press, NY, NY. p. 49 (Plant No. 1500).*
Patent Abstracts of Japan Publication No. 07138173, May 30, 1995.
Patent Abstracts of Japan Publication No. 01056619, Mar. 3, 1989.
Patent Abstracts of Japan Publication No. 06321795, Nov. 22, 1994.
Patent Abstracts of Japan Publication No. 61122221, Jun. 10, 1986.
Derwent Database WPI, Abstract No. 1998–043019, Dec. 11, 1996.
Derwent Database WPI, Abstract No. 1999–327867, Mar. 3, 1999.
Derwent Database WPI, Abstract No. 2000–443095, Jan. 26, 2000.
Derwent Database WPI, Abstract No. 2000–491533, Jan. 15, 1997.

* cited by examiner

*Primary Examiner*—Christopher R. Tate
(74) *Attorney, Agent, or Firm*—Dorsey & Whitney LLP

(57) ABSTRACT

The present invention provides herbal compositions that can prevent or reduce the severity, intensity, or duration of allergic and/or asthmatic symptoms and/or can prevent or delay the development of an allergic or asthmatic response to an antigen. The compositions may optionally include one or more adjuvants, cytokines, encapsulating materials, or pharmaceutical carriers or excipients, and may be administered prior to, during, or after the development of allergic or asthmatic symptoms in sensitized individuals. Alternatively or additionally, the compositions may be administered prior to sensitization to a particular antigen; preferably substantially concurrently with exposure to the antigen.

6 Claims, 27 Drawing Sheets

(1 of 27 Drawing Sheet(s) Filed in Color)

HERBAL REMEDIES FOR TREATING ALLERGIES AND ASTHMA

RELATED APPLICATIONS

The present application claims priority to provisional application, U.S. Serial No. 60/187,614, filed Mar. 7, 2000, incorporated herein by reference in its entirety.

BACKGROUND

Allergic and asthmatic reactions pose serious public health problems worldwide. Pollen allergy alone (allergic rhinitis or hay fever) affects about 10–15% of the population, and generates huge economic costs. For example, reports estimate that pollen allergy generated $1.8 billion of direct and indirect expenses in the United States in 1990 (Fact Sheet, National Institute of Allergy and Infectious Diseases, www.niaid.nih.gov/factsheets/allergystat.html; McMenamin, Annals of Allergy 73:35, 1994; incorporated herein by reference). More serious than the economic costs associated with pollen and other inhaled allergens (e.g., molds, dust mites, animal danders) is the risk of anaphylactic reaction observed with allergens such as food allergens, insect venoms, drugs, and latex.

Allergic reactions occur when an individual's immune system overreacts, or reacts inappropriately, to an encountered antigen. No allergic reaction is thought to occur the first time an individual is exposed to a particular antigen. However, the initial immune response to an antigen primes the system for subsequent allergic reactions. In particular, the antigen is taken up by antigen presenting cells (e.g., macrophages or dendritic cells) that degrade the antigen and then display antigen fragments to T cells. The activated T cells respond by secreting a collection of cytokines that affect other cells of the immune system. The profile of cytokines secreted by responding T cells determines whether subsequent exposures to the particular antigen will induce allergic reactions. When T cells respond by secreting interleukin-4 (IL-4), the effect is to stimulate the maturation of B cells that produce IgE antibodies specific for the antigen. These antigen-specific IgE antibodies then attach to specific receptors on the surface of mast cells and basophils, where they act as a trigger to initiate a rapid reaction to subsequent exposures to the antigen.

When the individual next encounters the antigen, it is quickly bound by these surface-associated IgE molecules. Each antigen typically has more than one IgE binding site, so that the surface-bound IgE molecules quickly become crosslinked to one another through their simultaneous (direct or indirect) associations with antigen. Such cross-linking induces mast cell degranulation, resulting in the release of histamines and other substances that induce the symptoms associated with allergic reaction. Individuals with high levels of IgE antibodies are known to be particularly prone to allergies.

Allergic asthma is a chronic, IgE-mediated lung disease characterized by inflammation and airway hyperresponsiveness (AHR). Asthma is a major public health problem in the United States; nearly 17 million Americans suffer from this often debilitating disease. Moreover, asthma morbidity and mortality have been rising over the last two decades. The prevalence rate increased by 75% from 1980 to 1994, and despite the increased use of medications, deaths from asthma rose 58%.

Clinically, asthma is expressed as episodic breathlessness, wheezing, chest tightness, and cough (U.S. Centers for Disease Control. Morbidity and Mortality 47:1022, 1998; incorporated herein by reference). The airways of asthmatic subjects are characterized by chronic inflammation with infiltration of the bronchial mucosa by lymphocytes, eosinophils, and mast cells together with epithelial desquamation, goblet cell hyperplasia, and thickening of the submucosa (Steering Committee for International Study of Asthma and Allergies in Childhood, Lancet 351:1225, 1998; Kay J. Allergy Clin. Immunol. 87:893, 1991; each of which is incorporated herein by reference).

Numerous studies have demonstrated that Th2-type cytokines, such as IL-4, IL-5, and IL-13, produced by activated $CD4^+$ T cells, play a central role in the pathogenesis of allergic asthma (see, for example, Lemanske et al., in Allergy: Principles and Practice. C. V. Mosby, Co., St. Louis, Mo., pg. 320, 1993; Mosmann et al., J. Immunol. 136:2348, 1986; Mosmann et al., Annu. Rev. Immunol. 7:145, 1989; Walker et al., Am. Rev. Respir. Dis. 146:109, 1992; Robinson et al., N. Engl. J. Med. 326:298, 1992; Finkleman et al., J. Immunol. 141:2335, 1988; Schleimer et al., J. Immunol. 148:1086, 1992; Hamaguchi et al., J. Exp. Med. 165:268, 1987; Campbell et al., Proc. Natl. Acad. Sci. USA 84:6629, 1987; Zurawski et al., Immunol. Today 15:19, 1994; each of which is incorporated herein by reference).

Atopic human subjects, when exposed to the relevant asthmatic antigen, suffer an acute IgE-dependent response, often followed by a late-phase inflammatory response 6–12 hours later (Beasley et al., Am. Rev. Respir. Dis. 139:806, 1989; Metzger et al., Clin. Rev. Allergy 3:145, 1985; each of whichlis incorporated herein by reference). The early (immediate) phase response is associated with mast cell degranulation and release of mediators such as histamine, tryptase, leukotrienes, and platelet-activating factor (Busse et al., Agents Actions Suppl. 28:41, 1989; Lemanske et al., in Allergy: Principles and Practice. C. V. Mosby, Co., St. Louis, Mo., pg. 320, 1993; each of which is incorporated herein by reference); the late phase response is associated with the infiltration of inflammatory cells, predominantly eosinophils, which release eosinophil major basic protein and other mediators that damage the epithelium and induce bronchoconstriction (Beasley et al., Am. Rev. Respir. Dis. 139:806, 1989; Busse et al., Agents Actions Suppl. 28:41, 1989; each of which is incorporated herein by reference).

As the significance of inflammation has become recognized in the pathogenesis of airway hyperresponsiveness, efforts have been made to treat asthma by reducing the inflammatory process. Corticosteroids are the most potent known non-specific anti-inflammatory agents and have been found to produce notable improvement in objective lung function of asthmatics. In view of the substantial side effects associated with systemic corticosteroids, inhaled corticosteroids are currently the first line of treatment. Inhaled steroids can be effective in decreasing inflammation and bronchoconstriction in patients, but the lack of specificity of their effects can also have negative results. Although the most frequently reported side effects of inhaled corticosteroids are local, systemic effects have also been reported. Thinning of the skin, bruising, adrenal suppression, decreased bone metabolism, and decreased growth (Barnes, N. Engl. J. Med. 332:868, 1995; incorporated herein by reference) are of particular concern, especially among children, in whom asthma appears to be rapidly increasing in frequency.

One approach to treating allergies is antigen immunotherapy, which attempts to "vaccinate" a sensitive individual against a particular allergen by periodically injecting or treating the individual with a crude suspension of the raw allergen. The goal is to modulate the allergic response mounted in the individual through controlled administration of known amounts of antigen. If the therapy is successful, the individual's allergic response is diminished, or can even disappear. However, the therapy can require several rounds of vaccination, over an extended time period (3–5 years), and very often does not produce the desired results. Moreover, certain individuals suffer anaphylactic reactions to the vaccines, despite their intentional, controlled administration.

Another commonly used approach to treating allergic symptoms is the administration of histamine antagonists. These drugs are widely available in over-the-counter formulations, but unfortunately they merely mask the symptoms of the allergic response rather than providing any type of permanent cure or protection against recurrence.

Efforts are underway to develop more specific treatments for allergy and asthma (see, for example, Fahy et al., *Am. J. Respir. Crit. Care Med.* 155:1828, 1997; Boulet et al., *Am. J. Respir. Crit. Care Med.* 155:1835, 1997; Kung et al., *Am. J. Respir. Cell Mol. Bio.* 12:360, 1995; Mauser et al., *Am. J. Respir. Crit. Care Med.* 152:467, 1995; Holgate et al., *J. Allergy Clin. Immunol.* 98:1, 1996; each of which is incorporated herein by reference). Also, non-traditional treatments for these maladies are being explored. However, there remains a need for the development of improved allergy and asthma therapies, and particularly therapies to reduce the risk of anaphylaxis.

SUMMARY OF THE INVENTION

The invention provides improved treatments for allergies and asthma. In particular, the invention provides herbal formulation compositions that, when administered to an individual suffering from asthmatic or allergic symptoms, reduce the severity, intensity, and/or duration of at least some of those symptoms. Inventive compositions preferably reverse established allergic or asthmatic reactions to particular antigens. Alternatively or additionally, inventive compositions may prevent or delay an allergic or asthmatic reaction and/or may block or reduce the development of allergic or asthmatic sensitivity to antigens.

In one preferred embodiment, an inventive composition comprises one or more components of Fructus Pruni Mume (Wu Mei), Pericarpium Zanthoxyli Bungeanum (Chuan Jiao), Herba cum Radice Asari (Xi Xin), Rhizoma Coptidis (Huang Lian), Cortex Phellodendri (Huang bai), Rhizoma Zingiberis Officinalis (Gan Jiang), Radix Lateralis Aconiti Carmichaeli Praeparata (Fu Zi), Ramulus Cinnamomi Cassiae (Gui Zhi), Radix Ginseng (Ren Shen), and Radix Angelicae Sinensis (Dong gui). Other preferred compositions additionally comprise one or more components of *Ganoderma lucidum* (Ling Zhi). In a particularly preferred embodiment, the composition comprises the Chinese herbal remedy Wu Mei Wan (WMW) plus *Ganoderma lucidum* (Ling Zhi, LZ).

In another preferred embodiment, the composition comprises one or more components of *Perillae frutescens* (su zi), Descurainia Sophia (ting li zi), *Raphanus sativus* L. (lai fu zi), *Marus alba* L. (sang bai pi), *Prunus armeniaca* (xing ren), *Scutellaria baicalensis* (huang qin), *Glycyrrhiza uralensis* (gan cao), *Ziziphus jujuba* (da zao), *Aster tataricus* (zi wan), *Pteria margaritaferae* (zhen zhu mu), and *Aussilago farfara* (kuan dong hua).

In yet another preferred embodiment, the composition comprises one or more components of *Perillae frutescens* (su zi), Descurainia Sophia (ting li zi), *Prunus armeniaca* (xing ren), *Scutellaria baicalensis* (huang qing), *Sophora flavescens* (ku sen), *Angesica sinensis* (don gui), *Paeonia lactiflora* (bai shao), *Peuraria lobata* (ge gen), *Platycodon grandiflorum* (jie gen), *Pteria margaritaferae* (zhen zhu mu), *Ganoderma lucidum* (ling zhi), *Glycyrrhiza uralensis* (gan cao), *Ziziphus jujuba* (da zao), and *Frash zingiber officinal* (sheng jiang).

In certain preferred embodiments of the invention, inventive compositions are administered in combination with one or more standard therapies. For example, inventive compositions may be administered in combination with corticosteroids (e.g., inhaled, injected, or orally delivered corticosteroids), anti-histamines, decongestants, cromolyn sodium, standard immunotherapy, rush immunotherapy, etc. used to treat allergic or asthmatic symptoms.

Inventive compositions may optionally be characterized in one or more animal model systems.

Furthermore, the present invention provides a method of formulating an herbal remedy of the present invention, and/or of identifying active ingredients in inventive herbal compositions. For example, one or more active components of the herbs of the inventive compositions may optionally be extracted or purified using any technologies known in the art including, but not limited to chromatography, aqueous extraction, organic solvent extraction, etc. The active component and/or whole herbs may be combined with other pharmaceutically acceptable excipients or carriers to make pharmaceutical compositions.

The present invention also provides methods of treating allergies or asthma and/or preventing the development of allergies or asthma. The compositions of the present invention may be administered to an individual to prevent the development of, or reduce symptoms of, an allergic or asthmatic response to an allergen. For example, the inventive compositions may be administered substantially simultaneously with a known allergen in order to alter the immune response so that an allergic or asthmatic response does not develop, or develops to a lesser extent than would be observed in the absence of the inventive composition. In another preferred embodiment, the inventive composition is administered before exposure to a known allergen in order to lessen the allergic or asthmatic reaction. In yet another embodiment, the inventive composition is administered after exposure to a known allergen or after development of sensitization to the allergen in order to lessen the effect of potential allergic or asthmatic reactions in the future.

The present invention also provides methods of identifying and characterizing herbal remedies useful in the treatment of allergic reactions and asthma. In a preferred embodiment, an inventive test herbal remedy is administered to an animal model known to have an immune response similar to that of the individual to be treated with the herbal remedy. The herbal remedy may be administered at any time including, but not limited to, prior to sensitization, during sensitization, after sensitization, prior to challenge, during challenge, or after challenge. In a particularly preferred embodiment, the animal model used is the allergic mouse model. In vitro assays may also be used in characterizing herbal remedies. In a particularly preferred embodiment, a basophil histamine release assay is used in assessing herbal remedies.

In another aspect, the present invention provides methods of identifying herbs useful in preparing herbal remedies and methods of identifying active components of these herbs. Herbs or mixture of herbs are administered to animal models of allergic disease or are used in in vitro assays known to predict effects in vivo. In a preferred embodiment, the active components of the herbs or mixture of herbs are purified or partially purified. Various methods of purification and preparation may be used in providing the formulations to be studied. The prepared/purified formulations may be also used in the various in vitro and in vivo assays described in the present patent application to identify those herbs and active components responsible for treating or preventing allergic disease.

BRIEF DESCRIPTION OF THE DRAWING

The patent or application file contains at least one drawing executed in color. Copies of the patent or patent application publication with color drawing(s) will be provided by the office upon request and payment of the necessary fee.

DEFINITIONS

Figure 1:
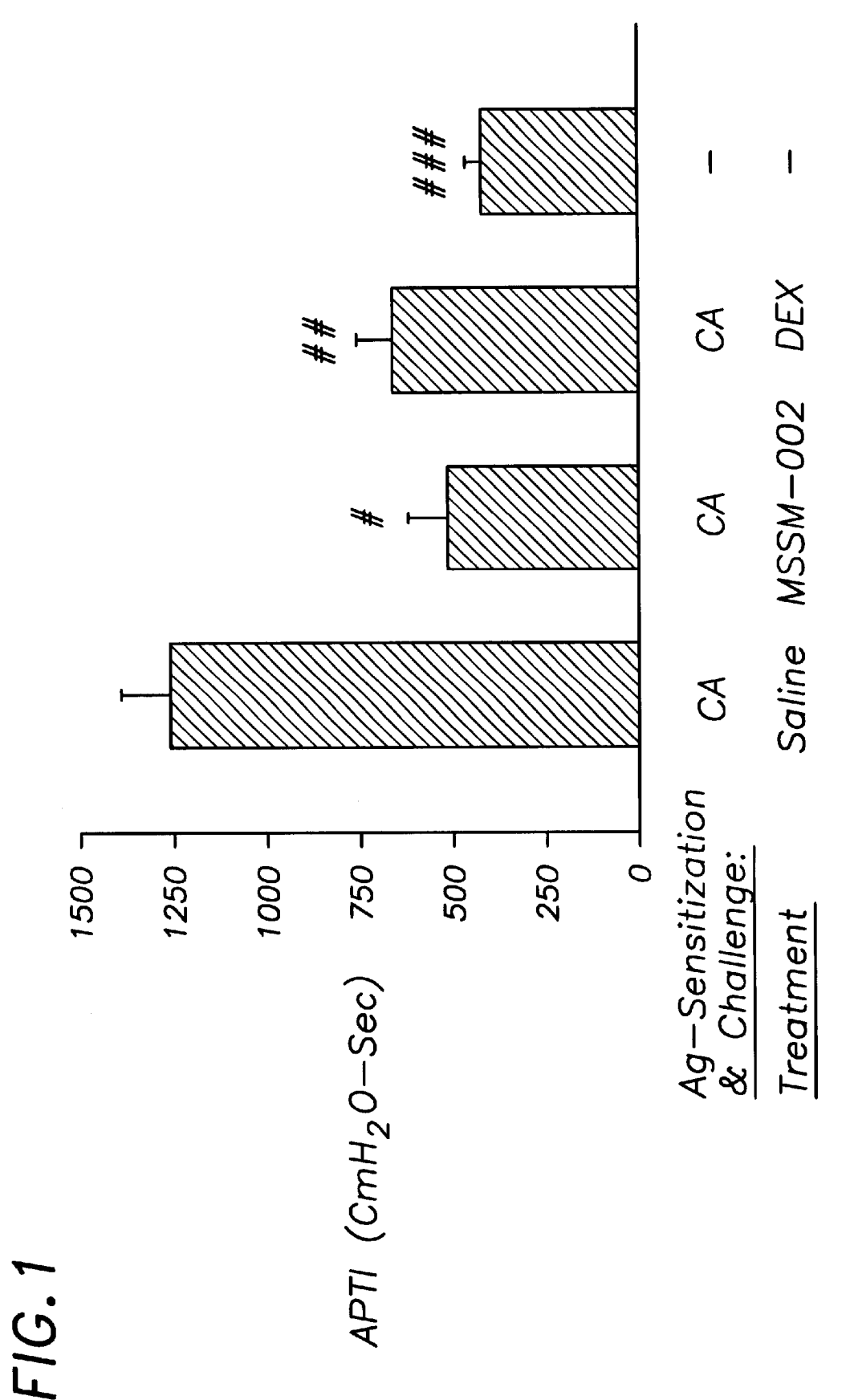
FIG. 1 shows the effect of MSSM-002 administration on antigen-induced airway hyperresponsiveness in a murine asthma model. Three days following the last Ag-challenge, AHR in each group (n greater than or equal to 8) was determined by measuring the airway pressure change following acetylcholine (Ach) challenge. Results were expressed as mean±SEM. #, $p<0.0001$; ##, $p<0.003$; ###, $p<0.00004$ vs. saline).

As used herein, the following terms have the following definitions:

"Active component": An "active component" of an herb or herbal formulation, is a compound or collection of compounds that is present in the herb or formulation and that, when separated from at least some other herbal components, retains at least some of a desired biological activity of the intact herb or herbal formulation. Preferably, the active component retains at least about 20% of the biological activity, more preferably at least about 30%, 40%, 50%, 60%, 70%, 80%, 90%, 95%, or 99%.

"Allergen": An "allergen" is an antigen that (i) elicits an IgE response in an individual; (ii) elicits an asthmatic reaction (e.g., chronic airway inflammation characterized by eosinophilia, airway hyperresponsiveness, and excess mucus production), whether or not such a reaction includes a detectable IgE response; and/or (iii) elicits an allergic reaction (e.g., sneezing, watery eyes, puritis, diarrhea, anaphylaxis), whether or not such a reaction includes a detectable IgE response.

"Allergic individual": "Allergic individual" refers to an individual with sensitivities to particular antigens or allergens as exhibited by (i) eliciting an IgE response in an individual sufficient to cause a measurable clinical response; (ii) eliciting an asthmatic reaction (e.g., chronic airway inflammation characterized by eosinophilia, airway hyperresponsiveness, and excess mucus production), whether or not such a reaction includes a detectable IgE response; and/or (iii) eliciting the signs and symptoms of an allergic reaction (e.g., sneezing, watery eyes, puritis, redness, diarrhea, anaphylaxis), whether or not such a reaction includes a detectable IgE response. Such an individual has a reaction to a relatively innocuous antigen that does not cause a similar reaction upon exposure in most other members of the population. This reaction in an allergic individual can cause a harmful immune response and/or tissue damage. Symptoms of allergy may consist of exaggerated or pathological reaction (e.g., sneezing, respiratory distress, itching, or skin rashes) to substances, situations, or physical states that are without comparable effect on the average individual.

"Allergic reaction": An allergic reaction is a clinical response by an individual to an antigen. Symptoms of allergic reactions can affect the cutaneous (e.g., urticaria, angioedema, pruritus), respiratory (e.g., wheezing, coughing, laryngeal edema, rhinorrhea, watery/itching eyes), gastrointestinal (e.g., vomiting, abdominal pain, diarrhea), and/or cardiovascular (if a systemic reaction occurs) systems. For the purposes of the present invention, an asthmatic reaction is considered to be a form of allergic reaction. In certain preferred embodiments, the allergic reaction involves an IgE response in an individual sufficient to cause a measurable clinical response.

"Animal": The term animal, as used herein, refers to non-human animals, including, for example, mammals, birds, reptiles, amphibians, and fish. Preferably, the non-human animal is a mammal (e.g., a rodent, a mouse, a rat, a rabbit, a monkey, a dog, a cat, or a pig). An animal may be a transgenic animal.

"Antigen": An "antigen" is (i) any compound or composition that elicits an immune response; and/or (ii) any compound that binds to a T cell receptor (e.g., when presented by an MHC molecule) or to an antibody produced by a B-cell. Those of ordinary skill in the art will appreciate that an antigen may be a collection of different chemical compounds (e.g., a crude extract or preparation) or a single compound (e.g., a protein).

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc. Also, two entities or agents may be "associated" with one another by being present together in the same composition.

"Asthmatic individual": The term "asthmatic individual" refers to an individual who experiences asthmatic symptoms (e.g., chronic airway inflammation characterized by eosinophilia, airway hyperresponsiveness, and excess mucus production) upon inhalation of a particular substance or antigen. Asthmatic individuals do not necessarily exhibit a detectable production of IgE.

"Cytokine": A "cytokine" is a small molecule that is released from or expressed by a cell and can alter the behavior or regulate the activity of one or more immunologically relevant target cells expressing a receptor for the cytokine. Cytokines that, if expressed by an antigen presenting cell, or by another cell, during presentation of antigen to a T cell would induce a particular response in that T cell can be classified according to the type of response they induce in the T cell. For example, cytokines that induce a Th1 response (e.g., IL-12, IL-2, IL-18, IL-1β or fragments thereof, IFNα, and/or IFNγ, etc.) are referred to herein as "Th1 stimulating cytokines"; cytokines that induce a Th2 response (e.g., IL-4, etc.) are referred to herein as "Th2 stimulating cytokines". Cytokines that are produced during a Th1 response (e.g., IFNγ, TNFβ, etc.) are referred to as "Th1 cytokines"; cytokines that are produced during a Th2 response (e.g., IL-4, IL-5, etc.) are referred to as "Th2 cytokines".

"Effective amount": The "effective amount" of an agent or composition refers to the amount necessary to elicit the desired biological response. The effective amount of the active components of an herb or herbal remedy is the amount necessary to decrease a particular sign and/or symptom (e.g., rhinorrhea, watery eyes, puritis, drop in blood pressure, drop in body temperature, level of IgE, production of cytokines, etc.) of an allergic reaction or asthma. The decrease may be a 10%, 20%, 30%, 40%, 50%, 60%, 70%, 80%, 90%, 95%, or 98% decrease. The effective amount of an active component of an herb or herbal remedy in a tolerizing composition is the amount that, when administered to an individual who is sensitized to an antigen, results in tolerization of the individual to the antigen.

"Inducing agents": Inducing agents are compounds or other agents that induce a professional antigen presenting cell (pAPC) to produce stimulating cytokines. For example, if it is desired that a pAPC secrete Th1 stimulating cytokines, then factors such as LPS, CD40, CD40 ligand, BCGs, oligonucleotides containing CpG motifs, TNFα, and microbial extracts such as preparations of *Staphylococcus aureus*, heat killed Listeria, etc. can act as inducing agents ("Th1 inducing agents"). If instead it is desired that a pAPC secrete Th2 stimulating cytokines, then other factors (e.g., factors that induce IL-4 expression or inhibit IL-12 expression) can act as inducing agents ("Th2 inducing agents"). It will be appreciated by those of ordinary skill in the art that an inducing agent is usually an adjuvant.

"Isolated": As will be clear from context, the term "isolated" means (i) separated from at least one of the components with which the isolated entity or compound is associated in nature; and/or (ii) produced by a non-natural process (e.g., synthesized in vitro or produced by a recombinant organism).

"Mast cell": As will be apparent from context, the term "mast cell" is often used herein to refer to one or more of mast cells, basophils, and other cells with IgE receptors.

"Peptide": According to the present invention, a "peptide" comprises a string of at least three amino acids linked together by peptide bonds. The term "peptide" may refer to an individual peptide or a collection of peptides. For the purposes of the present invention, peptides preferably contain only natural amino acids, although non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in a "peptide" may be modified, for example, by the addition of a chemical entity such as a carbohydrate group, a phosphate group, a farnesyl group, an isofarnesyl group, a fatty acid group, a linker for conjugation, functionalization, or other modification, etc.

"Polynucleotide" or "oligonucleotide": The terms "polynucleotide" and "oligonucleotide" refer to polymers of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyladenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, and hexose), and/or modified phosphate groups (e.g., phosphorothioates and 5'-N-phosphoramidite linkages).

"Purified": A compound is "purified" in accordance with the present invention if it is separated from substantially all other components. Preferably, a purified compound is at least about 75% pure, more preferably it is at least about 80%, 90%, 95%, 97%, 98%, or 99% pure.

"Sensitized individual": A "sensitized" individual is a human or animal who has been exposed to a given antigen and has mounted an immune response to that antigen that results in the display of one or more allergic or asthmatic symptoms when the individual is exposed to the antigen.

"Sensitized mast cell": A "sensitized" mast cell is a mast cell that has surface-bound antigen-specific IgE molecules. The term is necessarily antigen specific. That is, at any given time, a particular mast cell will be "sensitized" to certain antigens (those that are recognized by the IgE on its surface) but will not be sensitized to other antigens.

"Th1 response" and "Th2 response": Th1 and Th2 responses are well-established alternative immune system responses that are characterized by the production of different collections of cytokines and/or cofactors. For example, Th1 responses are generally associated with the production of cytokines such as IL-1β, IL-2, IL-12, IL-18, IFNα, IFNγ, TNFβ, etc.; Th2 responses are generally associated with the production of cytokines such as IL-4, IL-5, IL-10, etc. The extent of T cell subset suppression or stimulation may be determined by any available means including, for example, intra-cytoplasmic cytokine determination. In preferred embodiments of the invention, Th2 suppression is assayed, for example, by quantitation of IL-4, IL-5, and/or IL-13 in stimulated T cell culture supernatant or assessment of T cell intra-cytoplasmic (e.g., by protein staining or analysis of mRNA) IL-4, IL-5, and/or IL-13; Th1 stimulation is assayed, for example, by quantitation of IFNα, IFNγ, IL-2, IL-12, and/or IL-18 in activated T cell culture supernatant or assessment of intra-cytoplasmic levels of these cytokines.

DETAILED DESCRIPTION OF CERTAIN PREFERRED EMBODIMENTS OF THE INVENTION

The present invention unites insights from traditional Chinese medicine and modern Western medicine to formulate treatments for allergy and asthma. Traditional Chinese medicine employs herbal formulations to treat bodily ailments. In some cases, single herbs or herb derivatives are used. More commonly, however, "formulas", or specific combinations of several particular herbs, are administered. The recipes for these formulas are assembled into books known as "formularies". The original formulary, *Discussion of Cold-Induced Disorders and Miscellaneous Diseases* (Shang Han Za Bing Lun), was written at the end of the second century A.D. by Zhang Zhong-Jing. This book was later edited by Wang Shu-He, who divided it into two parts, *Discussion of Cold-Induced Disorders* (Shang Han Lun), which deals with externally-contracted diseases, and *Essentials from the Golden Cabinet* (Jin Gui Yao Lue), which is primarily concerned with internally-generated disorders (Bensky et al., *Chinese Herbal Medicine: Formulas & Strategies*. Eastland Press, 1999; incorporated herein by reference). These two books contain 374 formulas. The present invention provides a new analysis of certain of these formulas and identifies characteristics applicable to the treatment of asthma and allergic disease according to Western principles.

Several different Chinese formulas are recommended for the treatment of coughing, wheezing, shortness of breath, or other symptoms that can be associated with asthma or allergies. Few, however, have been shown in clinical or animal studies to have a demonstrable salutary effect on asthma or allergies (see, for example, Coyle et al., *Eur. J. Pharmacol.* 148:51, 1988; But et al., *Clin. Rev. Allergy Immunol.* 14:253, 1996; Hsieh et al., *Pediatr. Allergy Immunol.* 14:253, 1996; Zhang et al., *Chung. Kuo. Chung. Hsi. I. Chieh Ho. Tsa. Chih.* 17:204, 1997; Sun et al., *Chung. Kuo. Chung. Hsi. I. Chieh. Ho. Tsa. Chih.* 17:201, 1997; Zou et al. *Chung Kuo. Chung. Hsi. I. Chieh. Ho. Tsa. Chih.* 16:529, 1996; Xu et al., *Chung Kuo. Chung. Hsi. I. Chieh. Ho. Tsa. Chih.* 16:198, 1996; Chen et al., *Pharmacology and Clinical Applications of Patent Medicine and Famous Formulas*. Hong Kong: Ya Yi Publishing Company, pp. 44–92, 407, 1989; Egashira et al., *Ann. NY Acad. Sci.* 685:580, 1993; Noma et al., *Arerugi* 45:494, 1996; Toda et al., *J. Ethnopharmacol.* 24:303, 1988; Hamasaki et al., *J. Ethnopharmacol.* 56:123, 1997; Roberts et al., *J. Allergy Clin. Immunol.* 82:236, 1988; Dong et al., *Chinese J. of Integrated Traditional Chinese and Western Medicine* 318, 1989; Nyunt et al., *Arerugi* 44:503, 1995; each of which is incorporated herein by reference). The present invention identifies herbal formulations, and components thereof, that are useful in alleviating, treating, and/or preventing symptoms of allergy and/or asthma.

Herbal Formulations

The present invention provides herbal formulations that reduce allergic or asthmatic symptoms and signs including but not limited to airway hyperresponsiveness, hives, rash, puritis, watery eyes, bronchconstriction, edema, diarrhea, difficulty breathing, vasodilation, decrease in blood pressure, increased IgE levels, increased plasma histamine levels, increased numbers of goblet cells, increased Th2 cytokine levels, bronchial inflammation, anaphylaxis, and death. Preferably, the compositions demonstrate a reduction in symptoms that is at least as significant as that observed with standard treatments such as corticosteroids and antihistamines. Preferably, the reduction in symptoms occurs more quickly than is seen with standard treatments (e.g., conventional antigen immunotherapy and/or steroid treatment), is more persistent than that observed with standard treatments, and/or is more extensive than that achieved by standard treatments.

Without wishing to be bound by any particular theory, we propose that inventive herbal compositions down regulate Th2 responses, thereby leading to a reduction in allergy or asthma symptoms. In fact, particularly preferred compositions have specific effects on Th2 responses, rather than general immunosuppressive activities. For example, preferred inventive compositions when compared to immunosuppressive agents such as corticosteroids, FK506, methotrexate, and cyclosporin are more selective for the allergic or asthmatic response.

The current understanding of allergic and/or asthmatic diseases may be used to choose herbal formulations that may be further tested using standard experimental systems used in studying allergies or asthma (for example, see Examples below). Formulations may be chosen which are known to reduce sneezing, water eyes, itching, diarrhea, wheezing, bronchoconstriction, hives, etc, as such symptoms can be associated with allergies and/or asthma The chosen formulation may be assessed in animal models of allergy or asthma, or in in vitro models of allergy or asthma. From the hundreds of herbals formulas known in Eastern medicine, the present invention teaches methods of choosing potential anti-allergy or anti-asthma therapies and testing the chosen therapies for efficacy in treating or preventing allergies or asthma. As described in the Examples below, the present invention also demonstrates use of these methods, and defines certain particularly useful compositions.

For example, according to the present invention, one preferred formulation is Wu Mei Wan, a Chinese medicinal formula. Wu Mei Wan has been used in the treatment of parasitic diseases in Chinese medicine and has also been used to treat endometriosis. Particularly preferred inventive herbal compositions include at least the herbs Fructus Pruni Mume (Wu Mei), Pericarpium Zanthoxyli Bungeanum (Chuan Jia), *Herba cum* Radice Asari (Xi Xin), Rhizoma Coptidis (Huang Lian), Cortex Phellodendri (Huang Bai), Rhizoma Zingiberis Officinalis (Gan Jiang), Radix Lateralis Aconiti Carmichaeli Praeparata (Fu Zi), Ramulus Cinna-momi Cassiae (Gui Zhi), Radix Ginseng (Ren Shen), and Radix Angelicae Sinensis (Dang gui). If the weight of Pericarpium Zanthoxyli Bungeanum is defined as approximately 1, the ratio of Pericarpium Zanthoxyli Bungeanum to Fructus Pruni Mume is from approximately 10 to approximately 16, to *Herba cum* Radice Asari is approximately 1, to Rhizoma Coptidis is from approximately 4 to approximately 6, to Cortex Phellodendri is from approximately 3 to approximately 4, to Rhizomo Zingiberis Officinalis is from approximately 3 to approximately 4, to Radix Lateralis Aconiti Carmichaeli Praeparata is approximately 2, to *Ramulus cinnamomi* Cassiae is approximately 2, to *Radix ginseng* is from approximately 3 to approximately 4, and to Radix Angleicae Sinensis is from approximately 2 to approximately 3. In certain particularly preferred embodiments, the inventive herbal compositions also include the herb *Ganoderma lucidum* (ling Zhi). The ratio of the weight of Pericarpium Zanthoxyli Bungeanum to the weight of *Ganoderma lucidum* is preferably approximately 2. In other preferred embodiments, Radix Codonopsis Pilosulae is substituted for Radix Ginseng. One particularly preferred inventive herbal formulation is the particular formulation of WMW, as described in Table 1. Other preferred compositions are the formulation of WMW and ZN, as described in Table 2.

TABLE 1

WU MEI WAN FORMULATION

| PLANT NAME | CHINESE NAME | AMOUNT |
| --- | --- | --- |
| Fructus Prunus Mume | Wu Mei | 24–30 g |
| Pericarpium Zanthoxylum Bungeanum | Chuan Jiao | 1.5–3 g |
| Herba cum Radice Asari | Xi Xin | 1.5–3 g |
| Rhizoma Coptidis | Huang Lian | 9–12 g |
| Cortex Phellodendri | Huang Bai | 6–9 g |
| Rhizoma Zingiberi Officinale | Gan Jiang | 6–9 g |
| Radix Lateralis Aconiti Carmichaeli Praeparata | Fu Zi | 3–6 g |
| Ramulus Cinnamomi Cassiae | Gui Zhi | 3–6 g |
| Radix Ginseng | Ren Shen | 6–9 g |
| Radix Angelica Sinensis | Dang Gui | 6–9 g |

TABLE 2

WU MEI WAN + LZ FORMULATION

| PLANT NAME | CHINESE NAME | AMOUNT |
| --- | --- | --- |
| Fructus Prunus Mume | Wu Mei | 24–30 g |
| Pericarpium Zanthoxylum Bungeanum | Chuan Jiao | 1.5–3 g |
| Herba cum Radice Asari | Xi Xin | 1.5–3 g |
| Rhizoma Coptidis | Huang Lian | 9–12 g |
| Cortex Phellodendri | Huang Bai | 6–9 g |
| Rhizoma Zingiber Officinale | Gan Jiang | 6–9 g |
| Radix Lateralis Aconiti Carmichaeli Praeparata | Fu Zi | 3–6 g |
| Ramulus Cinnamomi Cassiae | Gui Zhi | 3–6 g |
| Radix Ginseng | Ren Shen | 6–9 g |
| Radix Angelica Sinensis | Dang Gui | 6–9 g |
| Ganoderma lucidum | Ling Zhi | 3–6 g |

Figure 13:
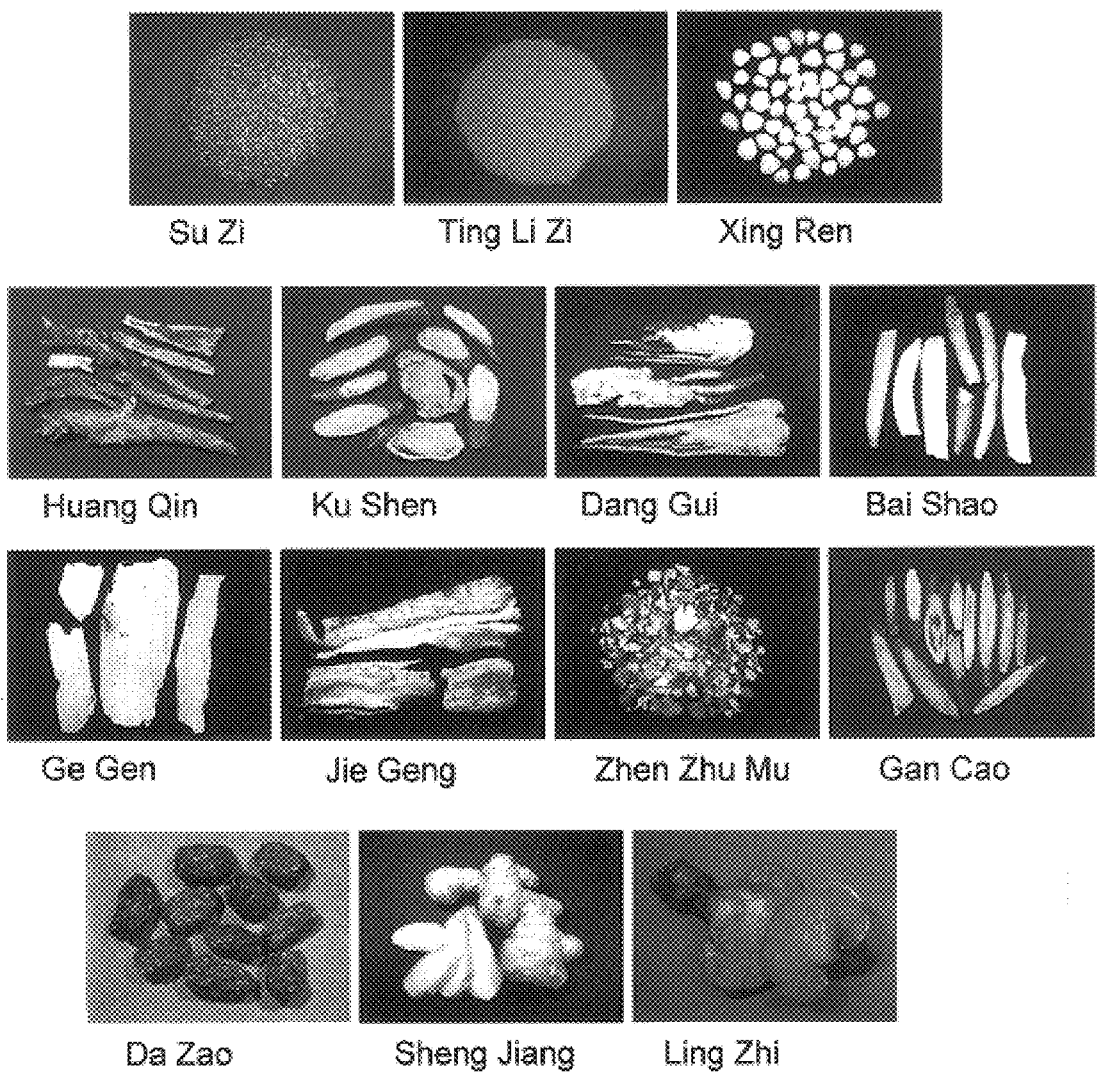
FIG. 13 shows photographs of the herbs used in the herbal formulation MSSM-002.

Other particularly preferred inventive herbal compositions include at least the herbs Huang Qing, Ku Sen, and Ling Zhi. In certain preferred embodiments, these herbs are present in relative amounts approximating 3:3:2 ratios. Alternatively or additionally, preferred compositions may include one or more of Dong Gui and Ge Gen. Relative amounts of these herbs, in certain particularly preferred compositions, will approximate the levels of Huang Qing and/or Ku Sen. Other preferred embodiments may further, or alternatively, include Su Zi, preferably at a level approximating that of Huang Qing and/or Ku Sen. One particularly preferred inventive herbal formulation is MSSM-002 (see Table 3 and FIG. 13).

TABLE 3

MSSM-02 FORMULATION

| CHINESE NAME | PLANT NAME | AMOUNT |
|---|---|---|
| Su Zi | Perillae frutescens | 9 g |
| Ting li zi | Descurainia sophia | 9 g |
| Xing reni | Prunus armeniaca | 9 g |
| Huang Qing | Scutellaria baicalensis | 9 g |
| Ku Shen | Sophora flavescens | 9 g |
| Dang Gui | Angelica sinensis | 9 g |
| Bai Shao | Paeonia lactiflora | 9 g |
| Ge Gen | Peuraria lobata | 9 g |
| Jie Gen | Platycodon grandiflorum | 6 g |
| Zhen Zhu Mu | Pteria margaratiferae | 6 g |
| Ling Zhi | Ganoderma lucidum | 6 g |
| Gan Cao | Glycyrrhiza uralensis | 6 g |
| Da Zao | Ziziphus jujuba | 5 pieces |
| Shen Jiang | Frash Zingiber officianale | 6 g |

Another particularly preferred composition is MSSM-0001 (see Table 4).

TABLE 4

MSSM-001 FORMULATION

| CHINESE NAME | PLANT NAME |
|---|---|
| Su Zi | Perillae frutescens |
| Ting li Zi | Descurainia sophia |
| Lai Fu Zi | Raphanus sativus L. |
| Sang Bai Pi | Marus alba L. |
| Xing ren | Prunus armeniaca |
| Huang Qin | Scutellaria baicalensis |
| Gan Cao | Glycyrrhiza uralensis |
| Da Zao | Ziziphus jujuba |
| Zi Wan | Aster tataricus |
| Zhen Zhu Mu | Pteria margaritaferae |
| Kuan Don Hua | Tussilago farfara |

Inventive herbal formulations may be prepared in any manner that preserves the desired biological activity of the formulation. Examples of possible preparations include decoctions, aqueous extracts, organic solvent (e.g., alcohol, ethyl acetate) extracts, and dry powder. In one particularly preferred embodiment, the herbs are dried and ground, and the resulting powder is processed into pill form.

Herbs for use in the inventive compositions will generally be provided in their natural, herbal form. The herbs may be harvested from any location at any time of the year. Preferably, the herb has the active components at concentrations sufficient to treat allergic symptoms, treat asthmatic symptoms, or prevent an allergic response. More preferably, the herbs are harvested in a manner which maximizes the efficacy of the herbal formulation. In a particularly preferred embodiment, an herb may be harvested from a specific geographic location or during a particular time of the year to maximize the amount of active ingredient found in the herb. To give but one example, the herb Ganoderma lucidum may preferably be harvested in the Dooryoon Mountains located in the South Cholla Province of Korea.

To one of skill in this art, it will be appreciated that the substrate on which the herbs are growing can be important in selecting the herbs for harvest. For example, the fungi Ganoderma lucidum growing on oak wood may be found to have more of the active ingredient than Ganoderma lucidum growing on other woods. As would be appreciated by one of skill in this art, the soil in which the herbs are growing may also contribute to the concentration of the active ingredient in the harvested herb. In other preferred embodiments, the herbs may be artificially cultivated. For an example of cultivating Ganoderma lucidum, please see U.S. Pat. No. 4,472,907, issued Sep. 25, 1984, incorporated herein by reference.

The herbs for the formulations may also be selected based on any number of criteria including, but not limited to, appearance (e.g., color, texture, etc.), smell, feel, HPLC "finger printing", chromatographic (e.g., HPLC, TLC,GC) fingerprint profiles, presence of a "marker" constituent, etc. In a particularly preferred embodiment, the herbal formulation is prepared by following the FDA's "Guidance for Industry Botanical Products". The herbs may also be checked for the presence of pesticide residues, heavy metal content, etc. to ensure the safety of the final product.

As is appreciated by those skilled in this art, a variety of techniques are well known in the art for extracting, isolating, and/or purifying individual active components of the particular herbs. The present invention encompasses both the identification of such active components as described herein and the incorporation of such components into inventive compositions as described herein.

Purification of Active Components

Individual active components of the herbs or herbal formulations may be identified as described herein and may be isolated and/or purified using any techniques known in the art. The active component may be purified from the herb itself in any form (e.g., fruit, seed, spore, flower, leaves, stalk, root, rhizomes, etc.), the culture media of the organism, the decoction of WMW, the decoction of WMW+LZ, etc. Various techniques that may be employed in the purification include filtration, selective precipitation, extraction with organic solvents, extraction with aqueous solvents, column chromatography, high performance liquid chromatography (HPLC), etc. (Zubrick, *The Organic Chem Lab Survival Manual Third Edition* New York: John Wiley & Sons, Inc., 1992; Scopes *Protein Purification Principles and Practice* (2nd ed.), New York: Springer-Verlag, 1987; each of which is incorporated herein by reference). As would be appreciated by one of skill in the art, the active components may be proteins, peptides, nucleic acids, natural products, terpenes, alkaloids, proteoglycans, polysaccharides, lipids, triglycerides, etc., and therefore, the purification procedure would depend on the nature of the component being purified.

Fractions from a purification step may be assayed for the desired biological activity to determine which of the fractions contain the desired active component. In a preferred embodiment, the allergic mouse model as described in U.S. patent application Ser. No. 09/518,346, filed Mar. 3, 2000, incorporated herein by reference, is used as the assay for determining the presence of the desired active component. In animal models, administration of the herb or active component may lead to at least a 10% decrease in IgE levels, more preferably at least a 50% decrease, and most preferably at least a 75% decrease. In another particularly preferred embodiment, antigen-specific IgE levels are less than 2000 ng/ml after administration of the inventive formulation, more preferably less than 1500 ng/ml, and most preferably less than 1000 ng/ml. In other preferred embodiments, cell culture based assays or in vitro assays are used (e.g., basophil histamine release assays. For example, in the basophil histamine release assay the herb or active component may lead to at least a 25% decrease in histamine levels; more preferably at least a 50% decrease; and most preferably at least a 75% decrease. As appreciated by one of skill in this art, the desired biological activity may not lie in one fraction by itself but may stem from a combination of active components so various combinations of fractions from each purification step may need to be evaluated in the assay system to identify the active components.

In yet other preferred embodiments, the presence and purity of the active compound is assessed by chemical methods including nuclear magnetic spectroscopy (NMR), mass spectroscopy, infrared spectroscopy (IR), ultra-violet visible spectroscopy, elemental analysis, polarimetry, refractometry, etc.

In the final composition to be delivered to the individual, the purified active component is preferably greater than 50% pure. In a preferred embodiment, the active component is greater than 75% pure, and more preferably greater than 90% pure. In a particularly preferred embodiment, the active component is greater than 95% pure.

Other Components

As will be appreciated by those of ordinary skill in the art, the inventive herbal formulations may be desirably combined with one or more additional components, in a single composition or in more than one composition, to more effectively treat allergic or asthmatic conditions. For example, inventive herbal compositions may be combined with one or more adjuvants, cytokines, or encapsulating materials as discussed more fully below. Additionally, inventive herbal compositions may be combined with other known allergy or asthma treatments such as, for example, general immunosuppressants (e.g., corticosteroids), antihistamines, cromolyn sodium, traditional immunotherapy, rush immunotherapy, etc.

ADJUVANTS

A variety of compounds are known in the art to have specific or general immunostimulatory effects. Such compositions are commonly referred to as "adjuvants". A large number of adjuvant compounds is known; a useful compendium of many such compounds is prepared by the National Institutes of Health and can be found on the world wide web (http:/www.niavd.nih.gov/daids/vaccine/pdt/compendium/pdf, incorporated herein by reference; see also Allison *Dev. Biol. Stand.* 92:3–11, 1998; Unkeless et al. *Annu. Rev. Immunol.* 6:251–281, 1998; Phillips et al. *Vaccine* 10:151–158,1992; each of which is incorporated herein by reference). Preferred adjuvants are characterized by an ability to stimulate Th1 responses preferentially over Th2 responses and/or to down-regulate Th2 responses. In fact, in certain preferred embodiments of the invention, adjuvants that are known to stimulate Th2 responses are avoided. Particularly preferred adjuvants include, for example, preparations (including heat-killed samples, extracts, partially purified isolates, or any other preparation of a microorganism or microorganism component sufficient to display adjuvant activity) of microorganisms such as *Listeria monocytogenes* or others (e.g., Bacille Calmette-Guerin [BCG], Corynebacterium species, Mycobacterium species, Rhodococcus species, Eubacteria species, Bortadella species, and Nocardia species), and preparations of nucleic acids that include unmethylated CpG motifs (see, for example, U.S. Pat. No. 5,830,877; and published PCT applications WO 96/02555, WO 98/18810, WO 98/16247, and WO 98/40100, each of which is incorporated herein by reference). Other preferred adjuvants reported to induce Th1-type responses and not Th2-type responses include, for example, Aviridine (N,N-dioctadecyl-N'N'-bis (2-hydroxyethyl) propanediamine) and CRL 1005.

In some embodiments of the invention, the adjuvant is associated (covalently or non-covalently, directly or indirectly) with the herbal formulation so that adjuvant and formulation can be delivered substantially simultaneously to an individual, optionally in the context of a single composition. In other embodiments, the adjuvant is provided separately. Separate adjuvant may be administered prior to, simultaneously with, or subsequent to herbal formulation administration. In certain preferred embodiments of the invention, a separate adjuvant composition is provided that can be utilized with multiple different herbal formulations.

Where adjuvant and formulation are provided together, any association sufficient to achieve the desired immunomodulatory effects may be employed.

CYTOKINES AND INDUCING AGENTS

In some cases, in will be desirable to provide inventive herbal formulations in combination with one or more cytokines or inducing agents, preferably to promote and/or reflect a reduction in Th2 responses and/or an increase in Th1 responses to the relevant antigen. In certain preferred embodiments of the invention, herbal formulations are provided in combination with one or more Th1 stimulating cytokines (e.g., IL-12, IL-2, IL-18, IL-1β or fragments thereof, IFNα, and/or IFNγ, etc.) and/or one or more Th1 inducing agents (e.g., factors such as LPS, CD40, CD40 ligand, BCGs, oligonucleotides containing CpG motifs, TNFα, and microbial extracts such as preparations of *Staphylococcus aureus*, heat killed Listeria, etc.). Alternatively or additionally, the herbal formulations may be provided in combination with one or more Th1 cytokines (e.g., IL-10, IL-2, IL-12, IL-18, IFNα, IFNγ, TNFβ, etc.).

STANDARD THERAPIES

Inventive herbal formulations may be administered to a subject in combination with one or more other therapeutic treatments. For example, corticosteroid administration is an established and accepted treatment for asthma; inventive herbal formulations may desirably be administered in combination with standard or reduced corticosteroid treatments, whether inhaled or systemic. In the case of treating individuals with allergies, the inventive composition may be administered in combination with accepted treatments for allergies including, but not limited to, anti-histamines, nonsteroidal anti-inflammatory drugs, decongestants, and cromolyn sodium. The inventive herbal formulations may also be administered in combination with standard immunotherapy or rush immunotherapy. Immunotherapies are typically administered in order to induce tolerance in a sensitized individual (for a more detailed description of immuotherapy, please see U.S. Provisional Patent Application, U.S. Ser. No. 60/213,765, filed Jun. 23, 2000; incorporated herein by reference).

ENCAPSULATION

Inventive herbal formulations may be administered, whether alone or in combination with one or more other agents or compounds, in the context of an encapsulated system. A variety of encapsulation systems are known in the art (see, for example, discussions in U.S. Ser. No. 60/169,330, filed Dec. 6, 1999, and incorporated herein by reference); any such system may be employed in accordance with the present invention. In certain preferred embodiments of the invention, the encapsulation material itself may offer adjuvant activity. Also, preferred encapsulation systems may desirably be associated with one or more targeting agents that facilitate delivery of the inventive compositions to relevant sites (e.g., mucosal membranes).

PHARMACEUTICAL EXCIPIENTS AND CARRIERS

Pharmaceutical compositions for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such as propylene glycol; esters, such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Preferably, the inventive pharmaceutical compositions comprising herbal formulations are administered orally. However, other routes of administration may also be utilized. For example, in some embodiments of the invention, pharmaceutical compositions may be delivered to mucous membranes, for example, by inhalation or injection. In general, inventive pharmaceutical compositions can be administered to humans and/or to other animals, orally, rectally, parenterally, intracisternally, intravaginally, intraperitoneally, topically (as by powders, ointments, or drops), bucally, or as an oral or nasal spray.

Preferred oral forms for administration of inventive herbal formulations are described in standard herbal remedies texts (see, for example, Bensky et al., *Chinese Herbal Medicine: Formulas & Strategies* Eastland Press, 1999; incorporated herein by reference). However, other forms may alternatively be useful. Techniques for preparing alternative forms of pharmaceutical compositions are well known in the art. Several non-limiting examples are discussed, for example, in U.S. patent application Ser. No. 09/518,246, entitled "Animal Model for Allergies", filed Mar. 3, 2000, and incorporated herein by reference.

Identification and Characterization of Inventive Herbal Formulations

The effects of inventive herbal formulation compositions may be studied in humans or in any available in vivo or in vitro model system. Animal models are particularly useful for the identification, characterization, and analysis of a particular composition's effects. Ideally, a model system should reflect closely at least some aspect of the disease pathology in man (or in another organism to which an inventive composition is to be administered for the treatment of asthma or allergy), should be reliable and reproducible, should allow objective measurements of one or more physiologically-relevant parameters, should respond to one or more known therapeutic agents in a manner similar to that observed in man (or the suffering organism), and/or should offer a large number of reagents with which the immune system can be analyzed.

A variety of animal models, including those in guinea pigs, rabbits, sheep, dogs, monkeys, and mice have been developed that can usefully be employed to characterize herbal compositions of the present invention (see, for example, Kay (ed.) *Allergy and Allergic Diseases Blackwell Science*, Ltd., Oxford. pp. 1037–1110, 1997; Ermel et al. "The Atopic Dog: A Model for Food Allergy" *Lab. Animal Science* 47(1):40–49, 1997; Li et al. "A Murine Model of IgE-Mediated Cow's Milk Hypersensitivity" *J. Allergy Clin. Immunol.* 103(2 Pt 1):206–214, 1999; Li et al. "Strain-Dependent Induction of Allergic Sensitization Caused by Peanut Allergen DNA Immunization in Mice" *J. Immunol.* 162(5):3045–3054, 1999; McCaskill et al. "Anaphylaxis Following Intranasal Challenge of Mice Sensitized with Ovalbumin" *Immunology* 51:669–677, 1984; U.S. patent application Ser. No. 09/518,246, filed Mar. 3, 2000; each of which is incorporated herein by reference).

To give but one example, guinea pigs were one of the earliest asthmatic model systems because of the ease with which they can be sensitized to foreign antigens, and the similarity of the histological characteristics observed in antigen-sensitized guinea pig lungs as compared with asthmatic humans lungs (Kallos et al., *Int. Arch. Allergy Appl. Immunol.* 73:77, 1985; incorporated herein by reference). Antigen challenges to sensitized guinea pigs can provoke both early and late-phase airway responses, and the roles of IL-5 and eotaxin in asthmatic reactions have been extensively characterized in this model (Rothenberg et al., *J. Exp. Med.* 181:1211, 1995; incorporated herein by reference). However, the guinea pig may not be an ideal model since several compounds that have shown therapeutic efficacy in the guinea pig have proven not to be useful in humans, and vice versa (see, for example, Mishall et al., in *Allergy and Allergic Diseases* (Kay, Ed.) Blackwell Science, Ltd., Oxford, pp. 1037–1110, 1997; incorporated herein by reference).

Mouse models are particularly preferred for use in the characterization of inventive herbal compositions for the treatment of asthma and allergy. The immune system of the mouse mimics the human immune system more closely than does that of other rodents. Furthermore, the mouse immune system has been well characterized through the close analysis of highly inbred strains. In addition, a wide variety of immunological reagents have been developed for use in the analysis of murine immunological reactions, and increasing numbers of useful knock-out and transgenic strains (including, for example, IL-4 deficient mice [Kopf et al., *Nature* 362:245, 1993, incorporated herein by reference], IgE-deficient mice [Oettgen et al., *Nature* 7370:367, 1994, incorporated herein by reference], etc.) have been created.

Those of ordinary skill in the art will recognize that the particular mouse strain or route of administration of sensitizing antigen may not be critical in developing a preferred mouse model system for use in characterizing inventive herbal compositions. For example, Renz et al. have described a BALB/c mouse sensitized with aerosolized ovalbumin over a 10-day period (Renz et al., *J. Exp. Med.* 177:1175, 1993; incorporated herein by reference). These mice show elevated levels of ovalbumin-specific IgE and infiltration of eosinophils into the airway following bronchial challenge. Wills-Karp et al. have described an asthmatic A/J mouse model sensitized by intraperitoneal administration of antigen, followed by intratracheal challenge (Gavett et al., *Am. J. Respir. Cell Mol. Biol.* 10:587, 1994; Keane-Myers et al., *J. Immunol.* 161:919, 1998; Wills-Karp et al., *Science* 282:2258, 1998; Grunig et al., *Science* 282:2261, 1998; each of which is incorporated herein by reference). Preferably, the sensitizing antigen is administered to the animal via the same route the animal would encounter the allergen in nature (e.g., oral for food allergens, IV or parenteral for venoms, inhaled for pollens or dust allergens, intradermal for latex). In a particularly preferred embodiment, the mouse is sensitized to the allergen using alum as an adjuvant (see Example 1 below for details).

We herein describe (see Example 1) a conalbumin-allergic AKR/J mouse in which IgE significantly increased following intraperitoneal sensitization, and BALF eosinophils were increased at 12 hour and peaked at 72 hours following i.t. challenge. This model closely mimics the late phase response of human asthma and is particularly preferred for use in the characterization of inventive herbal compositions (Li et al., *J. Immunol.* 160:1378, 1998; incorporated herein by reference). Those of ordinary skill in the art will appreciate that any of a variety of other mouse systems can be developed and/or utilized in accordance with the present invention.

A mouse model using alum as the adjuvant in sensitizing the mouse may also be used in characterizing the herbal compositions of the present invention. The alum mouse is a well-characterized animal model used in studying allergies (Levine et al. "Effect of combinations of inbred strain, antigen, and antigen dose on immune responsiveness and reagin production in the mouse. A potential mouse model for immune aspects of human atopic allergy" *Int. Arch. Allergy Appl. Immunol.* 39(2–3):156–171, 1970; incorporated herein by reference).

One in vitro model useful in characterizing inventive herbal formulations is the basophil histamine release assay. One of the way in which inventive herbal formulations may be characterized is by their ability to inhibit histamine release in isolated basophils that are contacted with antigen. Example 5 describes one procedure by which such basophil histamine release is assayed; those of ordinary skill in the art will recognize that various modifications and alterations of this precise procedure can be made without departing from the spirit or scope of the present invention. Basophil histamine release assays are well established in the art (to give but a few examples, see Counsell et al., *J. Allergy Clin. Immunol.* 98:884, 1996; Haselden et al., *J. Exp. Med.* 189:1885, 1999; incorporated herein by reference).

Uses

The inventive compositions may be employed to treat existing asthmatic symptoms (i.e., to reduce the severity, intensity, and/or duration of such symptoms). In such cases, the compositions are administered to an individual after asthmatic symptoms have developed.

Alternatively or additionally, the composition may be used to prevent or delay the onset of symptoms in an individual who has previously suffered asthmatic attacks, or to reduce the severity, intensity, or duration of subsequently-developed symptoms. Preferably, one or more antigens has been identified that is known to have induced, or at least to be correlated with, the onset of prior asthmatic attacks. In such cases, the inventive compositions are administered either prior to the onset of symptoms after a subsequent encounter with the antigen, or prior to the encounter.

The inventive compositions may also be administered prior to the development of asthmatic/allergic sensitivity to a particular antigen. Preferably, the compositions are administered substantially concurrently with exposure to an antigen that has not previously been associated with an asthmatic and/or allergic reaction in the individual. Without wishing to be bound by any particular theory, we propose that the inventive compositions may encourage the individual to adopt a Th1 response to the antigen. Given the mutually inhibitory aspects of Th1 and Th2 responses, the initial development of a Th1 response may inhibit, delay, or prevent subsequent Th1 reactions that could otherwise result in asthmatic and/or allergic symptoms.

These and other aspects of the present invention will be further appreciated upon consideration of the following Examples, which are intended to illustrate certain particular embodiments of the invention but are not intended to limit its scope, as defined by the claims.

EXAMPLES

Example 1

Reduction of Asthmatic Symptoms in a Murine Model Using Herbal Compositions MSSM-001 and MSSM-002

Introduction

We tested the effects of two different herbal compositions, MSSM-001 and MSSM-002, on a murine model of allergic asthma. We found that MSSM-001 reduced Ag-induced airway hyperresponsiveness (AHR), IgE levels, and IL-5 production. We have evaluated the effect of MSSM-002 on AHR, pulmonary inflammation, IgE production, and cytokine profiles, and have compared these effects to those observed with the potent corticosteroid dexamethasone (Dex). We have found MSSM-002 to be even more effective than MSSM-001, and in particular have found that its AHR suppression is equivalent to Dex.

Materials and Methods

MICE AND REAGENTS: Male AKR/J mice (6 weeks old) purchased from the Jackson Laboratory (Bar Harbor, Me.) were maintained in the animal facility at Mount Sinai School of Medicine. Standard guidelines for lab animal care were followed (Fahy et al. "The effect of an anti-IgE monoclonal antibody on the early- and late-phase response to allergen inhalation in asthmatic subjects [see comments]" *Am. J. Respir. Crit. Care Med.* 155:1828–1834, 1997; incorporated herein by reference). Conalbumin (CA), Concanavalin A (Con A), Dex, and dinitrophenyl conjugated with albumin (DNP-albumin) were purchased from Sigma (St. Louis, Mo.). Antibodies for ELISAs were purchased from the Binding Site Inc. and PharMingen (San Diego, Calif.). Anti-DNP IgE and IgG2a were purchased from Accurate Scientific Inc. (New York).

COMPOSITION FORMULATION: Both MSSM-001 and MSSM-002 were formulated according to the standard preparation protocol for decoctions (Bensky et al., *Chinese Herbal Medicine: Formulas & Strategies*. Eastland Press, 1999). MSSM-001 was based on a preparation used by one of the present inventors to treat asthma and bronchitis in children in the Pediatric Department of the China Japan Friendship Hospital, which included the components listed in Table 4 above. MSSM-002 was formulated according to Table 3 above.

ANTIGEN (AG)-SENSITIZATION/CHALLENGE AND MSSM-002 TREATMENT: Mice (AKR 6 Week old, n 8) were injected twice (on days 0 and 7) i.p. with CA (200 $\mu$g) in alum (2 mg) followed by 3 i.t administrations (on days 14, 24, and 34). Mice were treated twice daily with MSSM-002 (270 mg/mouse) intragastrically (ig) starting 24 hours after the first i.t. administration for 18 consecutive days. Intragastric feeding was performed by means of a 25-gauge stainless steel blunt feeding needle (Fine Science Tool Inc, CA, USA). The dose of herbal formula used in this study was based on the equivalent effective dose by weight prescribed for humans (Xiu "The experimental method of pharmacology" Beijing: The People's Public Health Publisher 985–924, 1986; incorporated herein by reference). Dexamethasone-treated mice received 0.5 mg/kg/day i.p. daily, as described previously (De et al. "Effect of dexamethasone and endogenous corticosterone on airway hyperresponsiveness and eosinophilia in the mouse" *Br. J. Pharmacol.* 119:1484–1490, 1996; incorporated herein by reference). Sham treated mice received saline ig daily. Naive mice served as additional controls.

MEASUREMENT OF LATE-PHASE AIRWAY RESPONSES: Three days after the last i.t. Ag challenge, airway responsiveness was determined by measuring airway pressure changes following iv acetylcholine injection as previously described (Li et al. "Induction of pulmonary allergic responses by antigen-specific Th2 cells" *J. Immunol.* 160:1378–1384, 1998; Li et al. "Mucosal IFN-gamrna gene transfer inhibits pulmonary allergic responses in mice" *J. Immunol.* 157:3216–3219, 1996; Levitt et al. "Expression of airway hyperreactivity to acetylcholine as a simple autosomal recessive trait in mice" *FASEB J.* 2:2605–2608, 1988; each of which is incorporated herein by reference). Mice were anesthetized with sodium pentobarbital (80 mg/kg) and ventilated via a tracheal cannula (18 gauge) at the rate of 120 breaths/minute and a constant tidal volume of air (0.2 ml) with RSP1002 Pressure Controlled Respirator System (Kent Scientific Corporation, CT). Muscle paralysis was induced by iv injection of decamethonium bromide (25 mg/kg). Airway pressure was measured with a pressure transducer via a port in the trachea. Two minutes after establishing a stable airway pressure recording, acetylcholine was injected iv (50 µg/kg). The airway pressure changes were viewed and recorded, using the VENTP software respiratory data acquisition system (Kent Scientific Corporation, CT). The time-integrated changes in peak airway pressure referred to as the airway pressure-time index (APTI; cm $H_2O$ per second) was calculated and served as the measurements of airway responsiveness.

BALF PREPARATION AND CELL DIFFERENTIAL COUNTS: Following airway response measurements, mice were sacrificed, and the lungs lavaged with 1.0 ml of ice-cold HBSS (without magnesium or calcium), and the BALF collected into chilled tubes and centrifuged at 1000×g for 10 min. at 4° C. Cell pellets were re-suspended in 0.5 ml of HBSS. The total number of BALF cells were counted by using a hemocytometer. For differential counts, cytospin slides were prepared ($2\times10^4$ cells/slide, Shandon Scientific, Pittsburgh, Pa.) and stained with Diff-Quik Stain Set (Dade Diagnostics of P.R. Inc. Aguada, PR). Differential counts of BALF cells were determined by microscopic evaluation of five hundred cells per slide.

MEASUREMENT OF SERUM CA SPECIFIC ANTIBODIES: Blood was obtained from each group of mice immediately following APTI measurements. After centrifugation, the sera were collected and stored at −80° C. CA-specific IgE levels were measured by ELISA as described previously (Li et al. "Induction of pulmonary allergic responses by antigen-specific Th2 cells" *J. Immunol.* 160:1378–1384, 1998; incorporated herein by reference).

For measurement of CA-specific IgG2a, plates were coated with CA and then were blocked and washed as above. Samples (1:50 dilution) were added to the plates and incubated overnight at 4° C. Plates were washed, and biotinylated rat anti-mouse IgG2a monoclonal antibodies were added. Plates were incubated for an additional 45 minutes at RT. After washing, avidin-peroxidase (Sigma, 1:1000 dilution) was added for an additional 15 minutes at RT. After eight washings, the reactions were developed with ABTS (KPL) for 30 min. at RT and read at 405 nm.

Levels of antigen-specific IgE and IgG2a were calculated by comparison with a reference curve generated by using mouse monoclonal antibodies, anti-DNP IgE or IgG2 (Accurate Scientific Inc., NY, USA), as described previously (Li et al. "Induction of pulmonary allergic responses by antigen-specific Th2 cells" *J. Immunol.* 160:1378–1384, 1998; incorporated herein by reference). Briefly, DNP-albumin was coated at the same concentration as CA. After overnight incubation at 4° C., the plates were washed and blocked as described above. Ten serial 1:2 dilutions of mouse anti-DNP IgE or IgG2a antibodies starting from 1000 ng/ml were added. Thereafter all the steps were performed in a similar manner as above. All analyses were performed in duplicate and coefficient of variation (CV)>15% repeated to ensure a high degree of precision.

Cell culture and quantification of cytokines: Immediately following APTI measurement, spleen cells were isolated and suspended in complete culture medium (RPMI 1640 containing 10% fetal bovine serum, 1% penicillin/streptomycin, and 1% glutamine). Cells ($4\times10^6$/ml/well) were cultured in 24 well plates in the presence or absence of CA (50 µg/ml) or Con A (2 µg/ml). Supernatants were collected after 72-hour culture.

Levels of IL-4, IL-5, IL-13, and IFN-γ in spleen culture supernatants were determined by ELISA according to the manufacturer's instructions (PharMingen, San Diego), as previously described (Li et al. "Induction of pulmonary allergic responses by antigen-specific Th2 cells" *J. Immunol.* 160:1378–1384, 1998; incorporated herein by reference).

STATISTICAL ANALYSIS: Data were expressed as mean±SEM. Statistical analysis was performed using ANOVA for comparing more than two groups. The Student t-test was used for comparison between two groups. A p value<0.05 was considered statistically significant. All statistical analyses were performed using SigmaStat software (SPSS Inc., Chicago, Ill.).

Results

EFFECT OF MSSM-002 ON AG-INDUCED AHR: Three days following the last i.t. antigen challenge, AHR was determined by measuring the airway pressure change following acetylcholine (Ach) challenge, and the results were expressed as APTI. Consistent with our previous findings in this model (Li et al. "Mucosal IFN-gamma gene transfer inhibits pulmonary allergic responses in mice" *J. Immunol.* 157:3216–3219, 1996; incorporated herein by reference), APTI levels in sham treated, Ag-sensitized/challenged mice were significantly higher than those in normal controls (FIG. 1, p=0.00004 vs. saline), indicating the induction of AHR. APTI levels, however, were reduced by more than 50% in the MSSM-002 and Dex treated groups compared to sham treated group (p=0.0001; p=0.0035 vs. saline respectively). There was no significant difference between APTI levels in the MSSM-002, Dex, and normal control groups (p=0.59) These results demonstrated that MSSM-002, like Dex, virtually eliminated AHR.

Figure 2A:
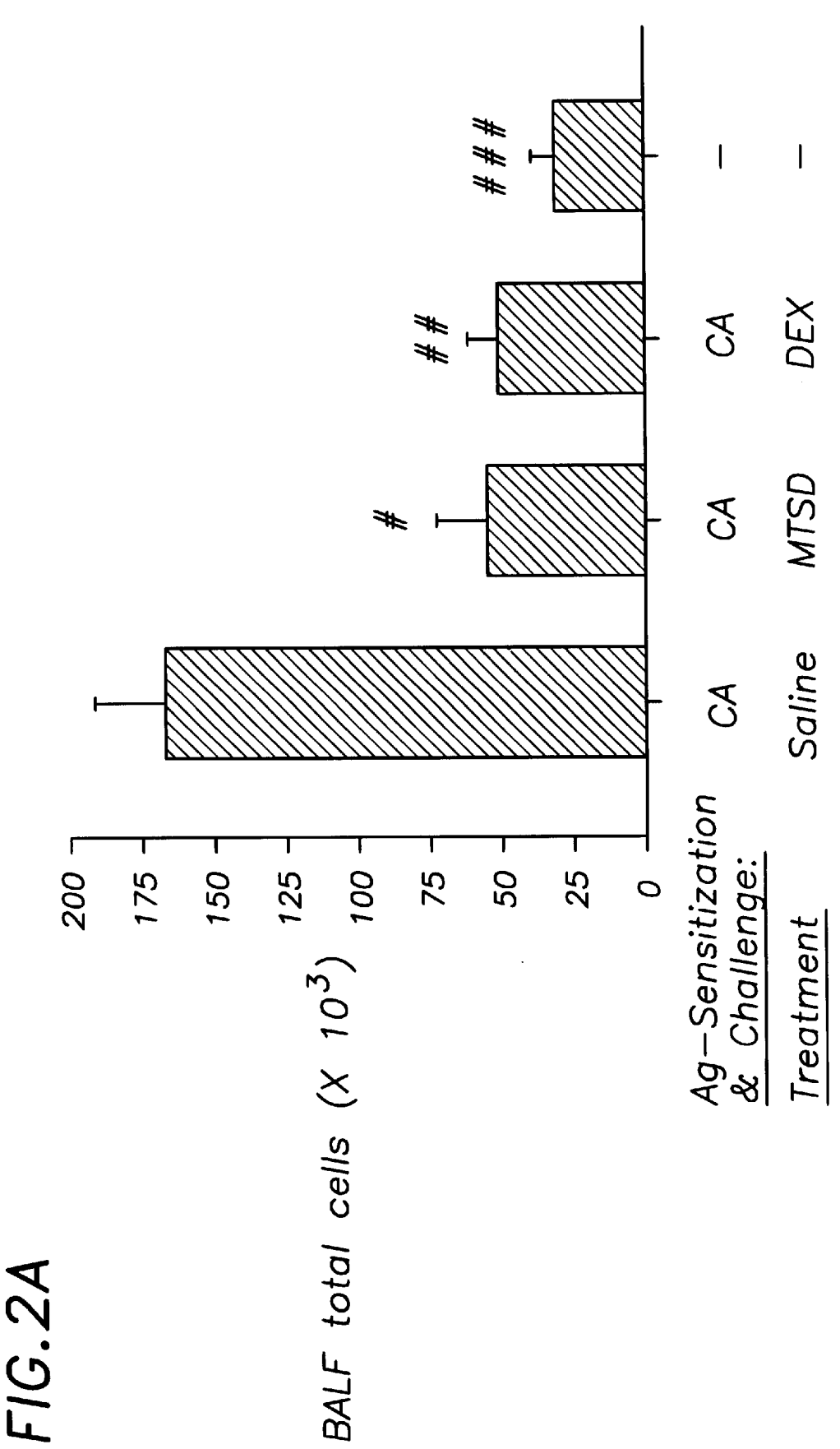
FIG. 2 shows the effect of MSSM-002 administration on antigen-induced pulmonary inflammation in a murine asthma model. Following airway response measurements, mice (n greater than or equal to 8) were sacrificed, and the lungs were lavaged. (A) shows BALF total cells. Results were expressed as mean±SEM. #, $p<0.003$; ##, $p<0.002$ vs. saline. (B) shows percent of BALF eosinophils. Results were expressed as mean±SEM. #, $p<0.0001$; ##, $p<0.003$ vs. saline.
Figure 2B:
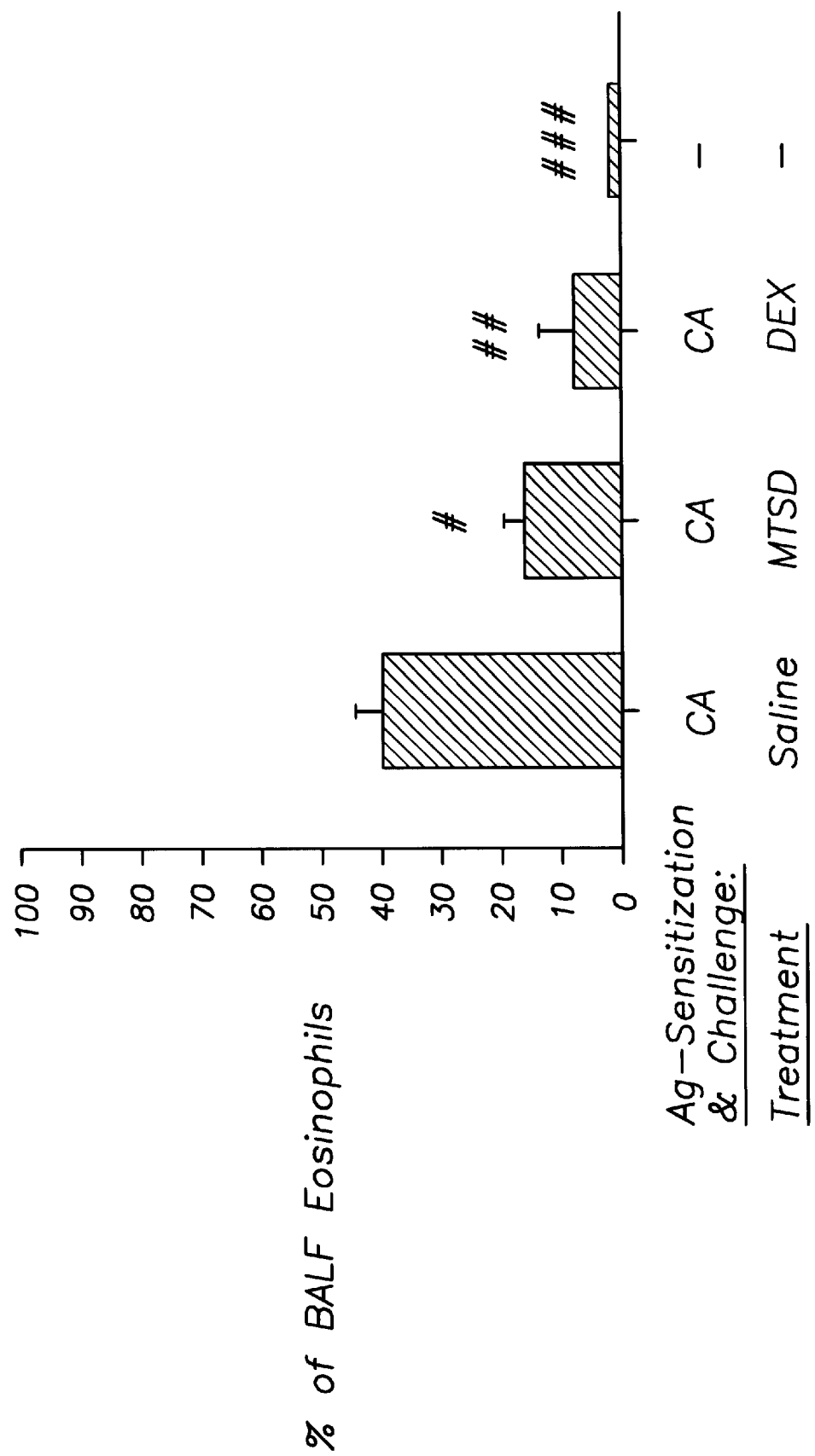

EFFECT OF MSSM-002 ON AG-INDUCED PULMONARY INFLAMMATION: To determine whether an anti-inflammatory mechanism was possibly responsible for the reduction of AHR, we determined the total cell numbers and presence of eosinophils in BALF. The total number of cells in the MSSM-002 group and the Dex treated group were decreased approximately by more than 50% compared to sham treated group (FIG. 2A, p=0.003 and p=0.002, respectively). There was no statistically significant difference between the total numbers of cells in BALF from MSSM-002 and Dex treated groups (p=0.438). While BALF from naive mice contained virtually no eosinophils, BALF from the sham treated, Ag-sensitized, challenged group contained 41% eosinophils (FIG. 2B). Both MSSM-002 and Dex treatment reduced the number of eosinophils in BALF by more than 50% (p<0.0003, p<0.00001 vs. saline), and there was no statistically significant difference between the two treatments (p=0.17).

Figure 3:
FIG. 3 shows the effect of MSSM-002 administration on goblet cells in a murine asthma model.

EFFECT OF MSSM-002 ON AG-INDUCED GOBLET CELLS: Goblet cell hyperplasia is typically observed in airways of asthmatic patients and animal models of allergic asthma. Mucus plugging has long been recognized as a major factor contributing to the mortality associated with acute severe asthma attacks (Kay, *J. Allergy Clin. Immunol.* 87:893, 1991; incorporated herein by reference) Corticosteroids such as Dex have been previously shown to reduce bronchial mucus cells. (Hermann et al., *Am J. Respir. Crit. Care Med.* 159:580, 1999; incorporated herein by reference) To determine the effect of MSSM-002 on mucus cell generation, we compared PAS stained sections of lungs from mice treated with MSSM-002 to lungs of sham treated mice 3 days following the last i.t. challenge. Numerous PAS positive goblet cells were present in the bronchi and bronchioles of sham treated mice (FIG. 3A). In some instances, the bronchial lumens were filled with mucus. In contrast, the number of mucus-containing epithelial cells in the airways of MSSM-002 treated mice were markedly reduced (FIG. 3B), and little, if any, mucus was found in the bronchial lumens.

Figure 4A:
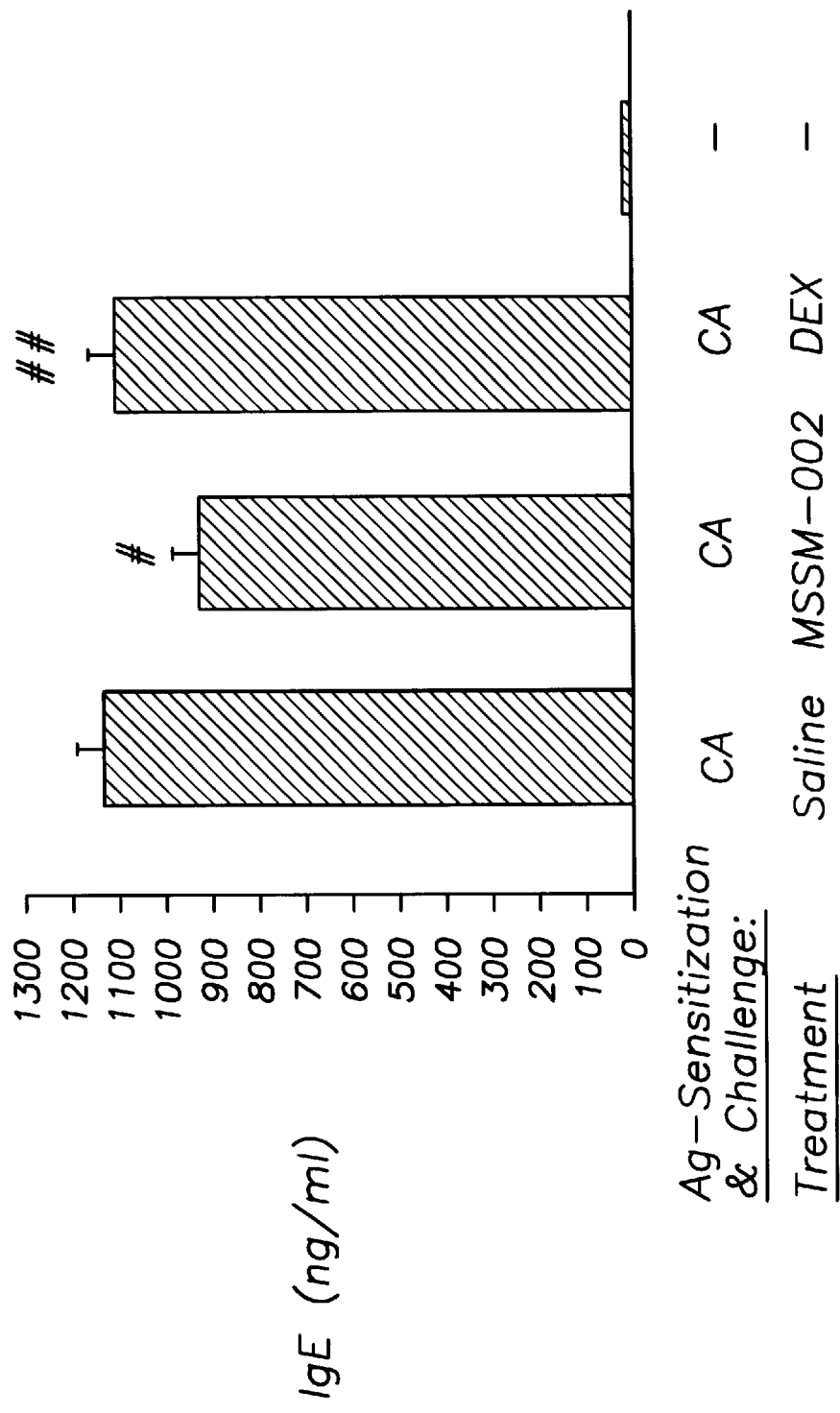
FIG. 4 depicts the effect of MSSM-002 administration on serum CA-specific antibodies in a murine asthma model. Blood was obtained from each group of mice (n greater than or equal to 8) immediately following the measurement of APTI. The levels of serum CA-specific antibody were measured by ELISA. Panel A shows IgE levels (#, $p<0.002$; ##, $p<0.04$ vs. saline); panel B shows IgG2a levels (#, $p<0.04$; ##, $p<0.03$ vs. saline).
Figure 4B:
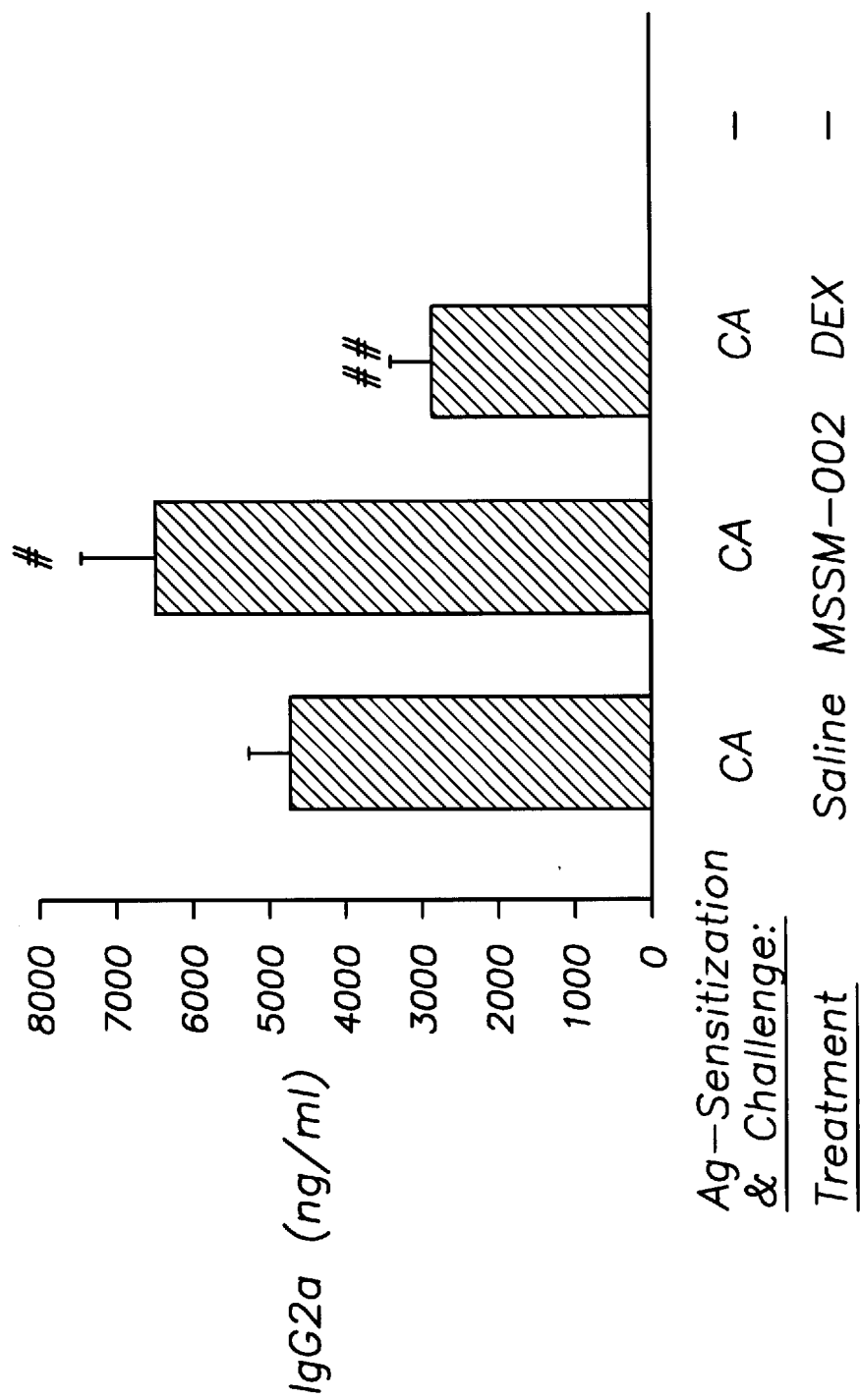

EFFECT OF MSSM-002 ON AG-SPECIFIC ANTIBODY RESPONSES: To determine the effects of MSSM-002 treatment on humoral immune responses, we measured serum CA-specific IgE and IgG2a. As shown in FIG. 4, IgE levels were significantly decreased and IgG2a levels were significantly increased in the MSSM-002 treated groups compared to sham treated group (IgE, p=0.002; IgG2a, p=0.04 vs. saline). Dex treatment also significantly decreased IgE levels (p=0.04 vs saline), but unlike MSSM-002, Dex also significantly reduced IgG2a levels (p=0.03 vs. saline). Moreoever, MSSM-002 inhibition of Ag specific-IgE levels was greater than that of Dex. These results indicate that Dex has an overall suppressive effect on B cell antibody synthesis whereas MSSM-002 suppresses primarily Ag specific IgE.

Figure 5A:
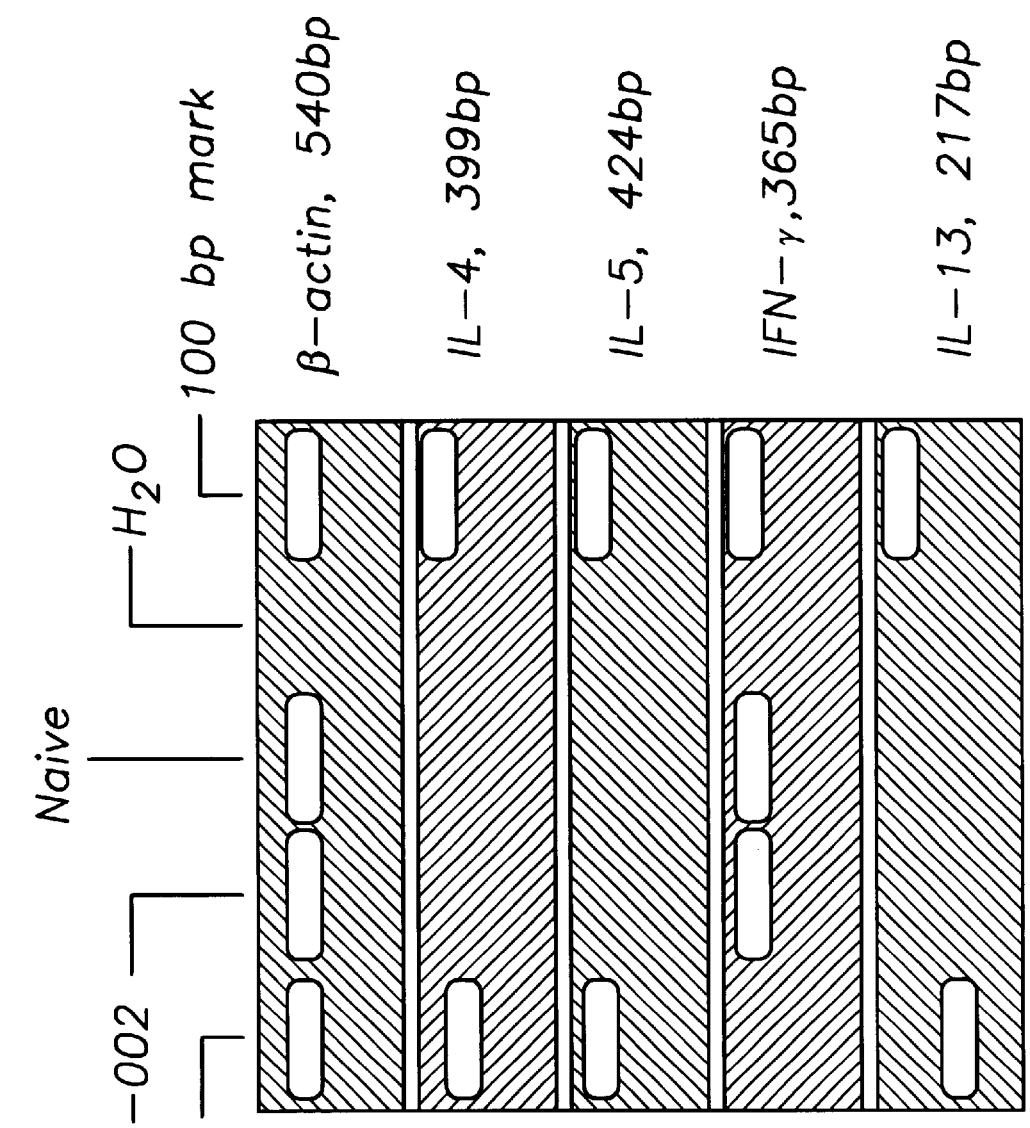
FIG. 5 shows the effect of MSSM-002 administration on T cell cytokine production. Immediately following APTI measurement, spleen cells from each group of mice (n greater than or equal to 8) were isolated, cultured in complete culture medium in the presence or absence of CA (50 $\mu$g/ml) or Con A (2 $\mu$g/ml). Supernatants were collected after 72 hr. culture. Levels of IL-4, IL-5, IL-13, and IFN-$\gamma$ in culture supernatants were determined by ELISA. Panel A shows message levels for IL-4, IL-5, IL-13, and IFN$\gamma$; and panels B, C, D, and E show the level in the supernatant of cultured spleen cells of IL-4, IL-5, IL-13, and IFN-$\gamma$, respectively.
Figure 5B:
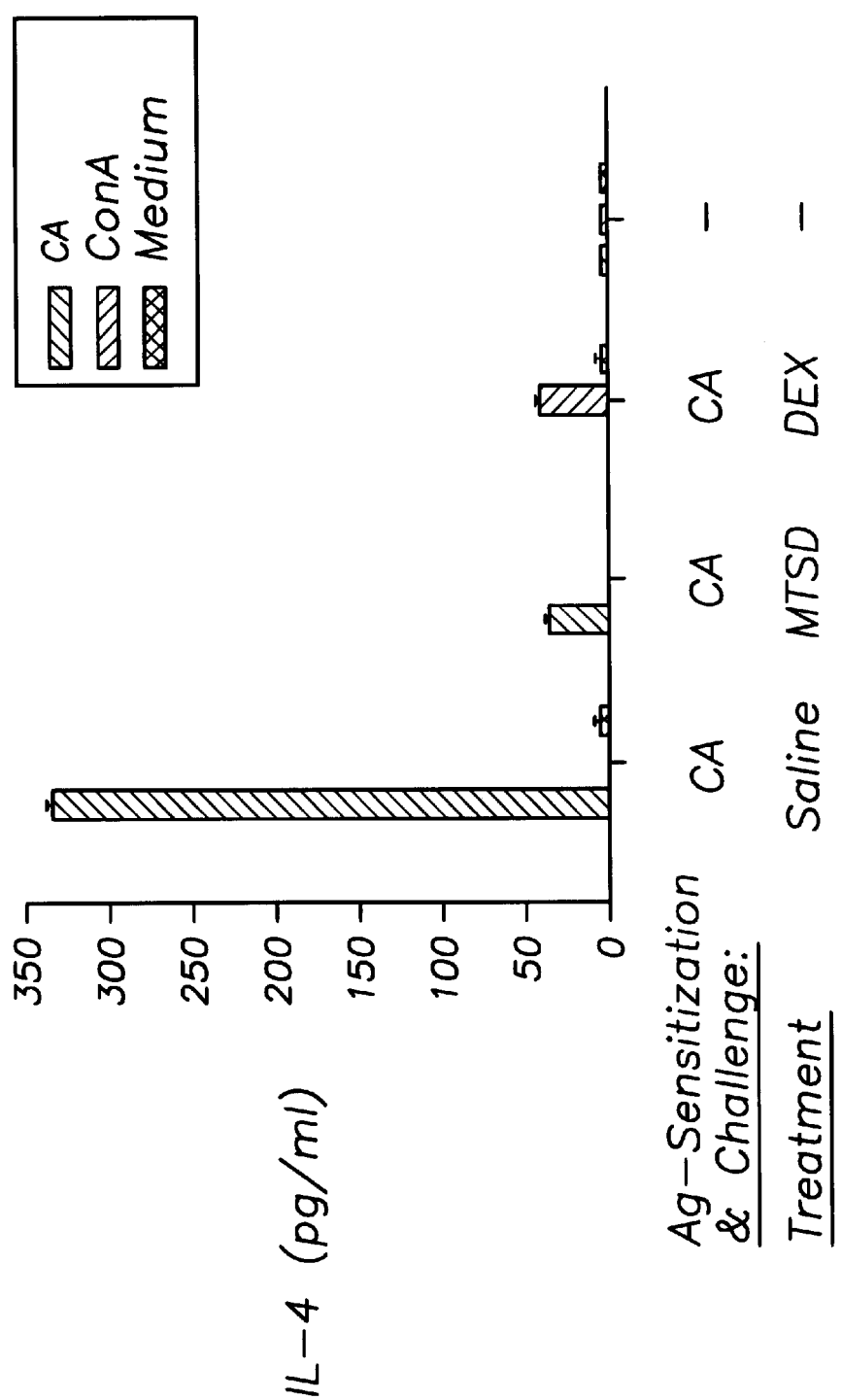
Figure 5C:
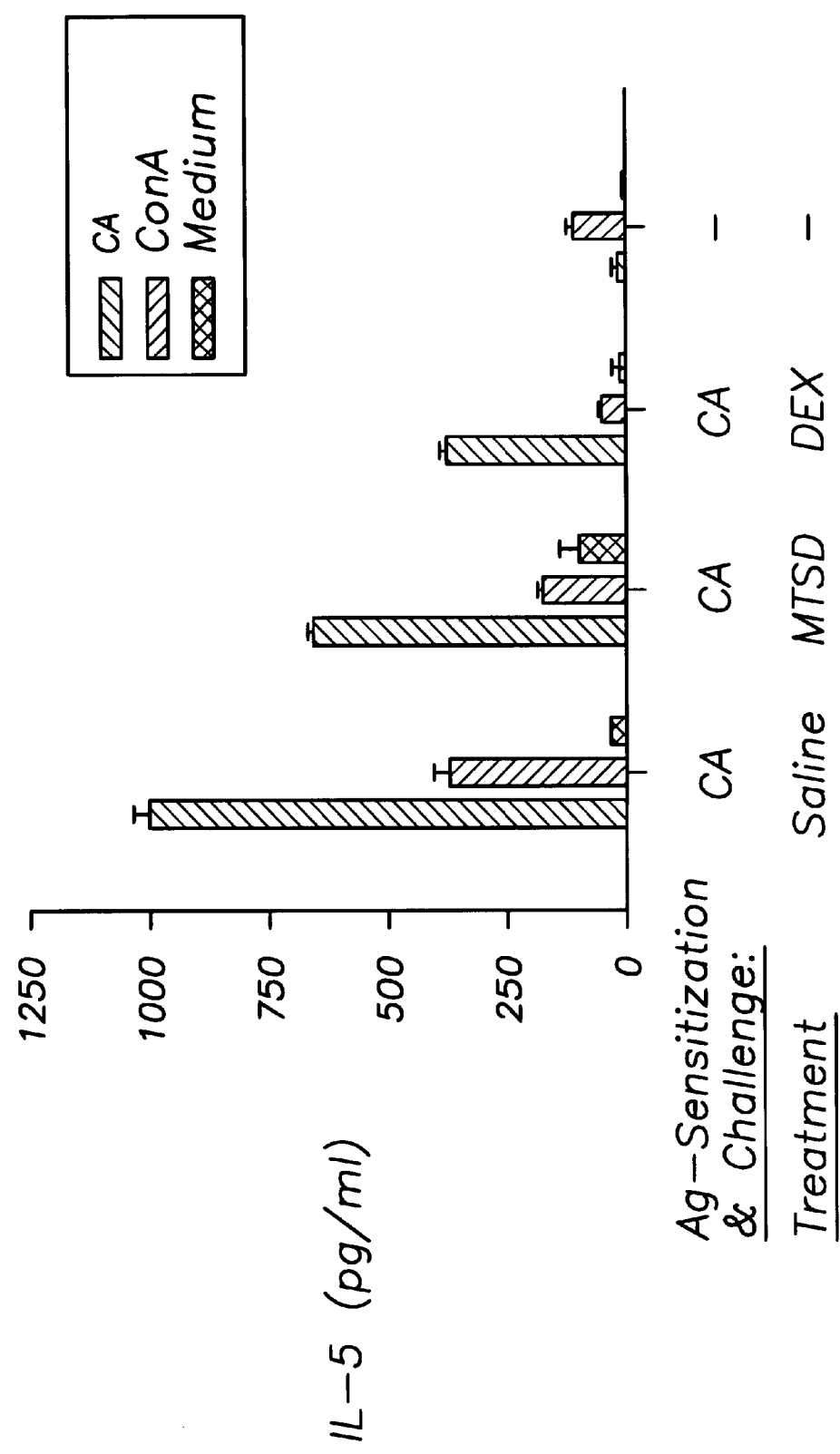
Figure 5D:
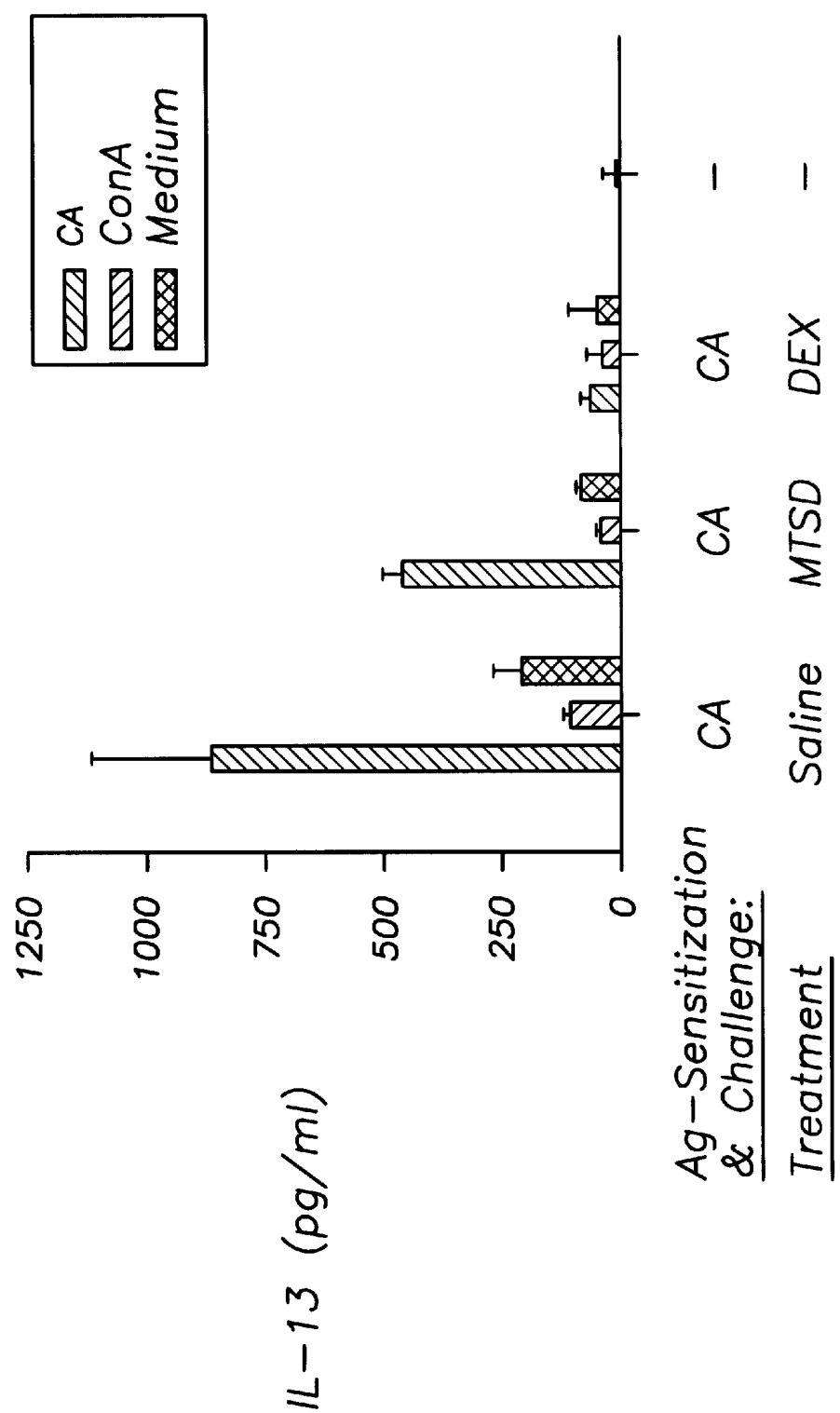
Figure 5E:
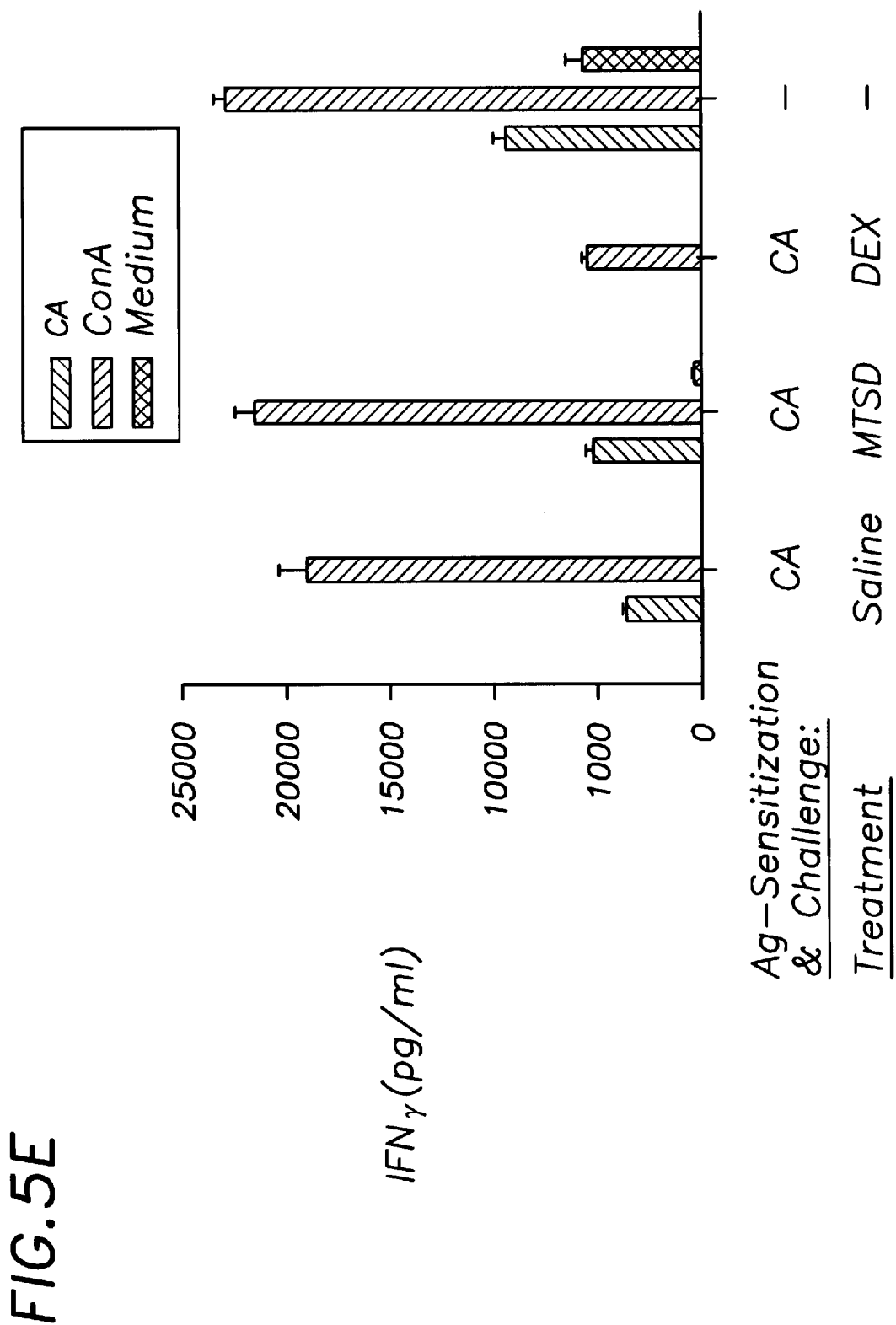

EFFECT OF MSSM-002 ON T CELL CYTOKINE RESPONSES: To determine the role of MSSM-002 on T cell responses, we first determined cytokine mRNA expression in the lungs by using semi-quantitative RT-PCR. Consistent with our previous finding, lungs from Ag-challenged sham-treated mice showed dramatic increases in IL-4, IL-5, and IL-13, and decreased IFN-$\gamma$ expression compared with normal controls, demonstrating a Th2-type response (FIG. 5A). In contrast, IL-4, IL-5 and IL-13 mRNA expression in the lungs of MSSM-002-treated mice were markedly reduced as compared with sham-treated mice. IFN-$\gamma$ mRNA expression in the lungs of MSSM-002-treated mice was increased as compared with sham-treated mice, but was equivalent to that in the lungs of normal mice.

To determine a possible effect of MSSM-002 on T cell responses, we determined the effects of MSSM-002 and Dex on T cell cytokine secretion by measuring cytokine levels in the splenocytes culture supernatants. As shown in FIG. 5, IL-4, IL-5, and IL-13 levels were markedly increased, and IFN-$\gamma$ levels were significantly decreased in cultures of Ag-sensitized/challenge/sham treated mice compared to normal controls, suggesting a predominant Th2 response. However, in splenocyte cultures from MSSM-002 treated mice, IL-4 levels were virtually abrogated, IL-5 and IL-13 levels were reduced by approximately 40%, but IFN-$\gamma$ levels were significantly increased (p<0.02 vs. saline), as compared to those in the cultures of sham treated mice. However, the increased IFN-$\gamma$ secretion induced by stimulation with CA or Con A was not higher than normal. In cultures from Dex treated mice, IL-5 and IL-13 levels were markedly decreased, and IL-4 as well as IFN-$\gamma$ secretion was virtually abrogated. These results demonstrated that in contrast to the nonspecific suppression of T cell responses by Dex, MSSM-002 treatment resulted in specific suppression of Th2 cytokine synthesis.

Example 2

Evaluation of Additional Herbal Formulations in Murine Model

Introduction

In light of the inventive teachings that certain herbal formulations can have useful anti-asthmatic activities, it becomes desirable to test other herbal formulations, including some traditional Chinese formulations.

As mentioned above, some of these traditional formulations have been reported to be useful in the reduction of one or more symptoms that can be associated with asthma. For example, formulations such as Minor blue Dragon, Xiao-Chai-hu-tang, Ma-Xing-Shi-Gan-Tang, Ding-Chuan-Tang, Liu-Wei-Di-Huang-Wan, and Jian-Fei Pill have been reported to improve some asthmatic symptoms and medical scores, to reduce the need for steroids and $\beta_2$-agonists, to increase PEF values, and/or to increase blood eosinophils in some patients (But et al., *Clin. Rev. Allergy Immunol.* 14:253, 1996; Hsieh et al., *Pediatr. Allergy Immunol.* 14:253, 1996; Zhang et al., *Chung. Kuo Chung. Hsi. I. Chieh. Ho. Tsa. Chih.* 17:204, 1997; Sun et al., *Chung. Kuo Chung. Hsi. I. Chieh. Ho. Tsa. Chih.* 17:201, 1997; Zou et al., *Chung. Kuo. Chung. Hsi. I. Chieh. Ho. Tsa. Chih.* 16:529, 1996; Xu et al., *Chung. Kuo. Chung. Hsi. I. Chieh. Ho. Tsa. Chih.*, 16: 198–200, 1996; Egashira et al., *Ann. NY Acad. Sci.* 685:580, 1993; each of which is incorporated herein by reference).

Also, some animal studies have suggested that certain traditional Chinese herbal formulations may inhibit antigen-induced AHR and eosinophil infiltration (Toda et al., *Ann. NY Acad Sci.* 685:561, 1993; incorporated herein by reference). It has further been reported that some such formulations may inhibit histamine release and leukotriene production both in vivo and in vitro (Hseih et al., *Pediatr. Allergy Immunol.* 7:130, 1996; Toda et al., *J. Ethnopharmacol.* 24:303, 1988; Hamasaki et al., *J. Ethnopharmacol.* 56:123, 1997; each of which is incorporated herein by reference). We will test these standard formulas, in addition to a variety of "modified" formulas, for their effects both on preventing the establishment of an asthmatic or allergic state, and the reversal of an already established state.

In designing "modified" formulas to test, we will rely on our experiences with MSSM-001 and MSSM-002, as well as additional experience we gain in testing additional standard formulations. For example, with regard to MSSM-002, we will test a variety of "modified" formulations that contain at least Huang Qing, Ku Shen, and Ling Zhi, but that don't necessarily include all of the other ingredients listed in Table 3, and may contain others. Preferably, these modified MSSM-002 formulations will also include one or more of Dong Gui and/or Ge Gen, and may also (or alternatively include Su Zi. Some examples of other herbs that could be added to MSSM-002 and/or to one or more modified MSSM-002 compositions are presented below in Table 5, along with their particularly preferred amounts:

TABLE 5

OPTIONAL HERBS FOR USE IN MODIFIED MSSM-002 FORMULATIONS

| CHINESE NAME | PLANT NAME | AMOUNT |
|---|---|---|
| Wu Mei | *Pruni mume* | 24 g |
| Chuan Jiao | Pericarpium Zanthoxylum Bungeanum | 3 g |

TABLE 5-continued

OPTIONAL HERBS FOR USE IN
MODIFIED MSSM-002 FORMULATIONS

| CHINESE NAME | PLANT NAME | AMOUNT |
|---|---|---|
| Bai Guo | *Ginko biloba* | 3 g |
| Wu Wei Zi | Schizandra Sphenathera | 9 g |
| Radix Angelica Sinensis | Dang Gui | 6–9 g |

Materials and Methods

MICE AND REAGENTS: Male AKR/J mice (6–8 wk old) will be purchased from the Jackson Laboratory (Bar Harbor, Me.) and maintained in the animal facility at Mount Sinai Hospital. Standard guidelines for lab animal care will be followed (Guide for the Care and Use of Laboratory Animals (NIH Publication No. 86-23, as revised)).

All Chinese herbal medicines will be purchased from Mayway Corp. (Oakland, Calif.) or Blue Light Inc. (Ithaca, N.Y.). Conalbumin (CA), DNP-BSA, and Dex will be purchased from Sigma (St. Louis, Mo.).

AG SENSITIZATION, CHALLENGE, AND TREATMENT: Mice in each group (FIG. 6) will be sensitized and challenged with CA as described previously. (Li et al., *J. Immunol.* 160:1378, 1998; incorporated herein by reference). Briefly, mice will receive two injections of CA i.p. for sensitization (1 week apart) using 200 µg absorbed in 2 mg of alum in 0.3 ml of saline. Seven days following the last sensitization, mice will be anesthetized and challenged i.t. with 100 µg of CA in 0.05 ml of saline followed by two more i.t. challenges at 10 day intervals.

Figure 6:
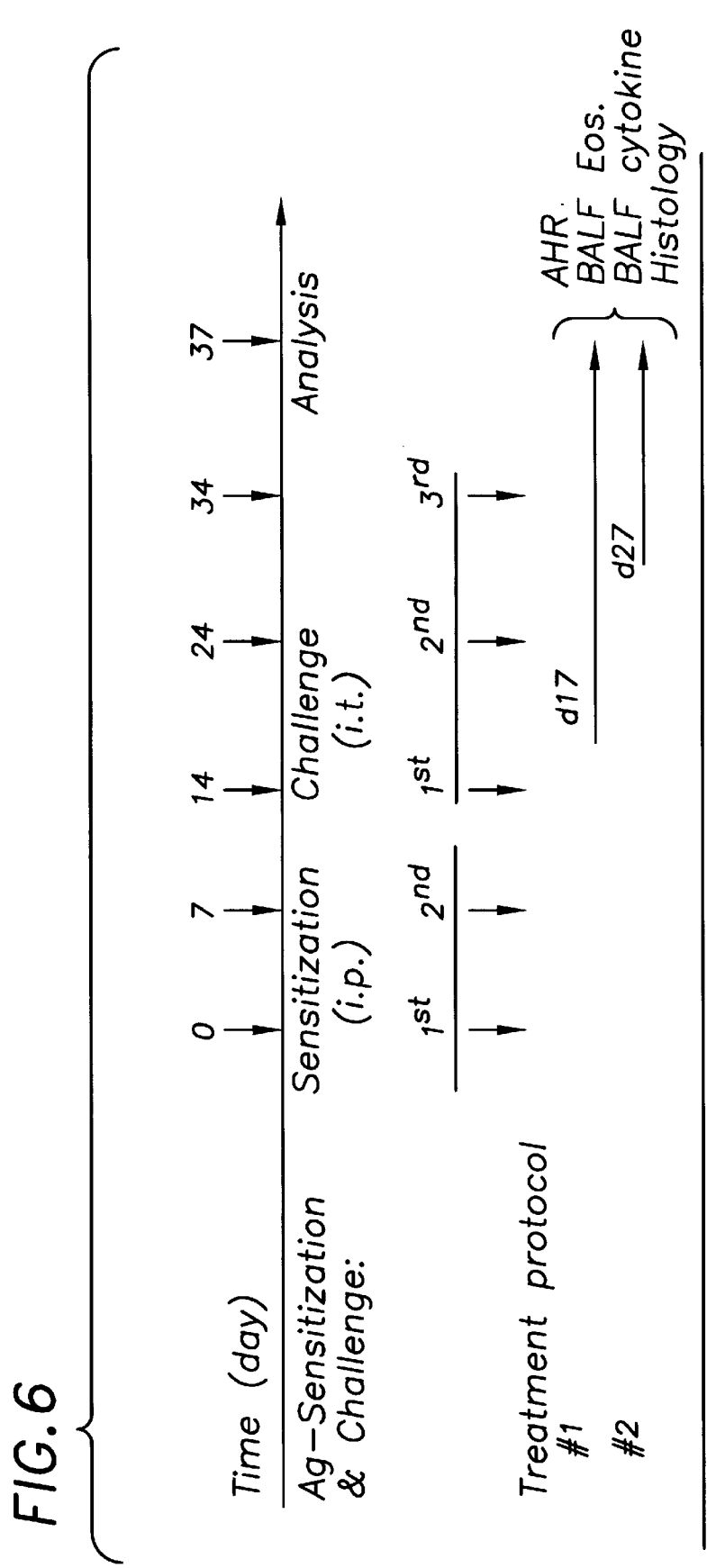
FIG. 6 presents an experimental protocol for testing additional herbal formulations for their effects on asthma in accordance with the present invention.

To investigate whether herbal formulations can suppress and/or reverse ongoing allergic airway reactions, compositions will be administered 3 days after the first i.t. challenge (Protocol #1) or 3 days after the second i.t. challenge (Protocol #2) as described in FIG. 6. Mice will receive herbal medicines twice daily for 19 days in protocol #1 and for 10 days in protocol #2. Intragastric administration will be performed by means of a 25-gauge stainless steel blunt feeding needle (Fine Science Tool Inc. CA, USA). The dose of herbal formulations used in this study will be based on the equivalent effective dose prescribed for humans (Xiu *The People's Public Health Publisher*, 985 1986; incorporated herein by reference). Control treatment groups will receive i.p. Dex (0.5 mg/kg) daily, as described previously (De et al., *Br. J. Pharmacol.* 119: 1484, 1996; incorporated herein by reference), at the same times as herbal treatments. A saline sham-treatment group will serve as a control.

MEASUREMENT OF IMMEDIATE AIRWAY RESPONSES: Immediate airway responsiveness will be monitored in conscious unrestrained mice 30 min, 1 hr, and 2 hr following i.t. challenge using Kent Scientific Mouse System's whole body plethysmograph chamber and Respiratory Parameter software, TRN 3000 (Kent Scientific Corporation, CT). Briefly, following i.t. challenge, mice are placed in the whole body plethysmograph chamber without any direct restraints such as neck seals that may cause stress. Bias airflow is passed through the chamber and out through a direct airflow sensor. The signals denoting PEF and TE will be monitored and recorded. The decreases in PEF and increases in TE indicate bronchial contraction.

MEASUREMENT OF LATE-PHASE AIRWAY RESPONSES: Three days after the last i.t. Ag challenge, airway responsiveness will be determined by measuring airway pressure changes following intravenous (i.v.) Ach challenge as previously described with minor modification (Li et al., *J. Immunol.* 160:L 1378–1384, 1998; Levitt et al. *FASEB J.* 2:2605, 1988; each of which is incorporated herein by reference). Briefly, mice will be anaesthetized with sodium pentobarbital (60 mg/kg), and ventilated via a tracheal cannula (18 gauge) at the rate of 120 per minute with a consistent tidal volume of air (0.2 ml) with RSP 1002 Pressure Controlled Respirator System (Kent Scientific Corporation, CT). Muscle paralysis is provided by i.v. administration of decmethonium bromide (24 mg/kg). Airway pressure is measured with a pressure transducer via a port in the trachea. Two minutes after establishing a stable airway pressure recording, Ach is injected i.v. (50 µg/kg). The signals of airway pressure changes are then viewed and recorded, and pulmonary parameters are generated with the software respiratory data acquisition system, VENTP (Kent Scientific Corporation, CT). The time-integrated changes in peak airway pressured referred to as the airway pressure-time index (APTI; cm $H_2O$ per second) will be calculated and serve as the measurements of airway responsiveness.

BALF PREPARATION AND CELL DIFFERENTIAL COUNTS: Following the measurement of airway responsiveness, mice will be sacrificed and lungs will be lavaged with 1.0 ml of ice-cold HBSS (without magnesium or calcium). The BALF will be collected into chilled tubes. After centrifugation (1500 rpm) for 10 min at 4° C., aliquots of supernatants will be collected and frozen at –80° C. until analyzed. Cell pellets will be re-suspended in 0.5 ml of HBSS and cytospin slides will be made (Shandon Scientific, Pittsburgh, Pa.). Slides will be stained with Diff-Quick Stain Set (Dade Diagnostics of P.R. Inc., Aguada, PR). Differential counts of BAL cells will be determined by microscopic evaluation. Five hundred cells per slide will be counted.

DETERMINATION OF BALF HISTAMINE AND LEUKOTRIENE LEVELS: Histamine levels of BALF supernatants prepared above will be determined using an enzyme immunoassay kit (Immuno TECH Inc., ME), as described by the manufacturer and in our previous study. (Li et al., *J. Immunol.* 162: 3045–3052, 1999; incorporated herein by reference). Leukotriene C4 (LTC4) in BALF Supernatants will be determined using an LTC4 Enzyme Immunoassay Kit (Cayman Chemical Co., Ann Arbor, Mich., USA).

HISTOLOGY: To assess the effect of herbal formulations on lung inflammation and goblet cell numbers, lung samples will be fixed in neutral buffered formaldehyde, and embedded in paraffin. Five-micron sections will be stained with hematoxylin and eosin (H and E), and periodic acid Schiff's reagent (PAS) for analysis of inflammatory cells and goblet cells. In order to determine any possible toxicity of the inventive herbal formulations, organs from different groups of mice will be collected and processed for pathologic analysis.

STATISTICAL METHODS: In this Example, we will perform an overall Analysis of Variance, followed by Dunnett's test to compare each of the five preliminary herbal interventions and MSSM-002 to the saline preparation. The pilot data indicated an increase in variability with mean, and so a square root transformation might be considered. To examine the interrelationship between eosinophils and AHR, we will compute the correlations within groups, and in addition perform a multiple regression in which the outcome is APTI, and the predictors, group and % of BALF eosinophils.

POWER: We computed N, the required sample per group, for 80% power, using a two tail test at the 0.05 level, based on the formula: $N=2$ (critical value+0.84)2 $(s.d./diff)^2$, where diff is the difference to be detected, s.d. the standard deviation. For this Aim, we plan to use Dunnett's test to one or more of 5 active preparations, so that the critical value is 2.75. To detect the difference of 739 units in APTI noted in the preliminary study, based on a standard deviation of about 450, 8 to 9 mice per group will be required. Since we have already been conservative in setting the critical value, and hope to use a transformation to insure more nearly equal variability, we chose the lower number. We would have more than enough animals to detect differences in % of BALF eosinophils, since the observed difference was about 2 s.d. An additional objective is to compute the correlation between the two outcomes noted above (reduction of AHR and eosinophils) within each of the groups, with particular emphasis on the MSSM-002 group. To detect a correlation of 0.7 with 80% power, requires N=18.

Example 3

Analysis of Immunological Methods of Action of Inventive Herbal Formulations

Introduction

Allergic airway inflammation and AHR in asthma is a complex cascade of events that is mediated by a Th2-type response characterized by increased Ag-specific IgE and Th2 cytokine (IL-4, IL-5, IL-13, IL-16, IL-3, GFC-SF) production. IgE antibodies play an important role in mediating immediate hypersensitivity reactions in humans and animals (Martin et al., *J. Clin. Invest*. 83: 1375–1383, 1989; Ishizaka et al., *J. Immunol*. 106: 705, 1971; each of which is incorporated herein by reference). Antigen cross-linking of receptor-bound IgE on these cells leads to their degranulation, and release of histamine and other mediators, which trigger an ongoing inflammatory reaction. Repeated antigen exposure leads to an inflammatory state, and over time to airway remodeling (Bousquet et al., *Curr. Opin. Pulm. Med*. 3:42, 1997; incorporated herein by reference). The prevalence of sensitization to allergens is positively correlated with the frequency of asthma and its severity (Sporik et al., *N. Engl. J. Med*. 323:502, 1990; Burrows et al., *Br. J. Pharmacol. Suppl*. 98:789, 1989; each of which is incorporated herein by reference).

It is now well established that polarized T cell responses lead to the release of cytokines important in allergic responses. Th2 cells elaborate IL-4, IL-5, and IL-13 etc., but not IFN-$\gamma$. These Th2 cytokines promote IgE synthesis, eosinophil development and recruitment, and goblet cell hyperplasia, thus contributing to the allergic airway inflammation, and AHR. Studies have suggested that some anti-asthma traditional chinese medicine formulas may be able to reduce some asthma symptoms, perhaps reduction of allergic airway inflammation and AHR (Hsieh et al., *Taiwan Asthma Study Group, Pediatr. Allergy Immunol*. 7: 130, 1996; Egashira et al., *Ann. NY. Acad. Sci*. 685: 580, 1993; But et al., *Clin. Rev. Allergy Immunol*. 14: 253, 1996; Zhang et al., *Chung. Kuo Chung*. 17: 204, 1997; Xu et al., *Chung. Kuo. Chung*, 16: 198–200, 1996; Toda et al., *Ann. N.Y. Acad. Sci*. 685: 561–571, 1993; each of which is incorporated herein by reference). However, the mechanisms underlying these effects remain unclear.

Recent animal studies demonstrated that some traditional Chinese herbal formulations, such as TJ-19 (minor-blue-dragon), could decrease IgE (determined by PCA) responses by 43–91° (Recent Advances in the Pharmacology of KAMPO (JAPANESE HERBAL) MEDICINES. Tokyo: Excerpta Medica, 260: 1998; Hsieh et al., *Taiwan Asthma Study Group, Pediatr. Allergy Immunol*. 7: 130–140, 1996; Egashira et al., *Ann. NY. Acad. Sci*. 685: 580, 1993; But et al., *Clin. Rev. Allergy Immunol*. 14:253, 1996; Zhang et al., *Chung. Kuo Chung Hsi. I. Chieh. Ho. Tsa. Chih*. 17:204, 1997; Xu et al., *Chung. Kuo. Chung Hsi. I. Chieh. Ho. Tsa. Chih*, 16:198, 1996; Toda et al., *Ann. N.Y. Acad. Sci*. 685: 561, 1993; each of which is incorporated herein by reference).

Also, Nakajima et al have recently reported that saiboku-to (T-J 96; chai-pu-Tang) has an inhibitory effect on Ag-induced IgE-F R2/CD23 expression in lymphocytes of mite allergic asthmatics. Ag-induced IgE production and T cell proliferation of lymphocytes from mite allergic asthmatics were also reduced by co-culture with saiboku-to (Nakajima et al., *Ann. N.Y. Acad. Sci*, 685:549, 1993; Hsieh et al., *Taiwan Asthma Study Group, Pediatr. Allergy Immunol*. 7:130, 1996; Egashira et al., *Ann. NY. Acad. Sci*. 685:580, 1993; But et al., *Clin. Rev. Allergy Immunol*. 14 253, 1996; Zhang et al., *Chung. Kuo Chung*. 17:204, 1997; Xu et al., *Chung. Kuo. Chung*, 16:198, 1996; Toda et al., *Ann. N.Y. Acad. Sci*. 685:561, 1993; each of which is incorporated herein by reference).

Some researchers have mentioned that saiboku-to might inhibit Ag-induced IgE antibody production induced by IL-4 from Th2 cells (Nakajima et al., *Ann. N.Y. Acad. Sci*. 685:549, 1993; Oettgen et al., *Nature* 370:367, 1994; Li et al., *J. Immunol*. 162:3045, 1999; Lei et al., *Int. Arch. Allergy Immunol*. 109:407, 1996; each of which is incorporated herein by reference). However, no evidence was presented to confirm or deny this hypothesis.

As described herein, we have found that MSSM-002 inhibits airway hyperresponsiveness and reduces IgE, IL-4, IL-5, and IL-13 mRNA expression in the lung, and IL-4, IL-5, and IL-13 cytokine production by cultured spleen cells. Without wishing be bond by any particular theory, propose that the anti-asthma effects of this and other herbal formulations may be at least partially the result of down-regulation of Th2 responses.

We will explore the immunologic mechanisms underlying the inhibition of allergic airway responses by inventive herbal formulations. We will test our hypothesis that, in contrast to the generalized immunosuppression produced by corticosteroids, specific down-regulation of Th2 responses may, at least partially underlie the beneficial effects of herbal formulas found to alleviate allergic airway response.

To determine effects on humoral responses we will focus on serum Ag-specific IgE levels. IgG1 levels will not be determined because, although previous studies including our own, demonstrated that IgG1 can play an important role in mediating hypersensitivity reactions in some strains of mice (Oettgen et al., *Nature* 370:367, 1994; Li et al., *J. Immunol*. 162:3045, 1999; Lei et al., *Int. Arch. Allergy Immunol*. 109:407, 1996; each of which is incorporated herein by reference), allergic reactions in our model are mediated by IgE. IgG2a and IgA are believed to be protective antibodies. (Mosmann et al., *Annu. Rev. Immunol*. 7:145, 1989; Raz et al., *Proc. Natl. Acad. Sci. U.S.A*. 93:5141, 1996; Schwarze et al., *Am J. Respir. Crit. Care Med*. 158:519, 1998; each of which is incorporated herein by reference). The effect of inventive herbal formulations on these antibodies will also be determined.

T cell activation is an early event in Ag-induced airway inflammatory reactions. (Oettgen et al., *Nature* 370:367, 1994; Li et al., *J. Immunol*. 162:3045, 1999; Lei et al., *Int. Arch. Allergy Immunol*. 109:407, 1996; each of which is incorporated herein by reference). To determine whether anti-asthma herbal formulations selectively inhibit Th2 cytokine production, BALF will be collected at 12, 24, 48, and 72 hr following Ag-challenge and measured by ELISA for quantitation of cytokine secretion. Generally, the amount of BALF collected from each individual mouse in between 0.5–0.7 ml. This will allow us to measure 2–3 cytokines in each set of experiments. Give this limitation, and in order to detect the molecular basis of cytokine expression, RT-PCR will be employed as well. Cytokines such as IL-4, IL-5, IL-1

3, IL-10, GM-CSF, IFN-γ, and IL-2 in lung tissue samples will be determined. In addition, the phenotype of T cells, $CD4^+/CD8^+$, will be determined to evaluate whether inventive herbal treatment alters CD4/CD8 ratios, since $CD4^+$ T cells have been implicated in the development of allergic airway responses (Gavett et al., *Am. J. Respir. Cell Mol. Biol.* 10:587, 1994; incorporated herein by reference).

We have reported that transfer of CA-specific Th2 cells (D10 G 4.1 clone) into naive mice in the presence of CA induced significant Th2 cytokine (IL-4 and IL-5) production, as well as airway eosinophil inflammation and AHR. To provide further support for our hypothesis that the effects of anti-asthma herbal formulations on allergic inflammation and AHR act through the inhibition of Th2 cells and their cytokine production, we will use Th2 clones for in vivo and in vitro studies. For in vivo studies, mice will be treated with herbal formulations following the transfer of CA-specific D10 cells. Naive spleen cells will be used as controls. The inhibitory effect of the herbal formulations on Th2-mediated airway inflammatory responses and AHR will be evaluated. For in vitro studies, the Ag-specific Th2 cells will be stimulated and treated with herbal formulations. Naive spleen cells will also be used as control. The proliferative responses to Ag or mitogen stimulation and Th2 cytokine production will be determined.

In addition, to exclude immunosuppressive effects of these formulas, humoral (IgG, IgA, and IgM) and cellular immune responses will be assessed following long-term treatment in the animal model.

Materials and Methods

In addition to various methods described above, the following procedures will be followed:

MEASUREMENT OF ANTIGEN-SPECIFIC ANTIBODIES: Blood will be obtained from the tail vein on a weekly basis and immediately following the measurement of LPR from each group of mice. After centrifugation, the sera will be collected and stored at $-80°$ C. The level of Ag-specific IgE, IgG2a, and IgA will be measured by ELISA as described (Li et al., *J. Allergy, Clin. Immunol.* 103:206, 1999; incorporated herein by reference). For measurements of CA-specific IgE, Ameslan II plates (Dynatech Laboratories, Inc., Chantilly, Va.) will be coated with 2 μg/ml CA in coating buffer (Sigma, St. Louis, Mo.). After overnight incubation at $4°$ C., plates will be washed 3×'s with PBS/0.05%-Tween 20 and blocked with 1% BSA-PBS for 2 hour at RT. After 3×'s washing, dilutions of serum samples (1:10 for IgE in 1% BSA-PBS) will be added to the plates and incubated overnight at $4°$ C. Plates will be washed 3×'s and 100 μl of goat anti-mouse IgE (0.3 μg/ml) will be added to each well for an additional 1 hr incubation at room temperature (RT). After 5×'s washes, 100 μl of avidin peroxidase (Sigma, St. Louis, Mo., CA) (1:1000 dilution) will be added to each well for an additional 30 min. at RT. After 8×'s washes, the reaction will be developed with ABTS (KPL, Gaithersburg, Md.) for 30 min. at RT and read at 405 nm as described previously (Li et al., *J. Immunol.* 162:3045, 1999; Li et al., *J. Allergy Clin. Immunol.* 103:206, 1999; Li et al., *J. Immunol.* 160:1378, 1998; each of which is incorporated herein by reference).

For measurement of CA-specific IgG2a and IgA, plates are coated with CA. For measurement of total IgG, IgA, and IgM, plates will be coated with rat anti-mouse IgG or IgA monoclonal antibodies (1 μg/ml; PharMingen San Diego, Calif.). Plates then will be blocked and washed in the same manner as above. Samples (1:50 dilution for IgG and 1:10 for IgA) will be added to the plates and incubated overnight at $4°$ C. Plates will be washed and biotinylated rat anti-mouse IgG2a, or IgG, or IgA, or IgM monoclonal antibodies will be added to the plates for detection of IgG2a, or IgG, or IgA, or IgM, respectively. Plates will be incubated for an additional 1 hour at RT. After washing, avidin-peroxidase will be added for an additional 15 min. at RT. After 8×'s washes, the reactions will be developed with ABTS (KPL) for 30 min. at RT and read at 405 nm.

The levels of CA-specific IgE and IgG2a will be determined by comparison with a reference curve generated with mouse monoclonal antibodies anti-DNP IgE or IgG2a (Accurate Scientific Inc. NY, USA). Briefly, human-albumin-dinitrophenyl (DNP-albumin) will be coated at the same concentration as CA. After overnight incubation at $4°$ C., the plates will be washed and blocked as described above. Ten serial 1:2 dilutions of mouse anti-DNP antibodies starting from 1000 ng/ml will be added. The level of Ag-specific IgA will be calculated as equivalent concentration to total mouse IgA as described below. The total IgG, IgA, and IgM will be calculated with a standard curve. Briefly, plates will be coated with rat anti-mouse IgG, IgM or IgA (1 μg/ml). After overnight incubation at $4°$ C., the plates will be washed and blocked as described above. Ten serial 1:2 dilutions of mouse IgG, IgM, or IgA, starting from 1000 ng/ml will be added. Thereafter all the steps will be performed in a similar manner. All analyses will be performed in duplicate and coefficient of variation (CV)>15% will be repeated to ensure a high degree of precision.

QUANTIFICATION OF CYTOKINE PROTEINS: BALF and cell culture supernatants will be collected. IL-4, IL-5, IL-13, and IFN-γ levels will be determined by ELISA according to the manufacturer's instructions (PharMingen, San Diego), and as previously described (Li et al., *J. Immunol.* 160:1378, 1998; incorporated herein by reference).

CELL CULTURE: Splenocytes will be isolated and suspended in RPMI 1640 containing 10% fetal bovine serum, 1% penicillin/streptomycin, and 1% glutamine. Cells ($4 \times 10^6$/ml/well) will be cultured in 24-well plates in the presence or absence of CA (50 μg/ml) or Con A (5 μg/ml). Supernatants will be collected after 72-hr culture.

RT-PCR: Total RNA will be isolated from lung tissues using TRIzol reagent (Gibco BRL), as described by the manufacturer. The reverse transcription will be performed using the Superscript Amplification System kit for cDNA synthesis (Gibco BRL), as described by the manufacturer (Krzeski et al., *Am. J. Respir. Cell Mol. Biol.* 16:693, 1997; incorporated herein by reference). PCR will be performed as described previously (Gavett et al., *J. Exp. Med.* 182:1527, 1995; Simpson et al., *Inflamm. Res.* 46:65, 1997; each of which is incorporated herein by reference), with slight modification. Briefly, PCR reactions (50 μl total volume) will be carried-out in 2 mM $MgCl_2$, 1×PCR buffer, using 2.5 units AmpliTaq DNA polymerase, 2 μl of 10 μM of anti-sense and sense primer pair and the 2 μl reverse transcription products. PCR will be carried out beginning with $95°$ C. for 45 s; primer annealing, $60°$ C. for 45 s; and primer extension, $72°$ C. for 90 s. A final cycle of $72°$ C. for 90 s. A final cycle of $72°$ C. for 10 min will be performed.

Once the PCR reactions are complete, 10 μl of the reaction mixture will be separated by electrophoresis through a 2.5% agarose gel and visualized by ethidium bromide staining and UV irradiation. Gel images will be captured using a Gel Doc Image Analysis system (BioRad, Hercules, Calif.) and PCR product quantitation will be performed by densitometry using Quantity One Software (BioRad) and standardized against β-actin from the same mRNA preparation (Prior to analysis, the PCR product band intensities will be checked to ensure that they had not reached saturation). Results will be expressed as an OD ratio (cytokine-β-actin). All reactions will be repeated at least 2–3 times. Oligonucleotide primers for IL-2, IFN-γ, IL-4, IL-5, IL-6, IL-10, GM-CSF, and β-actin used in the PCR are purchased from Clontech (Clontech Laboratories, Inc., Palo Alto, Calif.) and IL-13 was obtained from Life Technologies (Grand Island, N.Y.).

FLOW CYTOMETRIC ANALYSIS OF T CELL PHENOTYPES: T cell preparations from BALF or spleen cells are suspended in cold HBSS containing 2% FCS and incubated with appropriate mAbs at 4° C. for 30 min. The cells are washed with PBS and aliquots of the cell suspensions ($1 \times 10^6$) are treated with FITC-conjugated rat anti-mouse CD3 mAb, and PE-conjugated rat anti-mouse CD4 or CD8 mAbs (PharMingen, San Diego). The flow cytometric analysis is performed with the use of FACscan (Becton Dickinson, San Jose, Calif.).

CELL TRANSFER AND TREATMENT WITH INVENTIVE HERBAL FORMULATIONS: The Ag-specific T-cell clone, D10.G4.1 (D10; purchased from ATCC, Rockville, Md.) is a classic CA-specific Th2 clone derived from AKR/J mice. (Naora et al., *J. Immunol.* 152: 5691, 1994; incorporated herein by reference). D10 cell culture and transfer will be performed as previously described (Li et al., *J. Immunol.* 160:1378, 1998; incorporated herein by reference). Briefly, D10 cells are stimulated periodically with CA (100 μg/ml) in the presence of irradiated AKR spleen cells as antigen presenting cells (APCs). Prior to the cell transfer, D10 cells are kept in culture for 8 days after stimulation, and the viable cells isolated and suspended in media containing Ag (CA, 4 mg/ml) or PBS. In addition, spleen cells from naive AKR mice are suspended in the same media. Aliquots of the cell suspensions ($5 \times 10^6$ cells in 0.05 ml) from various conditions are transferred into the mouse lungs by tracheal injection. Treatment groups will receive anti-asthma herbal formulations simultaneously with cell transfer. Three days following cell transfer, airway responsiveness and BAL cell differential counts will be determined as described above.

T CELL PROLIFERATION ASSAYS: D10 cells ($5 \times 10^4$/well) will be incubated with irradiated syngeneic APCs ($5 \times 10^5$/well) in triplicate cultures in microwell plates in the presence or absence of Ag (CA, 50 μg/ml) or Con A (2 μg/ml). Cells will be treated with inventive herbal formulations at 10 different concentrations beginning at 1,000 μg/ml to 10 μg/ml. Cultures will be maintained in the complete culture medium as above. Naive spleen cells will be stimulated and treated in the same manner. After 72 hr, the cultures are pulsed for 18-hr with 1 μCi per well of $^3$H-thymidine. The cells are harvested and the incorporated radioactivity counted in a β-scintillation counter. The results are expressed as counts per minute (cpm).

To determine whether inventive herbal formulations affect Th2 cytokine production, D10 cells ($5 \times 10^5$) will be stimulated and treated as above. Culture supernatants will be collected 48 and 72 hr later. The levels of cytokines (IL-4 and IL-5) will be determined by ELISA as described above.

STATISTICAL METHODS: For analysis of antibody levels, we will perform an overall Analysis of Variance, followed by modified t-tests (based on a pooled variability: LSD method) for pairwise comparisons. Although there are more than 2 groups, no adjustment for multiple testing is deemed necessary, since different hypotheses are being tested. For analysis of cytokine levels in culture supernatants, the simplest analysis is the same as described for analysis of antibody levels performed separately for each culture. To fully exploit the three different cultures, we will also test for an interaction between the three cultures and treatments (saline, Dex and the best of the inventive herbal compositions).

POWER: We computed sample sizes using power analysis as described above. In Example 2, where there was only one best preparation of interest, the critical value used in the formula for Power is close to 1.96, and the multiple of nearly 16 agrees with conventional textbook formulas. To detect a difference of 204 ng/ml of IgE based on a standard deviation of about 140, 7 to 8 mice per experimental group will be required.

Example 4

Reduction of Allergic Symptoms in a Murine Model Using Herbal Compositions WMW Plus LZ Introduction We tested the effects of the herbal composition, WMW plus LZ, on a murine model of allergies. We found that WMW plus LZ reduced Ag-induced allergic symptoms, antigen-specific IgE levels, and histamine release, and prevented drop in body temperature upon challenge with antigen. We have compared the effect of WMW plus LZ with sham treated mice and mice treated with LZ alone. We have found WMW plus LZ to be even more effective than LZ alone. We also demonstrated that treatment with a low dose (10 mg per mouse) eliminated anaphylactic reactions and that a higher dose of WMW plus LZ further reduced peanut-specific IgE levels. Furthermore, two weeks of treatment significantly reduced serum IgE levels as compared to sham-treated mice, which remained lower throughout the treatment course. These results demonstrate that WMW+LZ largely reversed established peanut allergy and protected sensitized mice from anaphylactic reactions following peanut challenge.

Materials and Methods

Mice and Reagents

Female C3H/HeJ mice, 5 weeks (wk) of age were purchased from the Jackson Laboratory (Bar Harbor, Me.) and maintained on peanut [PN]-free chow under specific pathogen-free conditions. Standard guidelines for the care and use of animals were followed (Institute of A Laboratory Animal Resources Commission of Life Sciences NRC, Guide for the Care and Use of Laboratory Animals, National Academy Press, 1996; incorporated herein by reference).

Freshly ground whole PN was employed as allergen. Crude PN extract was prepared as described previously (Burks et al. "Identification and characterization of a second major peanut allergen, Ara h II, with use of the sera of patients with atopic dermatitis and positive peanut challenge" *J. Allergy Clin. Immunol.* 90:962–969, 1992; Burks et al. "Identification of soy protein allergens in patients with atopic dermatitis and positive soy challenges; determination of change in allergenicity after heating or enzyme digestion" *Adv. Exp. Med. Biol.* 289:295–307, 1991; each of which is incorporated herein by reference). Cholera toxin was purchased from List Biological Laboratories, Inc (Campbell, Calif.). Concanavalin A (Con A) and Dinitrophenyl-albumin (DNP-albumin) were purchased from Sigma (St. Louis, Mo.). Antibodies for ELISAs were purchased from the Binding Site Inc. or PharMingen (San Diego, Calif.). All the medicinal herbs were of Chinese origin and obtained from The China-Japan Friendship Hospital, Beijing China.

Preparation of Wu Mei Wan Plus Ling Zhi (WMW+LZ)

WMW+LZ, developed in our laboratory, is based on an empirical TCM formula used to treat intestinal parasite infections and chronic diarrhea. A decoction containing 11 medicinal herbs (Table 2) was prepared as described in Chinese Herbal Medicine, Formulas and Strategies: Preparation and Administration of Decoctions (Bensky et al. *Chinese Herbal Medicine: Formulas & Strategies*, Eastland Press, 1999; incorporated herein by reference), and in our previous description (Li et al. "Herbal Medicines on Allergic Asthma" *J. Allergy Clin. Immunol.* 105:S28s–S285 (Abstract); incorporated herein by reference). Briefly, Ling Zhi was boiled separately for 2 hours, and the decoction was filtered and lyophilized (extract A). Radix lateralis aconiti carmichaeli perieparata was boiled for 2 hr, and then the remaining ingredients were added and boiled for an additional 1 hour. The resulting decoction (extract B) was lyophilized and then 10–15 g of A and B, in the ratio 1:10, were administered in an adult-equivalent daily dose. Based on a conversion table of equivalent effective dose ratios from human to animal based on body surface area (Xiu *The Experimental method of pharmacology Beiging*: The People's Public Health Publisher, 1986:985–924; incorporated herein by reference), the dose in this study was 21 mg/mouse administered twice daily.

Peanut Sensitization/Challenge and WMW+LZ Treatment

Mice were sensitized with peanut (5 mg/mouse) plus cholera toxin (10 µg/mouse) administered intragastrically (ig), and boosted 1 and 3 weeks later. One week following the final sensitization dose, mice received either 21 mg WMW+LZ or water (sham) treatment ig twice daily for 7 weeks. Mice were then challenged with 10 mg of crude peanut extract administered ig. Naive mice served as additional controls.

Assessment of Hypersensitivity Reactions

Type I hypersensitivity reactions were scored as previously described (Li et al "A murine model of peanut anaphylaxis: T- and B-cell responses to a major peanut allergen mimic human responses" *J. Allergy Clin. Immunol.* 106:150–158, 2000; incorporated herein by reference): 0—no symptoms; 1—scratching and rubbing around the nose and head; 2—puffiness around eyes & mouth; pilar erecti, diarrhea, reduced activity or standing still with an increased respiratory rate; 3—wheezing, labored respiration, and cyanosis around the mouth; 4—symptoms as in 3 with loss of consciousness, tremors and/or convulsion; and 5—death Measurement of Plasma Histamine Levels and Mast Cell Degranulation Plasma was collected thirty minutes following the challenge and histamine levels were determined utilizing an enzyme immunoassay kit (ImmunoTECH Inc., ME), as described by the manufacturer (Li et al. "A murine model of peanut anaphylaxis: T- and B-cell responses to a major peanut allergen mimic human responses" *J. Allergy Clin. Immunol.* 106:150–158, 2000; incorporated herein by reference).

The numbers of degranulated mast cells, defined as a toluidine positive cells with five or more distinctly stained granules completely outside of the cell were counted in ear tissues collected 40 min after the PN challenge, as previously described (Snider et al. "Production of IgE antibody and allergic sensitization of intestinal and peripheral tissues after oral immunization with protein Ag and cholera toxin" *J. Immunol.* 153:647–657, 1994; Li et al. "A Murine Model of IgE Mediated Cow Milk Hypersensitivity" *J. Allergy Clin. Immunol.* 103:206–214, 1999; each of which is incorporated herein by reference).

Measurement of Serum Antibodies

PN-specific serum IgE concentrations were measured by ELISA as described previously (Li et al. "A murine model of peanut anaphylaxis: T- and B-cell responses to a major peanut allergen mimic human responses" *J. Allergy Clin. Immunol.* 106:150–158, 2000; Li et al. "A Murine Model of IgE Mediated Cow Milk Hypersensitivity" *J. Allergy Clin. Immunol.* 103:206–214, 1999; each of which is incorporated herein by reference). For measurement of total serum IgG and IgE, 96-well plates were coated with rat anti-mouse IgG or IgE capture antibody (2 µg/ml, Sigma or KPL) in coating buffer, pH 9.6. Plates were then blocked and washed in the same manner as above. Samples (1:50 dilution for total IgE and 1:10,000 dilution for total IgG) and ten serial 1:2 dilutions of mouse IgG or IgE (standard curve) were added to the plates and incubated overnight at 4° C. After washing, biotinylated rat anti-mouse IgG monoclonal antibodies or biotinylated rat anti-mouse IgE monoclonal antibodies (0.5 µg/ml; Sigma) were added to the plates, and incubated for an additional 1 hr at room temperature. After washings, avidin peroxidase was added and then washed away 15 min. later with 8×washings. The reactions were developed with ABTS (KPL) for 30 min. at RT and read at 405 nm.

T Cell Culture, Proliferation Assays, and Quantitation of Cytokines

Splenocytes from the spleens of 5 mice in each group were incubated in triplicate cultures in the presence or absence of crude PN extract (50 µg/ml), as described previously (Li et al. "A murine model of peanut anaphylaxis: T- and B-cell responses to a major peanut allergen mimic human responses" *J. Allergy Clin. Immunol.* 106:150–158, 2000; incorporated herein by reference). Cells stimulated with Con A (2 µg/ml) served as a positive control. Three days later the cultures were pulsed for 18-hr with 1 µCi per well of $^3$H-thymidine. Cells were then harvested and the incorporated radioactivity was counted in a β scintillation counter. The results were expressed as counts per minute (cpm).

Splenocytes also were cultured in 24 well plates (4×10$^6$/well/ml) in the presence or absence of PN (50 µg/ml) or Con A (2 µg/ml). Supernatants were collected after 72 h in culture. IL-4, IL-5, IL-13 and IFN-γ were determined by ELISA according to the manufacturer's instructions (PharMingen, San Diego).

Biochemical Assay Analysis of Liver and Kidney Functions

To determine whether WMW+LZ treatment might induce any adverse effect on kidney or liver, we fed naive mice twice the therapeutic dose of WMW+LZ (42 mg/mouse, twice daily) for 7 weeks. Age-matched untreated mice were used as controls. Since relatively large quantities of serum are required for biochemical analyses, sera from each group were pooled. Blood urea nitrogen (BUN), creatinine, total protein, albumin, total bilirubin, alanine aminotransferase (ALT), and glutamate dehydrogenase (GDH) were measured to assess liver and kidney functions. Assays were performed using PROCHEM-V instrumentation (Synbiotics Company, New Jersey). The results were compared with the reference values for each analysis.

Statistical Analysis

Data were analyzed using SigmaStat 2.03 statistical software (SPSS Inc. Chicago, Ill.). Statistical differences in IgE levels, percent mast cell degranulation, and T cell proliferation between two groups (WMW+LZ-treated and sham-treated groups) were compared by student t test, if they were determined to be normally distributed. The Mann-Whitney Rank Sum Test was used to analyze comparisons of in vitro cytokine secretion between the two groups. For rectal temperatures, the difference between the three group (WMW+LZ-treated, sham-treated and naive groups) were analyzed by ANOVA followed by the Bonferroni's t test for all pairwise comparison. $p$ values<0.05 were considered statistically significant.

Results

Protection from Peanut-induced Anaphylactic Reactions

Figure 9A:
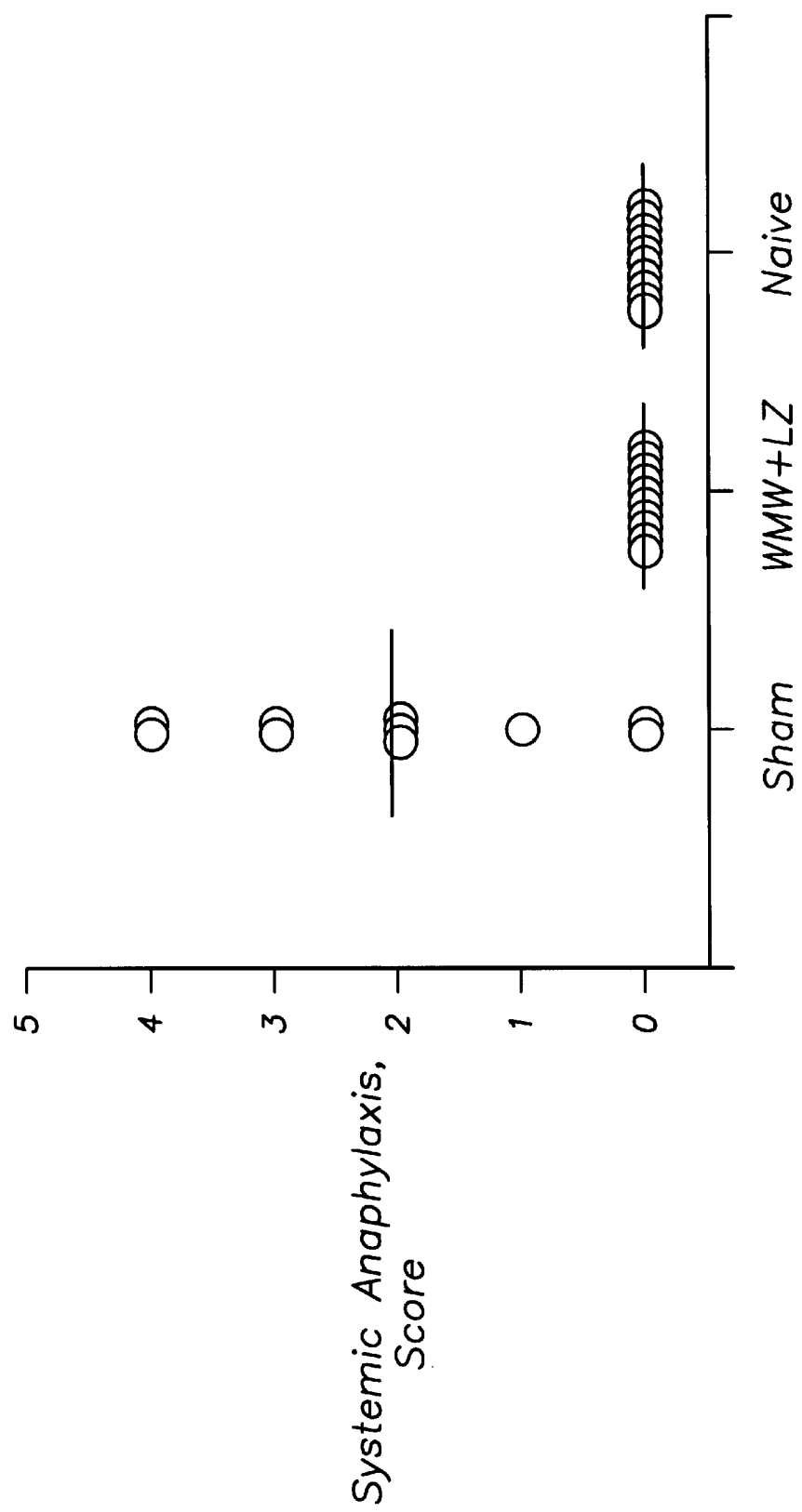
FIG. 9 shows anaphylactic reaction scores following peanut challenge. Anaphylactic symptoms were scored 30–40 minutes after the last challenge dose, as described in the Materials and Methods. Symbols (open circle) indicate individual mice from two sets of experiments (n=10). The bars indicate medians of scores.
Figure 10:
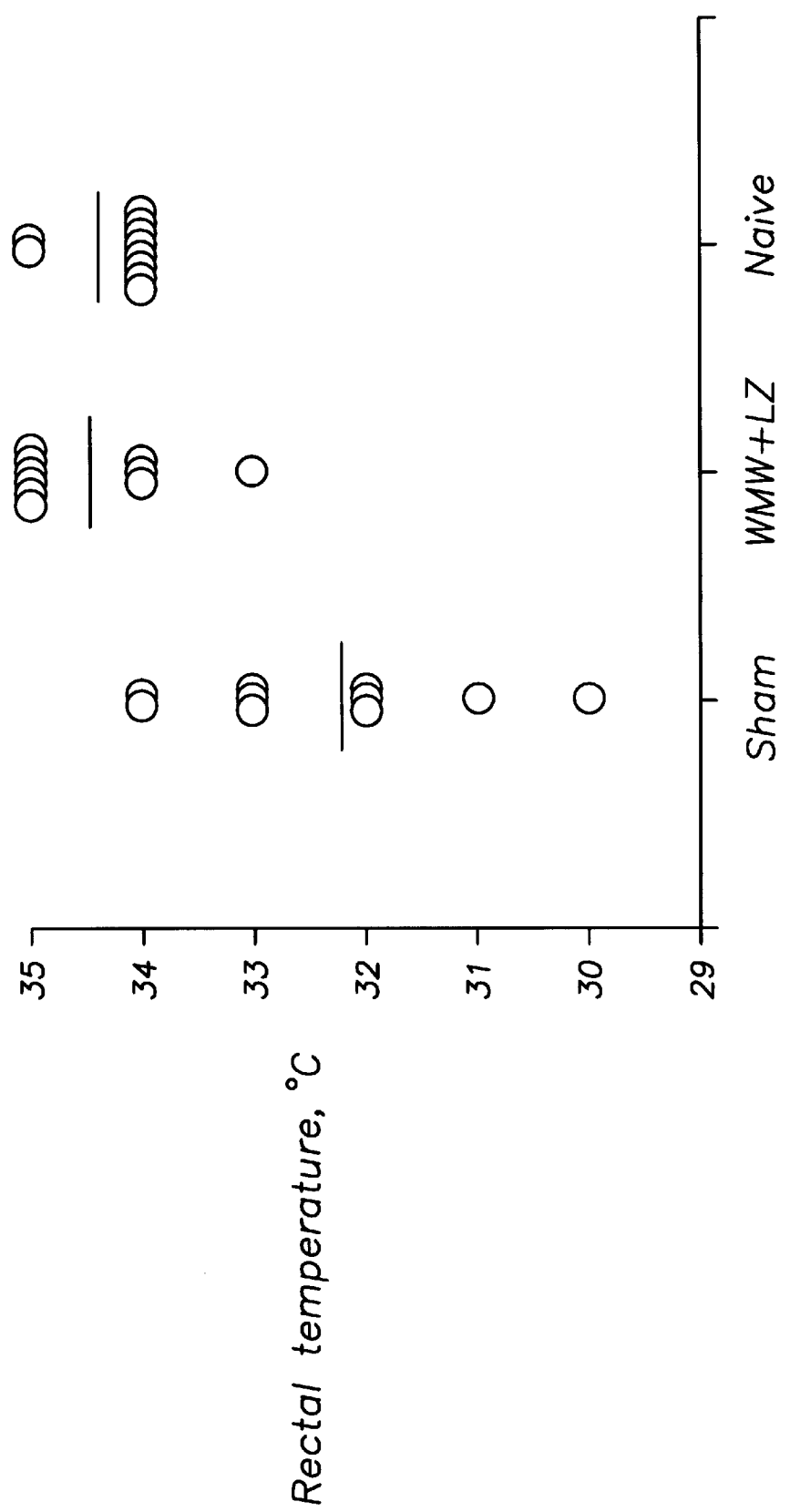
FIG. 10 shows the rectal temperature of the mice following challenge. Rectal temperatures were measured 20 min. after ig peanut challenge. Symbols (open circles) indicate individual mice from two sets of experiments (n=10). Bars indicate means of temperatures. **$p<0.01$ vs. sham.

Anaphylactic symptom scores were determined 30–40 min following oral PN challenge. As depicted in FIG. 9, 80% of the mice in the sham-treated group exhibited symptoms such as itching (score 1, 10%), puffiness around eyes, swelling around the mouth and diarrhea (score 2, 30%), labored respiration (score 3, 20%), and loss of consciousness or little activity after prodding (score 4, 20%). The median score in sham-treated group was 2.2. Symptoms were evident within 15–20 minutes and peaked 30–40 minutes after challenge. In contrast, no symptoms were observed in the WMW+LZ-treated group. No symptoms were seen in the WMW+LZ-treated or naive mice. Since a drop in core body temperature reflects the severity of systemic anaphylaxis in mice, rectal temperatures were obtained 30 min following the PN challenge (von Gamier et al. "Allergen-derived long peptide immunotherapy down-regulates specific IgE response and protects from anaphylaxis" *Eur. J. Immunol.* 30(6):1638–1645, 2000; incorporated herein by reference). Temperatures in the naive group ranged between 34–35° C. following oral PN challenge. The rectal temperatures in 8 of 10 mice in the sham-treated group were 1–4° C. below normal. In contrast, only 1 of 10 mice in the WMW+LZ-treated group had a decrease in core temperature of 1° C. There was a significant difference in the mean temperatures of the sham-treated and WMW+LZ-treated groups (p<0.001) but not between the WMW+LZ-treated group and naive group (FIG. 10). These results demonstrated that WMW+LZ protected peanut-allergic mice from peanut-induced anaphylactic reactions.

Reduction of Mast Cell Degranulation and Plasma Histamine Levels

Figure 11A:
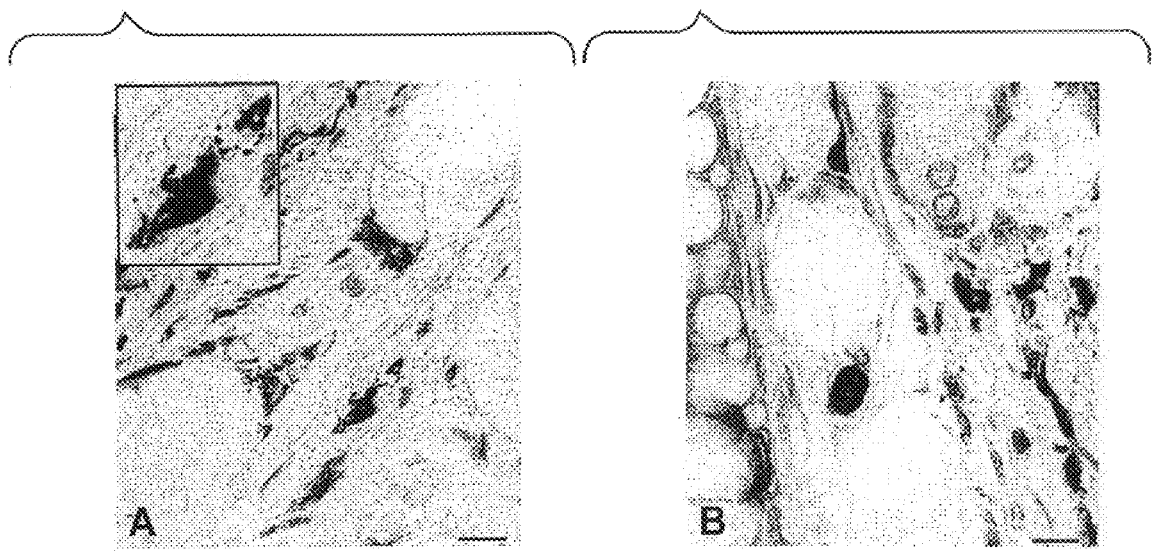
FIG. 11 shows the degranulation of mast cells and measured plasma histamine levels following challenge. Ear samples were collected 40 minutes after challenge and fixed. Five micron paraffin sections were stained with toluidine blue and examined by light microscopy. Panel A illustrates degranulated mast cells in ear samples of sham-treated mice following challenge (bar=10 microns). Inset is high magnification showing granules outside degranulating mast cells. Panel B illustrates normal mast cells in ear sample of WMW+LZ-treated mice. Panel C shows the percentage of degranulated mast cells. 200 to 400 mast cells were counted in each ear sample, and the percentage of degranulated mast cells was determined. Values are expressed as mean±SEM of sections from five mice per group. #, $p<0.001$ vs. controls. Panel D shows plasma histamine levels. Thirty minutes following PN-challenge, blood samples from each group of mice (n=5) were collected, and plasma histamine levels determined using a commercial enzyme immunoassay kit. Values are expressed as the mean±SEM of five mice per group.
Figure 11C:
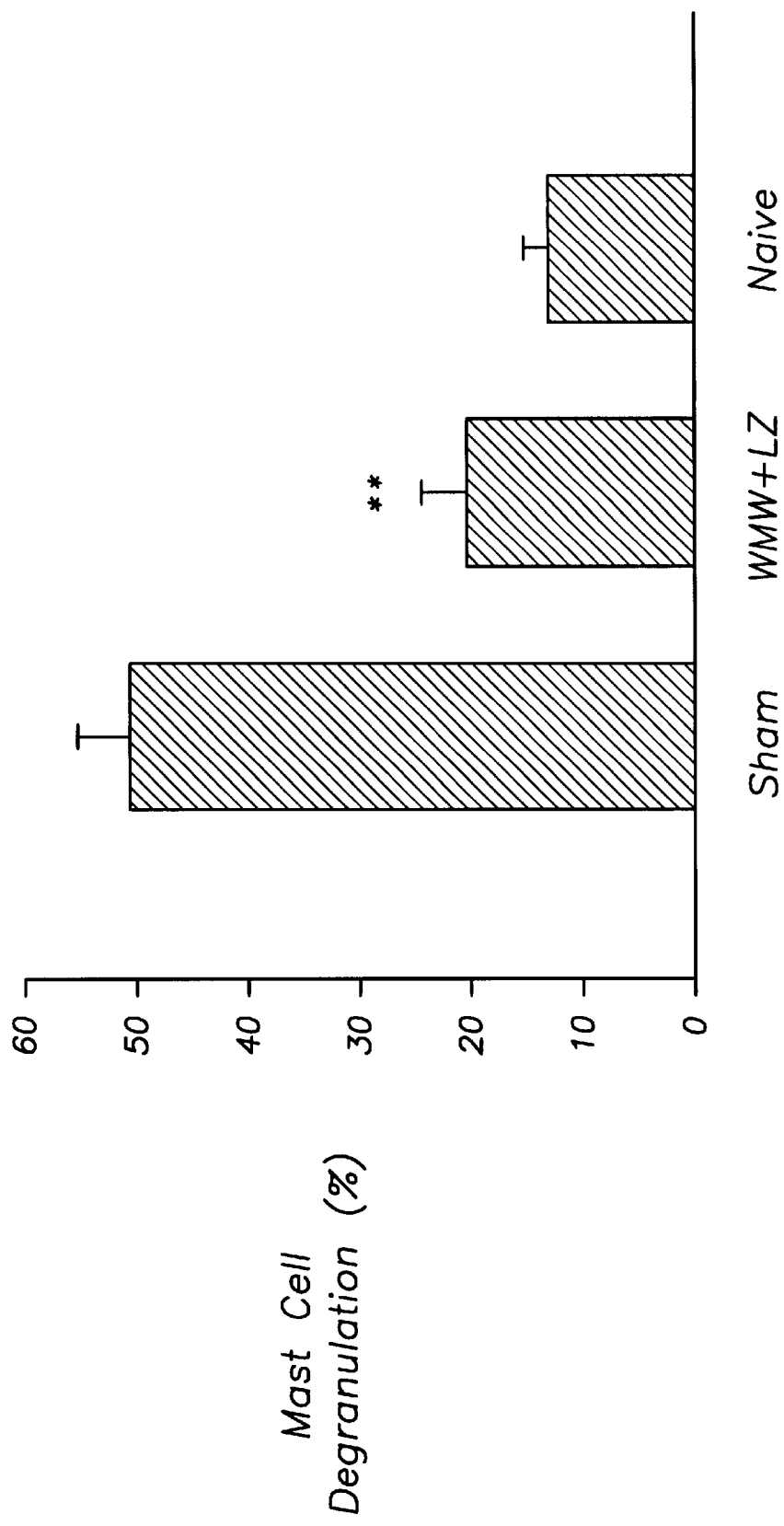
Figure 11D:
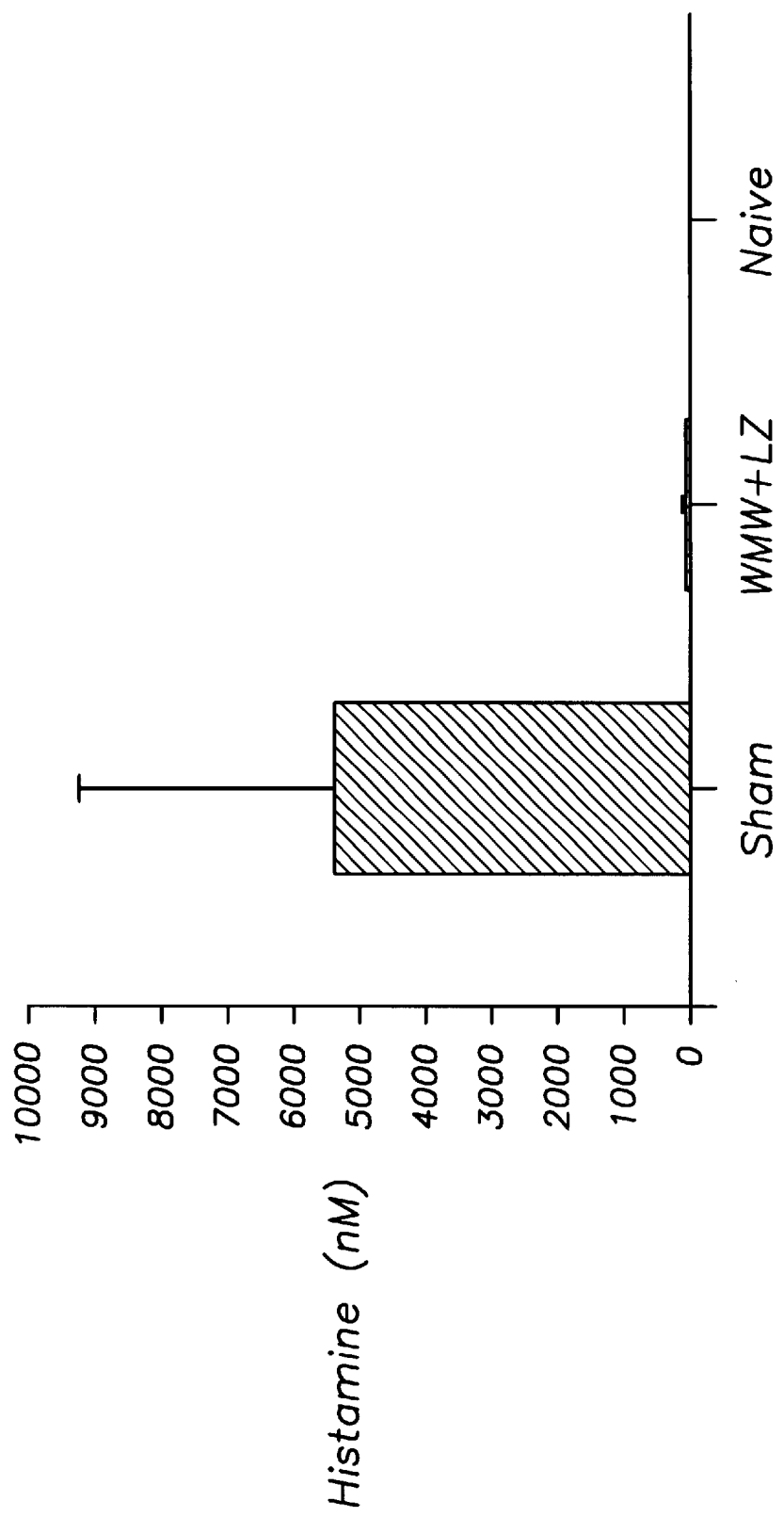

Mast cell degranulation and histamine release are a major factor in anaphylaxis. Consistent with our previous findings, numerous degranulated mast cells (50.6%) were observed in tissues of the sham-treated mice challenged with PN (FIG. 11AB). The numbers of degranulated mast cells were significantly less in the WMW+LZ-treated group compared to sham-treated mice (p<0.001), and were not different than that seen in normal controls. Plasma histamine levels were also markedly elevated in the sham-treated group (5414±3802 nM), but not in the WMW+LZ-treated group (52±31 nM) compared to naive mice (29±11 nM) (FIG. 11D). These results demonstrated that WMW+LZ treatment of peanut allergic mice largely blocked peanut triggered mast cell degranulation and histamine release.

Reduction of Peanut-specific IgE Levels

Figure 8A:
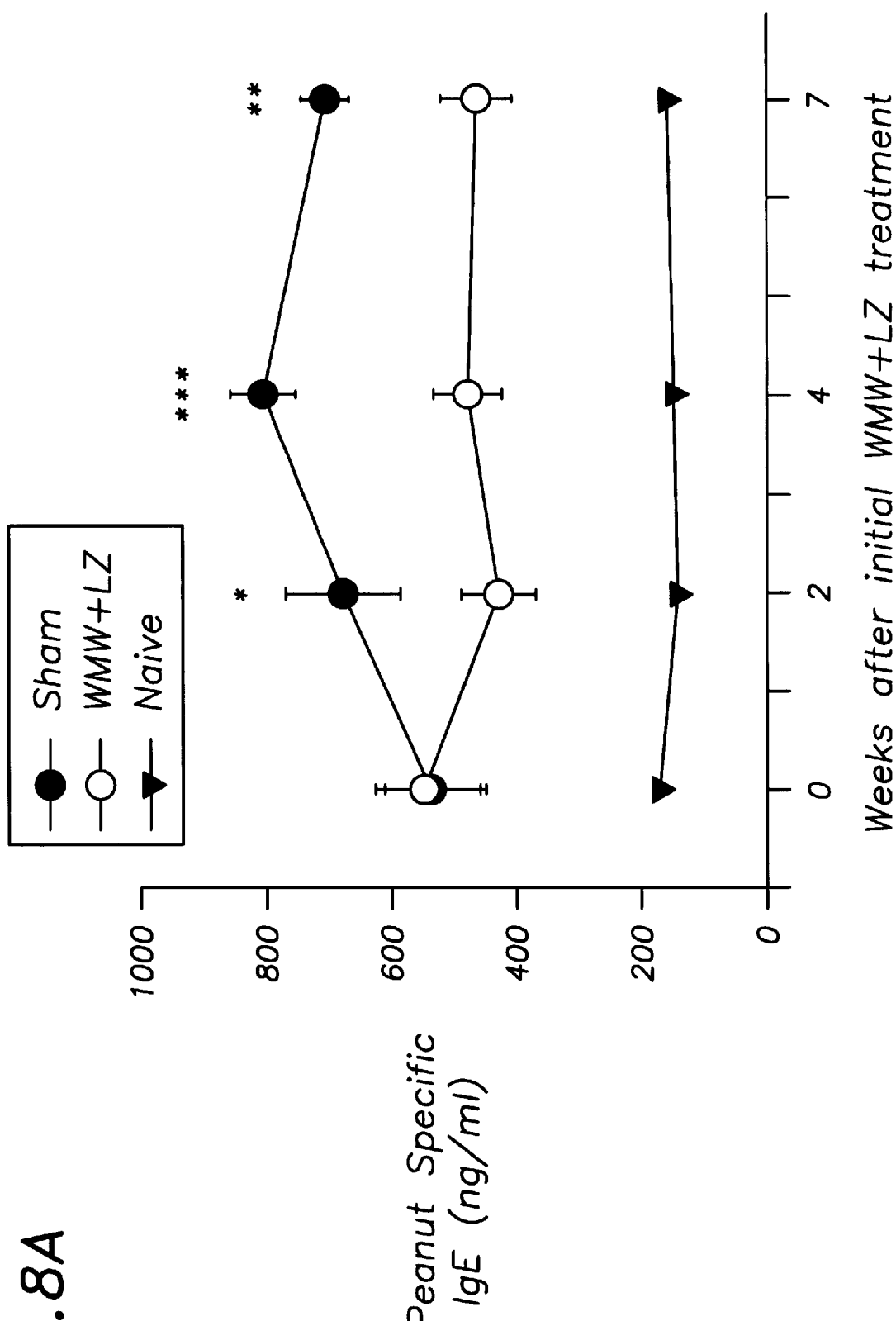
FIG. 8 shows the effect of WMW+LZ administration on antibody levels. Panel A shows the levels of PN-specific IgE after initiating WMW+LZ treatment. Sera from all groups of mice were obtained 4 weeks after the initial sensitization, at which time WMW+LZ treatment was initiated (week 0). Blood sample were obtained every 2–3 weeks during the treatment for seven weeks. Peanut-specific IgE levels were determined by ELISA. Data are given as mean±SEM for each group (Sham, n=10; WMW+LZ, n=10; Naive, n=5) from two experiments. *$p<0.05$ vs. sham; $p<0.01$ vs. sham; *$p<0.001$ vs. sham. Panel B shows peanut-specific IgE levels after discontinuation of WMW+LZ treatment. Mice were sensitized, treated, and challenged as described in FIG. 7, but were not sacrificed following challenge. Instead treatment was discontinued and PN-specific serum IgE levels were re-evaluated 2 and 4 weeks after discontinuation of the treatment. Data are presented as mean values for each group (n=3) in one experiment. Panels C and D shows total IgE and IgG levels, respectively. Mice were sensitized, treated, and challenged as described, and the total serum IgE and IgG concentrations after 7 weeks treatment were determined. Data are recorded as mean±SEM of 10 mice in each group of two experiments.
Figure 8B:
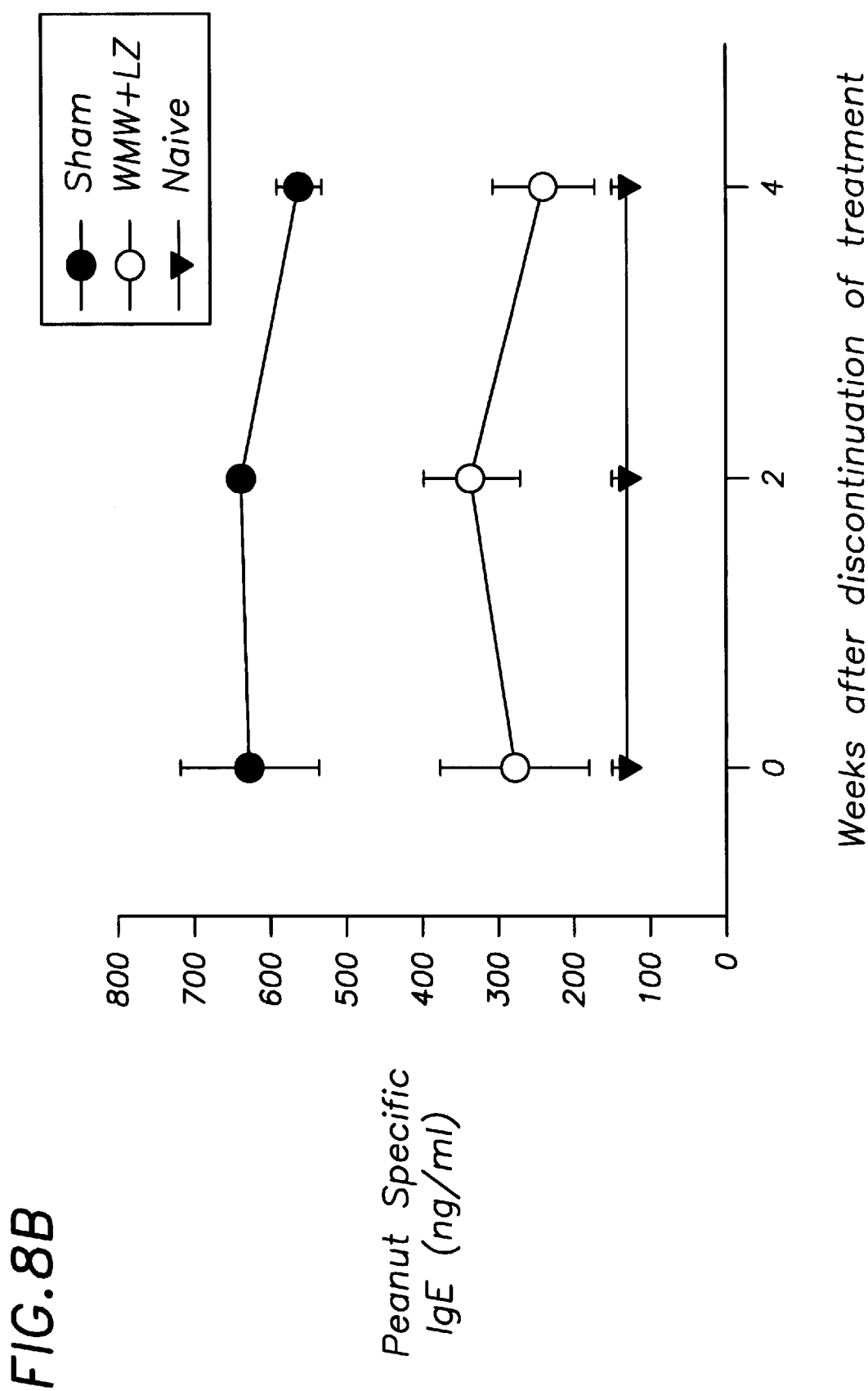
Figure 8C:
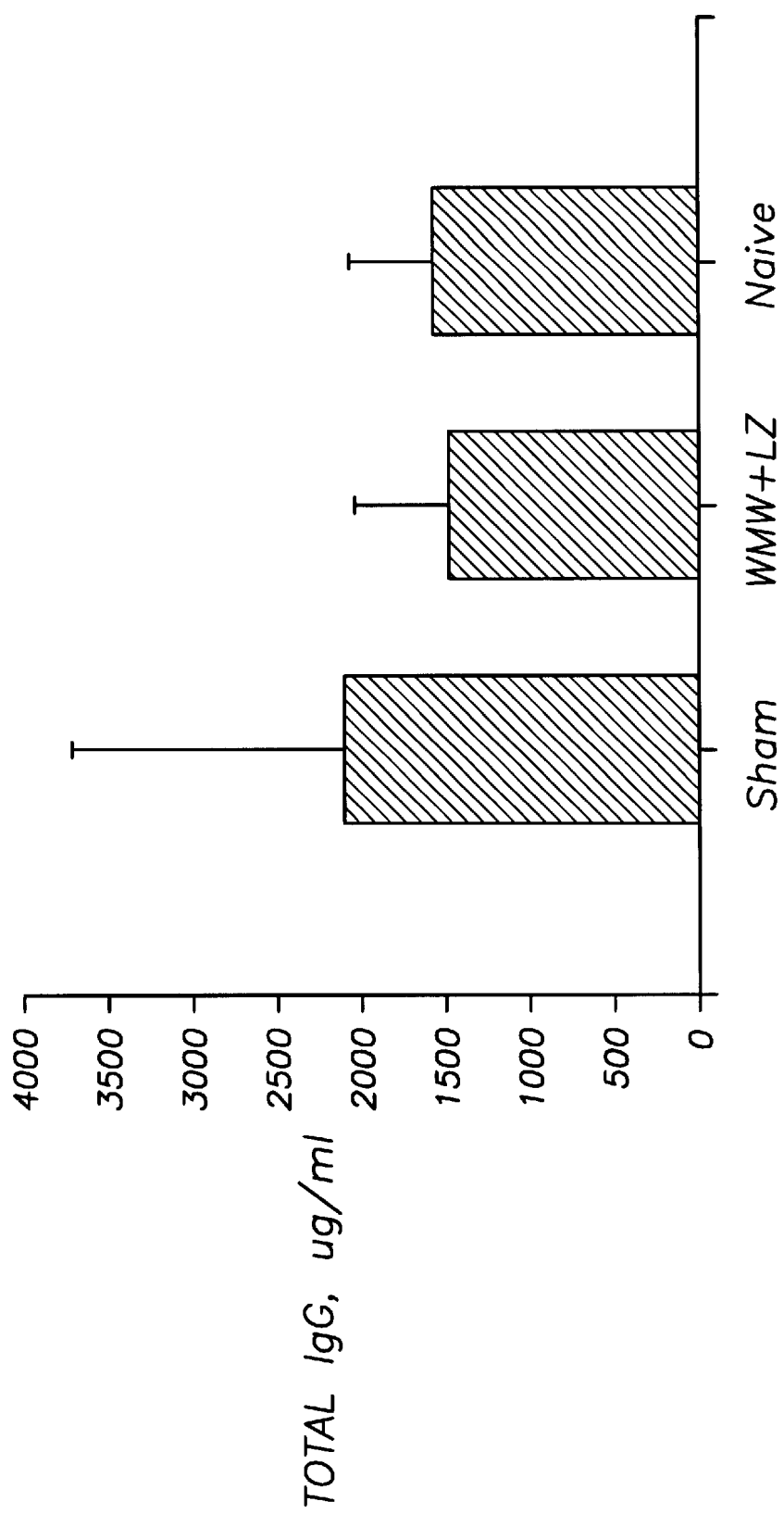
Figure 8D:
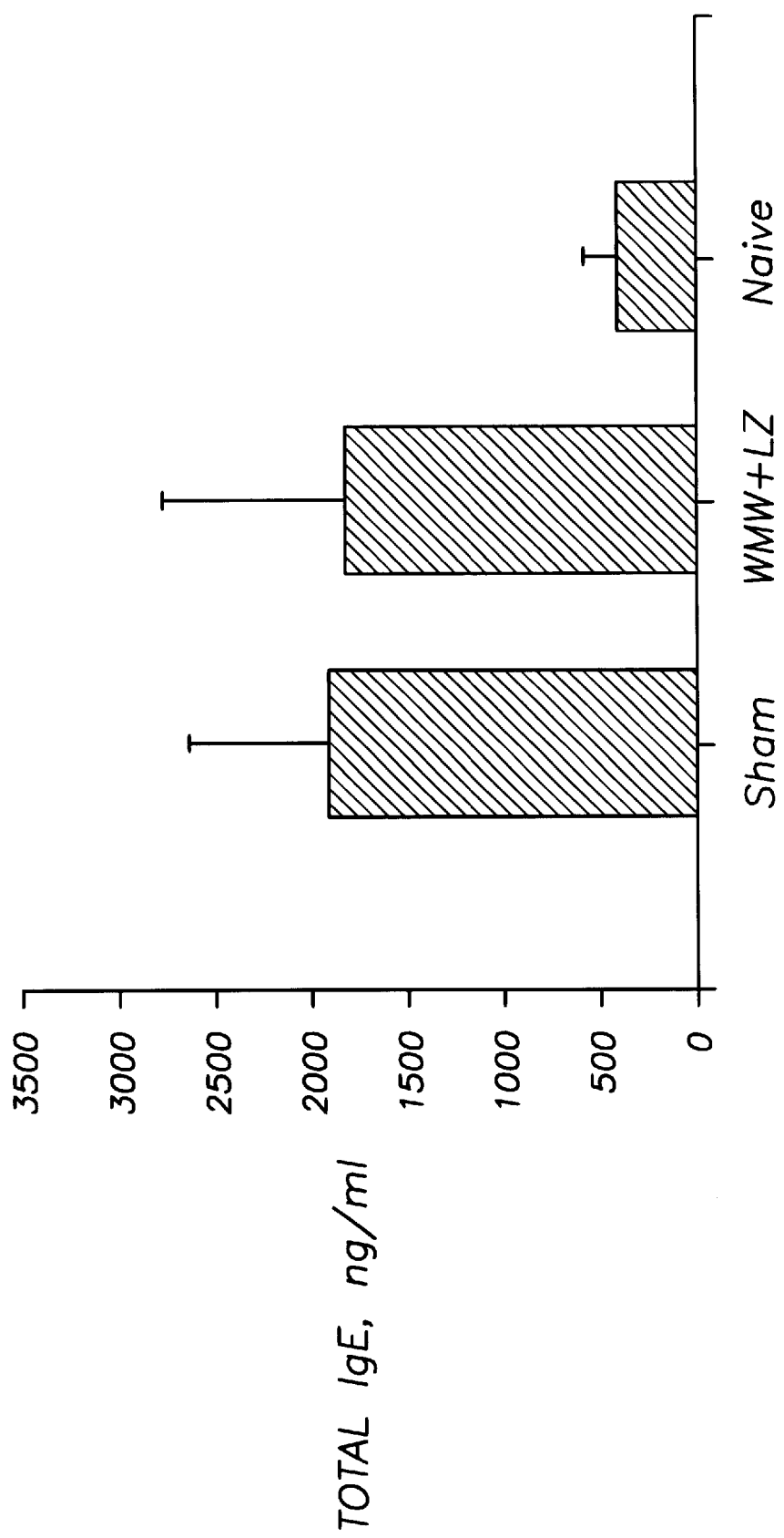

WMW+LZ treatment was initiated 4 weeks after PN-sensitization, at which time peanut-specific IgE levels were markedly elevated in both sensitized groups (Mean±SEM 531±80 ng/ml in WMW+LZ group, 544±82 ng/ml in sham group, FIG. 8A). Following two-weeks of treatment, IgE levels in the WMW+LZ-treated group were significantly lower than those in sham-treated group, and remained significantly lower throughout the course of treatment (468±57 ng/ml in WMW+LZ, 706±154 ng/ml in sham, p<0.01 at time of challenge). In an additional group, mice were not sacrificed after challenge, treatment was discontinued, and IgE levels were monitored for an additional 4 weeks. At that time, IgE levels were essentially the same as at the time treatment was discontinued (347±98 at week 0, 343±69 at week 4, FIG. 8B), and were approximately one-half the levels seen in sham-treated mice (726±95 ng/ml), demonstrating that WMW+LZ had a persistent effect lasting for at least 4 weeks. Interestingly, WMW+LZ treatment did not significantly alter total serum IgE or IgG levels (FIG. 8CD).

Suppression of Peanut-specific T Cell Proliferation and Th2 Cytokine Production

Figure 12A:
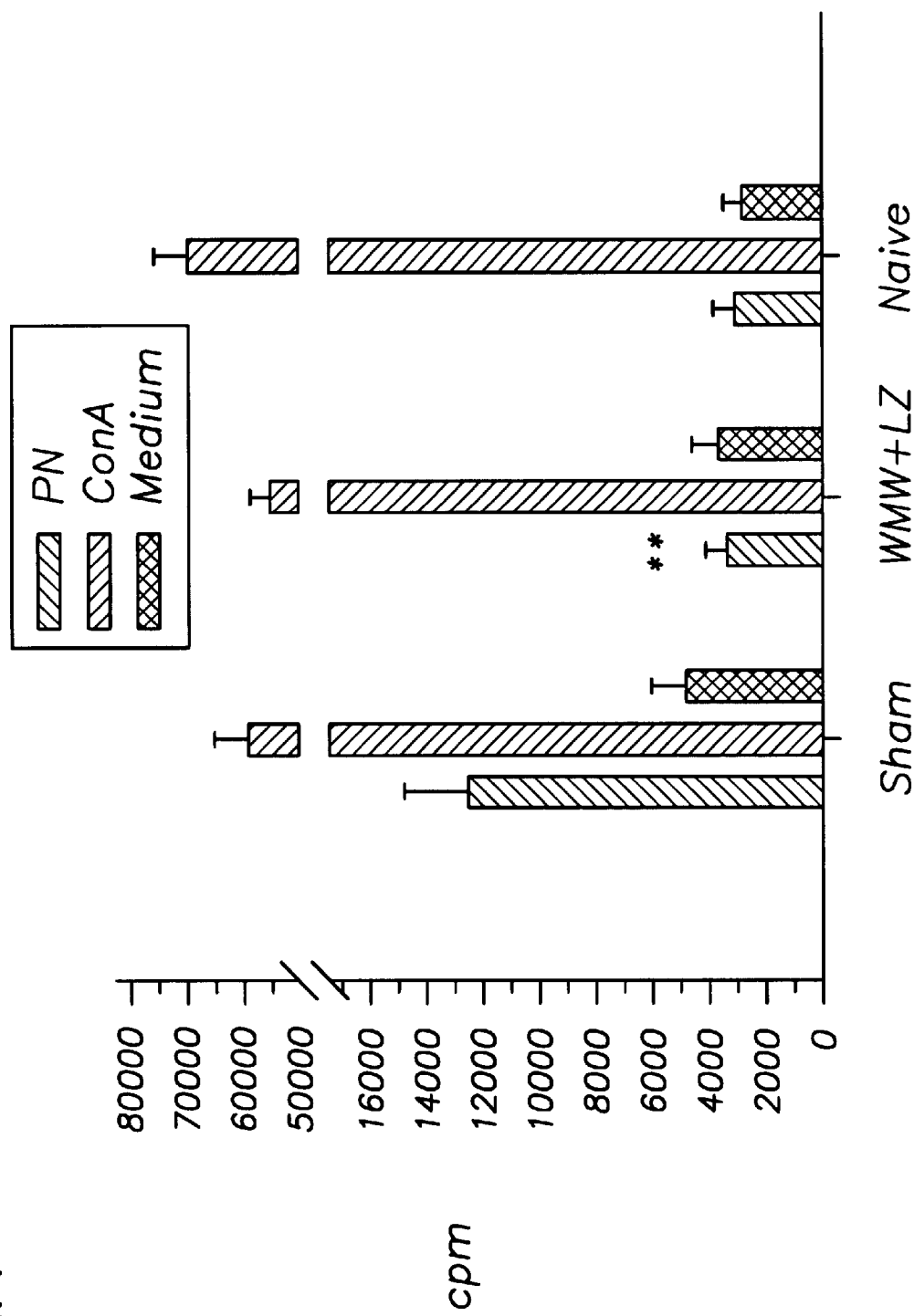
FIG. 12 shows the effect of WMW plus LZ administration on splenocyte proliferative response. Immediately after the evaluation of anaphylactic reactions, mice were sacrificed and spleen cells were isolated from each group of mice and pooled (n=5). Triplicate cultures were stiumlated with crude peanut extract. Cells cultured in medium alone or with Con A served as controls. Three days later, the cultures were pulsed for 18 hours with 1 µCi per well of $^3$H-thymidine. The cells were harvested, and the incorporated radioactivity was counted. Data are presented as mean±SEM of two sets of triplicate wells of two experiments. **p<0.01 vs. sham. Panels B, C, and D show cytokine levels. Cell suspensions were cultured in complete culture medium in the presence of peanut antigen, Con A, or medium alone. Supernatants were collected 72-hr. later, and IL-4, IL-5, IL-13, and IFN-γ were determined by ELISA. Results are expressed as mean±SEM of two duplicate cultures from two experiments. *p<0.05; **p<0.01 vs. sham.

Consistent with our previous finding, splenocytes from sham-treated, PN-allergic mice showed a marked proliferative response in vitro to PN stimulation (FIG. 12A). In contrast, the proliferative response of splenocytes from WMW+LZ-treated PN-allergic mice following PN stimulation were significantly less than that of sham-treated mice (p<0.01), but essentially the same as that of naive spleen cells. Interestingly, WMW+LZ treatment did not decrease the proliferative response to Con A stimulation.

Figure 12B:
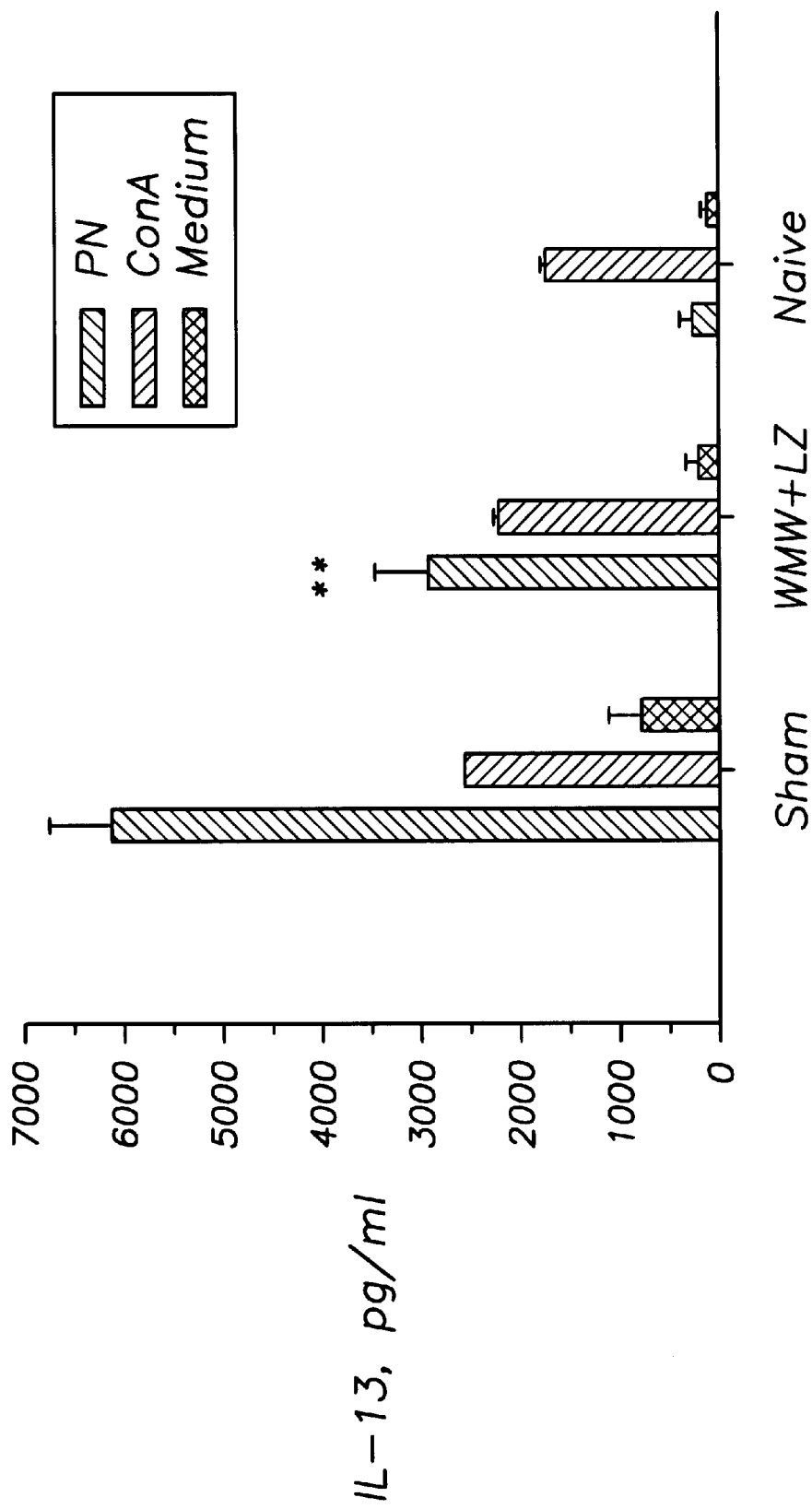
Figure 12C:
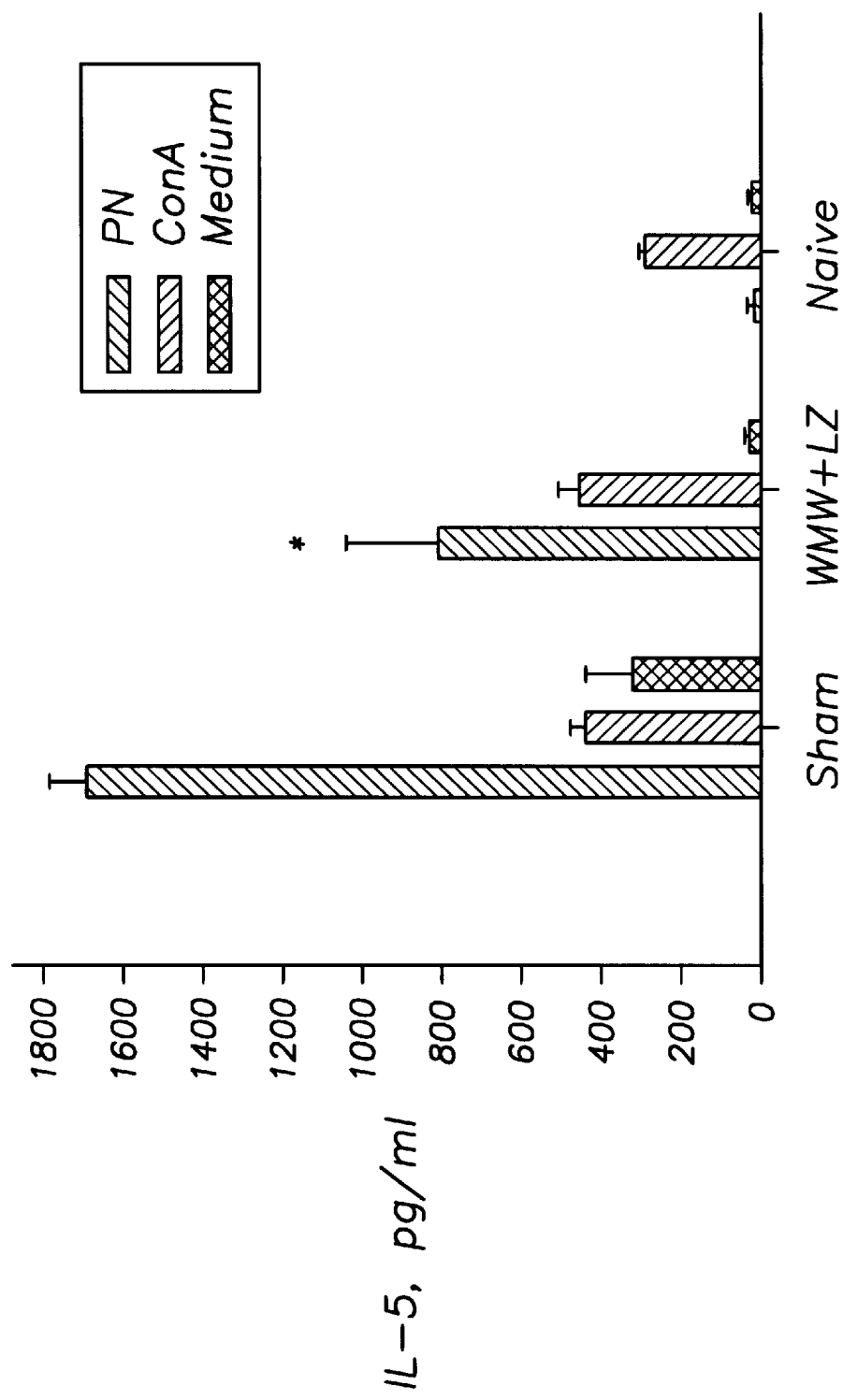
Figure 12D:
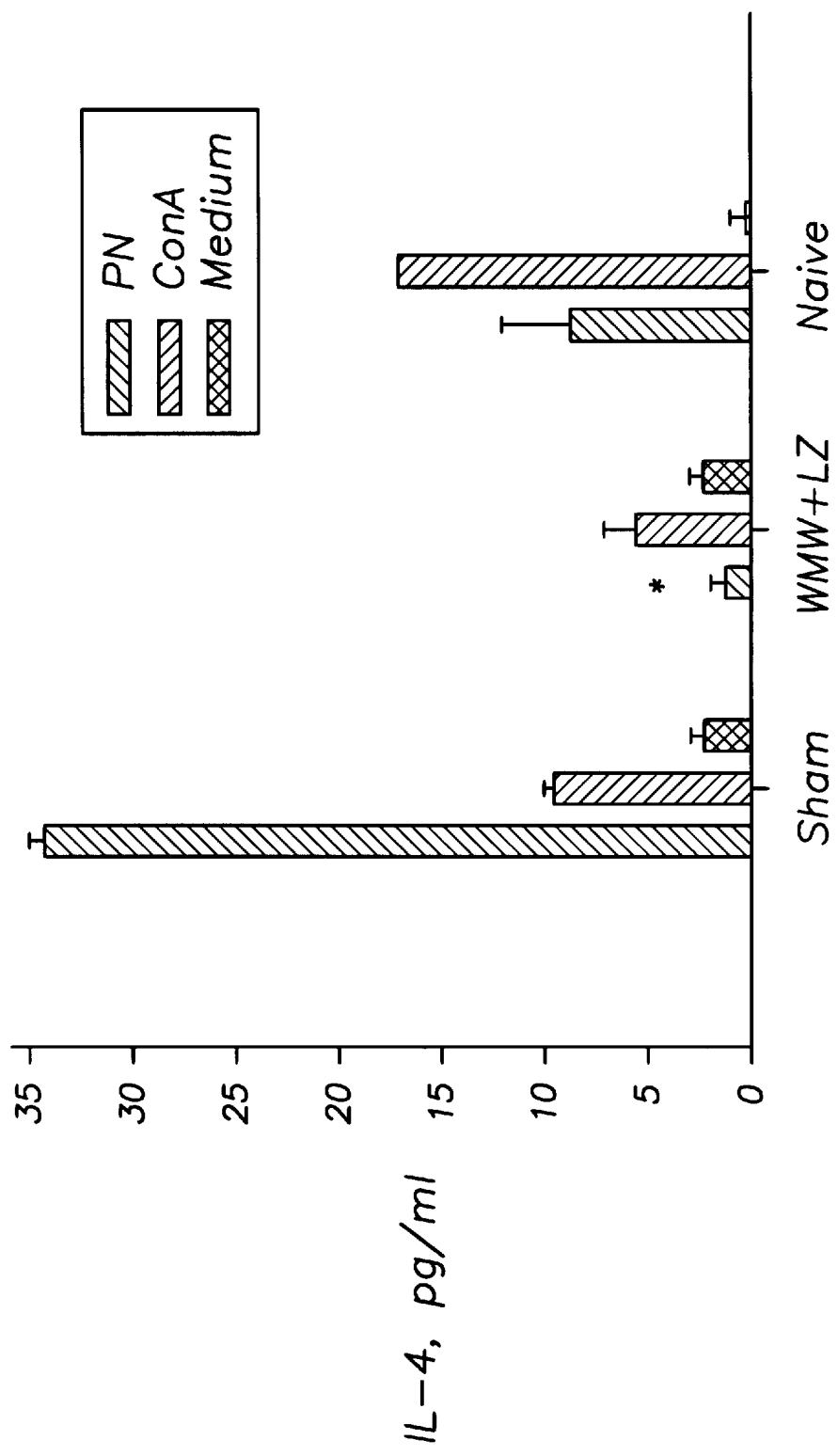

Splenocytes from WMW+LZ treated mice secreted significantly less IL-4, IL-5, and IL-13 than splenocytes from sham-treated mice following PN stimulation (FIG. 12BCD). However, IL-4, IL-5, and IL-13 secretion following Con A stimulation was not significantly different in splenocytes from WMW+LZ-treated and sham-treated mice. WMW+LZ treatment did not alter either PN- or Con A-stimulated IFN-γ production (PN: 1367±582 ng/ml in sham and 1417±1140 ng/ml in WMW+LZ; Con A: 1461±569 ng/ml in sham and 1761±1132 ng/ml in WMW+LZ). These results suggest that WMW+LZ treatment resulted in specific suppression of both PN-induced T cell proliferation and PN-activated Th2 cytokine secretion.

WMW+LZ Appears to be Non-toxic

No signs of adverse effects were noted in WMW+LZ-treated, PN-allergic mice or naive mice though out the treatment. Body weights of WMW+LZ-treated mice did not differ from untreated mice (data not shown). Liver and kidney function tests of WMW+LZ-treated PN-allergic mice and naive mice were within normal limits and not different than those of sham-treated PN-allergic mice and untreated naïve mice (Table 6). These results demonstrated that oral WMW+LZ treatment had no adverse effects on hepatic and renal functions.

TABLE 6

BIOCHEMICAL ASSESSMENT FOR LIVER AND KIDNEY FUNCTION

|  | PN/WMW + LZ[a] | PN/Sham[a] | Naive[a] | WMW + LZ[b] | Naive[b] | Naïve WMW + LZ[c] | Naïve[c] | Reference Range | Units |
|---|---|---|---|---|---|---|---|---|---|
| BUN | 20 | 22 | 19 | 18 | 19 | 18 | 15 | 9–36 | mg/dL |
| Total Protein | 5.8 | 5.8 | 5.9 | 5.8 | 5.9 | 5.2 | 4.2 | 5.9–6.9 | g/dL |
| Albumin | 3.2 | 3.5 | 3.7 | 3.4 | 3.5 | 2.6 | 3.2 | 2.4–4.4 | g/dL |
| Creatinine | 0.6 | 0.7 | 0.4 | 0.3 | 0.4 | 0.3 | 0.4 | 0.4–1 | mg/dL |
| T-Bilirubin | 0.8 | 0.8 | 0.4 | 0.2 | 0.2 | 0.3 | 0.3 | 0.4–0.8 | mg/dL |
| ALT (SGPT) | 36 | 36 | 29 | 32 | 32 | 40 | 41 | 22–400 | U/L |
| Alb/Glob Ratio | 1.3 | 1.5 | 1.7 | 1.4 | 1.5 | 1.0 | 2.5 | 0.6–1.2 |  |
| Globulin | 2.5 | 2.3 | 2.2 | 2.4 | 2.4 | 2.5 | 1.0 | 2.1–4.3 | g/dL |

Figure 7:
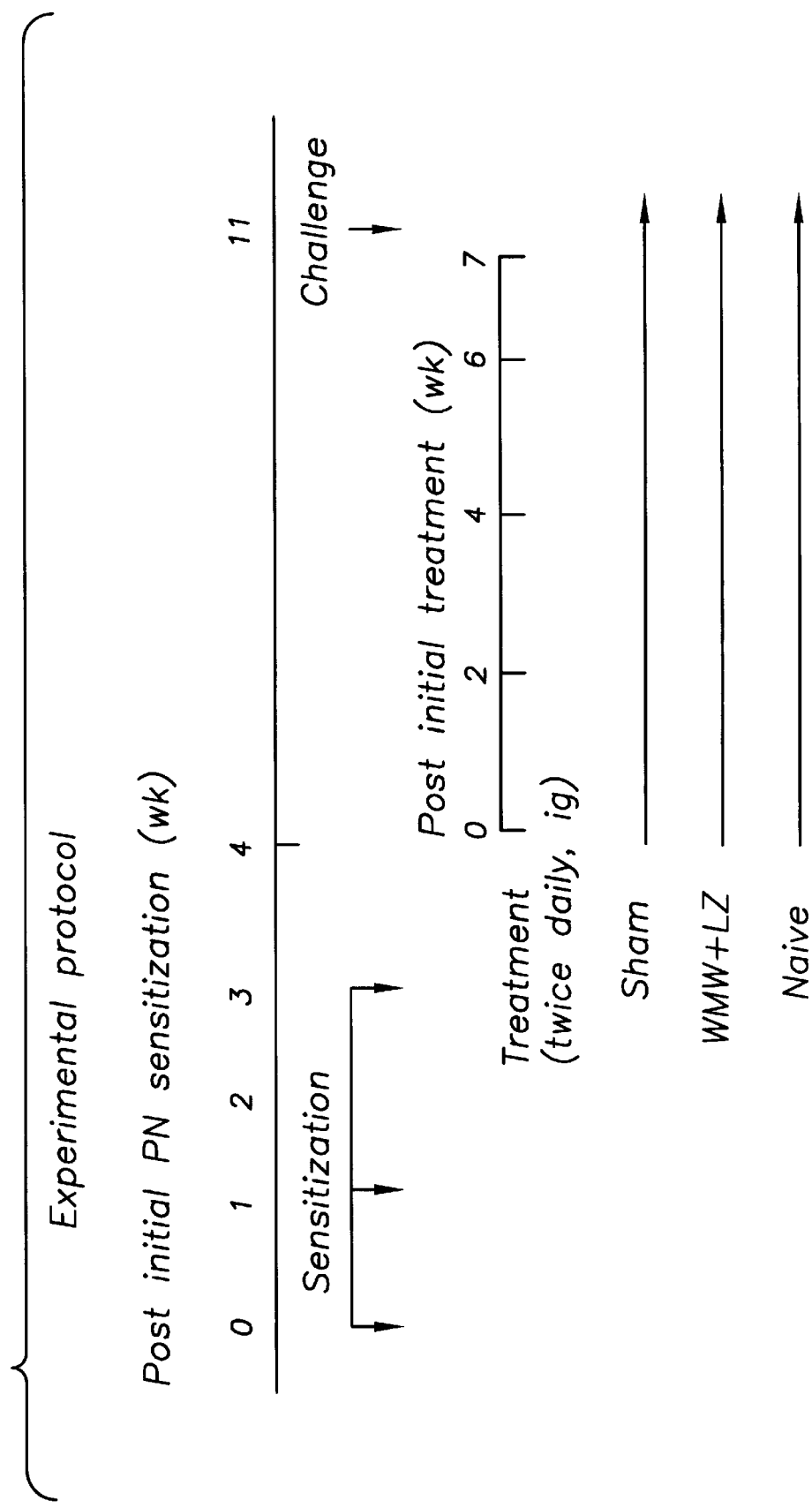
FIG. 7 shows the experimental protocol in determining the effect WMW plus LZ administration in a murine model of allergies. Mice were sensitized by intragastric (ig) feeding with peanut (5 mg/mouse) in the presence of cholera toxin (10 $\mu$g/mouse), and boosted orally 1 and 3 weeks later. Beginning at week 4, groups of mice received either 21 mg WMW+LZ in 0.5 ml of spring water or spring water alone as sham treatment, twice daily for 7 weeks. Blood was drawn at 4 weeks after the initial PN sensitization and every 2–3 weeks during the treatment phase. Mice were then challenged with 10 mg crude peanut extract at week 11. Naive mice were also challenged and served as additional controls. After scoring anaphylactic symptoms, mice were sacrificed and blood samples were collected for in vitro studies.

[a]Mice were sensitized, treated and challenged as described as FIG. 7. Blood was obtained after 7 weeks of treatment from each group (n = 10) and sera were pooled.
[b]Naïve mice were fed with WMW + LZ (42 mg/mouse, twice daily or untreated). Blood was drawn after the 7 weeks of treatment. Sera were pooled from each group mice (n = 3).
[c]Naïve mice were fed with WMW + LZ (42 mg/mouse, twice daily or untreated) for 7 weeks or untreated. Blood was drawn 7 weeks after discontinuation of the treatment. Sera were pooled from each group mice (n = 5) Biochemical assay were performed. All the samples are within the normal range.

Example 5

Passive Desensitization of Human Basophils

Introduction

One of the ways in which inventive herbal formulations may be characterized is by their ability to inhibit histamine release in isolated basophils that are contacted with antigen. The present Example describes one procedure by which such basophil histamine release is assayed; those of ordinary skill in the art will recognize that various modifications and alterations of this precise procedure can be made without departing from the spirit or scope of the present invention. Basophil histamine release assays are well established in the art (to give but a few examples, see Counsell et al., *J. Allergy Clin. Immunol.* 98:884, 1996; Haselden et al., *J. Exp. Med.* 189:1885, 1999; each of which is incorporated herein by reference).

Materials and Methods

REAGENTS: EDTA, 0.1M: 37.23 g Disodium EDTA; 600 ml $H_2O$; adjust pH to 7.18–7.20 with 50% NaOH; add $H_2O$ to IL. 10×HBS: 80.0 g NaCl; 3.7 g KCl; 23.8 g HEPES (free acid); add $H_2O$ to 1 L. Filter, autoclave, store at 4° C. 1×HBS. PH 7.4: Dilute 10× stock to 1× with distilled H20. Adjust pH with 10 N NaOH. Filter, autoclave, store at 4° C. HBS (+ALBUMIN): 100 ml 1×HBS; 0.125 ml 25% solution of Human serum albumin (ALBUMAC™, Baxter Scientific). HBS+1 MM $CaCl_2$: 100 ml HBS (+albumin); 10 μl $CaCl_2$; 50 μl $MgCl_2$ PROTOCOL: 15 ml of venous blood from a sensitized individual is drawn into a plastic syringe containing 5 ml of 0.1 M EDTA pH 7.2. Blood should be drawn gently to avoid lysis. Samples are transferred to 50 ml polycarbonate tubes containing 10 ml clinical Dextran 70. Preferably, the tubes have previously been washed without detergent and rinsed at least three times in distilled, deionized water. Blood should be poured down the side of the tube to avoid bubbles, and should be mixed by gentle swirling.

Cells are allowed to sediment at room temperature until a sharp interface develops between the red cells and plasma (which contains leukocytes and platelets), generally 60–90 mins. Cells should not sit longer than 2 hours. Plasma (buffy coat) layer is drawn off using a 3 ml plastic transfer pipette and is transferred to polycarbonate centrifuge tubes. Plasma is then centrifuged for 10 min at 450 g, 4° C.

Supernatant is carefully poured off, and the cell button is resuspended by gently shaking the tubes. Bubbles should be avoided. 30 ml (approximately 2× the initial cell volume) of cold HBS-albumin is added to the cells, the cells are resuspended and are recentrifuged for 10 min at 200 g, 4° C. This step, which functions as a wash, is repeated promptly. The supernatant is them completely poured off, and the cells are resuspended in 1 ml of cold HBS+3 mM $CaCl_2$. Cells are then counted and additional buffer is added to adjust the cell concentration to $1×10^7$ cells/ml. At this point, the cells are ready for use in basophil (leukocyte) histamine release assay.

For the histamine release assays, which should always be performed at least in duplicate, reaction tubes are prepared as follows: 50 μl cold HBS+3 mM $CaCl_2$ are added to control (total and spontaneous release) tubes; 25 μl cold HBS+3 mM $CaCl_2$ and 25 μl HRF supernatant are added to test tubes. Two batches of test tubes are prepared: those that will receive cells that were not previously incubated with the herbal formulation, and those that will receive cells that were previously incubated with the herbal formulation (optionally, additional batches of test tubes are prepared that will receive cells that have been incubated with different concentrations of herbal formulation).

Leukocyte suspension (in HBS+3 mM $CaCl_2$) is warmed at 37° C. for 6 min. In different tubes, leukocytes are mock incubated or are actually incubated with the herbal formulation for 15–120, preferably 15–30 minutes. Then, 50 μl of the appropriate suspension is added to each reaction tube. Liquids are mixed by light finger vortexing. Tubes are then placed in a 37° C. bath for 45 minutes.

After the 45 minute incubation, total release control tubes are placed in boiling water for 10 minutes and then are immediately transferred to ice. 700 μl of cold HBS+1 mM $CaCl_2$ are then added, and the tubes are kept on ice until other tubes have been processed. Challenge antigen is then added to test tubes. For example, challenge antigen may be in any desired form (e.g., crude, purified, recombinant, etc.). In certain situations, it may be desirable to use a form of the antigen that includes only a subset of all possible epitopes found in the antigen in its native form. For example, some epitopes may have minimal clinical relevance (e.g., if they are not normally encountered by sensitive individuals in the routes of exposure through which those individuals typically encounter antigen). Without wishing to be bound by any particular theory, we propose that conformational epitopes are not always clinically relevant for antigens that are naturally encountered orally because such epitopes often do not pass through the gastrointestinal lining. Thus, it may sometimes be desirable to exclude conformational epitopes (e.g., by using denatured or fragmented antigen) from the challenge antigen in order to minimize "false" (i.e., not clinically relevant) histamine release.

Test tubes and spontaneous release control tubes are processed by adding 700 µl cold HBS+1 mm $CaCl_2$ to each tube and centrifuging the tubes immediately in a microcentrifuge. 750–800 µl of supernatant is then transferred to a fresh tube. At this point, supernatants may be frozen or alternatively may be assayed for histamine content by spectrofluorimetry. Percentage of histamine release is calculated from the mean histamine release (ng/ml) values using the equation:

% release=[(test sample)−(spontaneous)/(total release)−(spontaneous)]×100.

Results

The herbal formulations are characterized as effective according to the present invention if the amount of histamine released from cells incubated with the herbal formuation is reduced at least about 20% preferably at least about 30%, 40%, 50%, 60%, 70%, 80%, 90%, 95%, 97%. 98% or 99% as compared with the amount of histamine released from corresponding cells that were not so incubated.

Other Embodiments

Those of ordinary skill in the art will readily appreciate that the foregoing has provided descriptions of certain preferred embodiments of the present invention; various modifications and alterations to these descriptions can be made without departing from the spirit or scope of the present invention, which is defined as set forth in the following claims.

What is claimed is:

1. A composition for treating allergies or asthma comprising effective amounts of aqueous extracts of Fructus Pruni Mume, Pericarpium Zanthoxyli Bungeanum, Herba cum Radice Asari, Rhizoma Coptidis, Corex Phellodendri, Rhizoma Zingiberis Officinalis, Radix Lateralis Aconiti Carmichaeli Praeparata, Ramulus Cinnamomi Cassiae, Radix Ginseng, and Radix Angelicae Sinensis.

2. A composition for treating allergies or asthma comprising effective amounts of aqueous extracts of Fructus Pruni Mume, Pericarpium Zanthoxyli Bungeanum, Herba cum Radice Asari, Rhizoma Coptidis, Corex Phellodendri, Rhizoma Zingiberis Officinalis, Radix Lateralis Aconiti Carmichaeli Praeparata, Ramulus Cinnamomi Cassiae, Radix Ginseng, Radix Angelicae Sinensis, and the yeast *Ganoderma lucidum*.

3. A composition for treating allergies or asthma comprising effective amounts of organic solvent extracts of Fructus Pruni Mume, Pericarpium Zanthoxyli Bungeanum, Herba cum Radice Asari, Rhizoma Coptidis, Corex Phellodendri, Rhizoma Zingiberis Officinalis, Radix Lateralis Aconiti Carmichaeli Praeparata, Ramulus Cinnamomi Cassiae, Radix Ginseng, and Radix Angelicae Sinensis.

4. A composition for treating allergies or asthma comprising effective amounts of organic solvent extracts of Fructus Pruni Mume, Pericarpium Zanthoxyli Bungeanum, Herba cum Radice Asari, Rhizoma Coptidis, Corex Phellodendri, Rhizoma Zingiberis Officinalis, Radix Lateralis Aconiti Carmichaeli Praeparata, Ramulus Cinnamomi Cassiae, Radix Ginseng, Radix Angelicae Sinensis, and *Ganoderma lucidum*.

5. A composition for treating allergies or asthma comprising effective amounts of ground dried preparations of at least herbs Fructus Pruni Mume, Pericarpium Zanthoxyli Bungeanum, Herba cum Radice Asari, Rhizoma Coptidis, Corex Phellodendri, Rhizoma Zingiberis Officinalis, Radix Lateralis Aconiti Carmichaeli Praeparata, Ramulus Cinnamomi Cassiae, Radix Ginseng, and Radix Angelicae Sinensis prepared by grinding and drying the herbs.

6. A composition for treating allergies or asthma comprising effective amounts of ground dried preparations of at least herbs Fructus Pruni Mume, Pericarpium Zanthoxyli Bungeanum, Herba cum Radice Asari, Rhizoma Coptidis, Corex Phellodendri, Rhizoma Zingiberis Officinalis, Radix Lateralis Aconiti Carmichaeli Praeparata, Ramulus Cinnamomi Cassiae, Radix Ginseng, Radix Angelicae Sinensis, and yeast *Ganoderma lucidum* prepared by grinding and drying the herbs and yeast.

* * * * *